US006194407B1

(12) United States Patent
Failli et al.

(10) Patent No.: US 6,194,407 B1
(45) Date of Patent: Feb. 27, 2001

(54) TRICYCLIC PYRIDO VASOPRESSIN AGONISTS

(75) Inventors: Amedeo A. Failli, Princeton Junction; Jay S. Shumsky, Cranbury, both of NJ (US); Robert J. Steffan, Langhorne, PA (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/122,123

(22) Filed: Jul. 24, 1998

Related U.S. Application Data
(60) Provisional application No. 60/054,180, filed on Jul. 30, 1997.

(51) Int. Cl.⁷ .................. A61K 31/695; A61K 31/55; C07D 243/10; A61P 5/10
(52) U.S. Cl. .................. 514/220; 514/63; 540/557
(58) Field of Search .................. 514/63, 220; 540/557

(56) References Cited

U.S. PATENT DOCUMENTS

| | | | |
|---|---|---|---|
| 4,766,108 | 8/1988 | Ali | 514/16 |
| 5,055,448 | 10/1991 | Manning et al. | 514/16 |
| 5,070,187 | 12/1991 | Gavras et al. | 530/315 |
| 5,420,270 | 5/1995 | Chandrakumar et al. | 540/488 |
| 5,512,563 | 4/1996 | Albright et al. | 514/217 |
| 5,516,774 | 5/1996 | Albright et al. | 514/220 |
| 5,521,173 | 5/1996 | Venkatesan et al. | 514/220 |
| 5,536,718 | 7/1996 | Albright et al. | 514/220 |
| 5,932,745 | * 8/1999 | Dushin et al. | 548/540 |

FOREIGN PATENT DOCUMENTS

| | | |
|---|---|---|
| 4999 | 4/1967 | (FR) . |
| 8-81460 | 3/1996 | (JP) . |
| 9534540 | 12/1995 | (WO) . |
| 9622282 | 7/1996 | (WO) . |
| 9722591 | 6/1997 | (WO) . |

OTHER PUBLICATIONS

Cervoni, P. and Chan, P.S., Diuretic Agents, in Kirk–Othmer: Encyclopedia of Chemical Technology, 4th Ed., Wiley, vol. 8, 398–432, 1993.
Jackson, E. K., Goodman's and Gilman's The Pharmacological Basis of Therapeutics, 9th Ed., Eds, Hardman, Limbird, Molinoff, Ruddon and Gilman, McGraw–Hill, New York, pp. 715–731, 1996.
Alami et al.. Tetrahedron Lett., 34, 6403, (1993).
Albini, A., Synthesis, 263 (1993).
Brenes–Pereira, C., Texas Heart Institute Journal, 24 (2), 118 (1997).
Burggraaf, J. et al., Clin. Sci., 86, 497 (1994).
Cabri et al., Tetrahedron Lett., 32, 1753 (1991).
Cash, J. D. et al., Brit J. Haematol, 27, 363 (1974).
Cecchi, L. et al., J. Het. Chem., 20, 871 (1983).
Coffen et al., J. Org. Chem., 49, 296 (1984).
Coppola et al., J. Het. Chem., 11, 51 (1974).
Craig et al., Tetrahedron Lett., 4025 (1979).
David, J–L., Regulatory Peptides, 45, 311 (1993).
du Vigneaud, V. et al., J. Am. Chem. Soc., 76, 4751 (1954).
Farina et al., J. Org. Chem., 59, 5905 (1994).
Hallstrom, et al., Tetrahedron Lett., 667 (1980).
Huguenin et al. Helv. Chim. Acta, 49, 695 (1966).
Inanaga et al., Bull. Chem. Soc. Jpn., 52, 1989 (1979).
Jones, R. A., Aldrichimica ACTA, 9(3), 35 (1976).
Kantlehner et al., Chem. Ber., 105, 1340 (1972).
Khuthier, A–H. et al., J. Chem. Soc. Chem. Commun., 9 (1979).
Klaubert, D. H., J. Het. Chem., 22, 333 (1985).
Knorr et al., J. Org. Chem., 49, 1288 (1984).
Kosugi et al., Bull. Chem. Soc. Jpn., 60, 767 (1987).
Lethagen, S., Ann. Hematol., 69, 173 (1994).
Ligouri et al., Tetrahedron, 44, 1255 (1988).
Lin et al., J. Het. Chem., 14, 345 (1977).
Manning et al., J. Med. Chem., 35, 3895 (1992).
Manning et al., J. Med. Chem., 35, 382 (1992).
Martina et al., Synthesis, 8, 613 (1991).
Martinez et al., J. Med. Chem., 35, 620 (1992).
Mayet et al., J. of the Royal College of Physicians of London, 31 (3), 313 (1997).
Murray R. W., Chem. Rev., 1187 (1989).
Oliver et al., J. Physiol. (London), 18, 277 (1895).
Reed et al., J. Org. Chem., 52, 3491 (1987).
Ruffolo et al., Drug News and Perspective, 4(4), 217 (May 1991).
Sonogashira et al., Tetrahedron Lett., 4467 (1975).
Street et al., J. Med. Chem., 36, 1529 (1993).
Williams, P. D., J. Med. Chem., 35, 3905 (1992).

* cited by examiner

Primary Examiner—Richard L. Raymond
Assistant Examiner—Brenda Coleman
(74) Attorney, Agent, or Firm—Steven R. Eck

(57) ABSTRACT

The present invention provides compounds of the general formula:

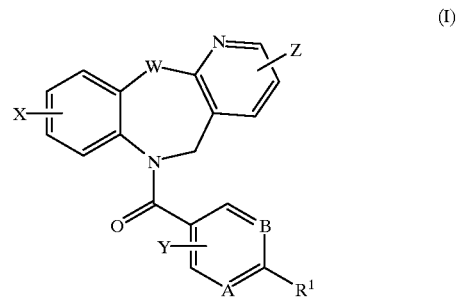

(I)

wherein W is O or NH, optionally substituted, as well as methods and pharmaceutical compositions utilizing these compounds for the treatment of disorder which may be remedied or alleviated by vasopressin agonist activity, including diabetes insipidus, nocturnal enuresis, nocturia, urinary incontinence, bleeding and coagulation disorders, or temporary delay of urination.

24 Claims, No Drawings

TRICYCLIC PYRIDO VASOPRESSIN AGONISTS

This application claims the benefit of U.S. Provisional Application No. 60/054,180, filed Jul. 30, 1997.

This invention concerns tricyclic pyrido compounds, or pharmaceutical salts thereof, which act as vasopressin agonists, as well as methods of treatment and pharmaceutical compositions utilizing the compounds.

BACKGROUND OF THE INVENTION

Vasopressin (antidiuretic hormone, ADH) a non-peptide hormone and neurotransmitter, is synthesized in the supraoptic nuclei of the hypothalamus of the brain and is transported through the supraoptico-hypophyseal tract to the posterior pituitary where it is stored. Upon sensing an increase in plasma osmolality by brain osmoreceptors or a decrease in blood volume or blood pressure (detected by the baroreceptors and volume receptors), vasopressin is released into the blood circulation and it activates $V_{1a}$ receptors on blood vessels causing vasoconstriction to raise blood pressure and vasopressin $V_2$ receptors of the nephron of the kidney causing retention mainly of water, and to a lesser degree electrolytes, to expand the blood volume (Cervoni and Chan, *Diuretic Agents*, in Kirk-Othmer, Encyclopedia of Chemical Technology, 4th ed., Wiley, volume 8, 398–432, (1993)). The existence of vasopressin in the pituitary was known as early as 1895 (Oliver and Schaefer, *J. Physiol. (London)*, 18, 277–279, (1895)). The determination of the structure and the total synthesis of vasopressin were accomplished by du Vigneaud and coworkers in 1954 (du Vigneaud, Gish and Katsoyannis, *J. Am. Chem. Soc.*, 76, 4751–4752, (1954)).

The actions of vasopressin $V_{1a}$ receptors are mediated through the phosphatidylinositol pathway. Activation of vasopressin $V_{1a}$ receptors causes contraction of the smooth muscle of the blood vessels to raise blood pressure. The actions of the vasopressin $V_2$ receptors are mediated through activation of the adenylate cyclase system and elevation of intracellular levels of cAMP. The activation of vasopressin $V_2$ receptors by vasopressin or vasopressin-like (peptidic or non-peptidic) compounds increases water permeability of the collecting ducts of the nephron and permits the reabsorption of a large quantity of free water. The end result is the formation and excretion of a concentrated urine, with a decrease in urine volume and an increase in urinary osmolality.

Vasopressin plays a vital role in the conservation of water by concentrating the urine at the site of the collecting ducts of the kidney. The collecting ducts of the kidney are relatively impermeable to water without the presence of vasopressin at the receptors and therefore, the hypotonic fluid formed after filtering through the glomeruli, passing the proximal convoluted tubule, the loops of Henle, and the distal convoluted tubules, will be excreted as dilute urine. However, during dehydration, volume depletion or blood loss, vasopressin is released from the brain and activates the vasopressin $V_2$ receptors in the collecting ducts of the kidney rendering the ducts very permeable to water; hence water is reabsorbed and a concentrated urine is excreted. In patients and animals with central or neurogenic diabetes insipidus, the synthesis of vasopressin in the brain is defective and therefore, they produce no or very little vasopressin, but their vasopressin receptors in the kidneys are normal. Because they cannot concentrate the urine, they may produce as much as 10 times the urine volumes of their healthy counterparts and they are very sensitive to the action of vasopressin and vasopressin $V_2$ agonists. Vasopressin and desmopressin, which is a peptide analog of the natural vasopressin, are being used in patients with central diabetes insipidus. Vasopressin $V_2$ agonists are also useful for the treatment of nocturnal enuresis, nocturia, urinary incontinence and temporary delay of urination whenever desirable.

Vasopressin, through activation of its $V_{1a}$ receptors, exerts vasoconstricting effects so as to raise blood pressure. A vasopressin $V_{1a}$ receptor antagonist will counteract this effect. Vasopressin and vasopressin agonists release factor VIII and von Willebrand factor so they are useful for the treatment of bleeding disorders, such as hemophilia. Vasopressin and vasopressin-like agonists also release tissue-type plasminogen activator (t-PA) into the blood circulation so they are useful in dissolving blood clots such as in patients with myocardial infarction and other thromboembolic disorders (Jackson, "Vasopressin and other agents affecting the renal conservation of water", in Goodman and Gilman, *The Pharmacological Basis of Therapeutics*, 9th ed., Hadman, Limbird, Molinoff, Ruddon and Gilman Eds., McGraw-Hill, New York, pp. 715–731 (1996); Lethagen, *Ann. Hematol.* 69, 173–180 (1994); Cash et al., *Brit. J. Haematol.*, 27, 363–364 (1974); David, *Regulatory Peptides*, 45, 311–317 (1993); Burggraaf et al., *Cli. Sci.*, 86, 497–503 (1994)).

The following prior art references describe peptidic vasopressin antagonists: Manning et al., *J. Med. Chem.*, 35, 382 (1992); Manning et al., *J. Med. Chem.*, 35, 3895 (1992); Gavras and Lammek, U.S. Pat. No. 5,070,187 (1991); Manning and Sawyer, U.S. Pat. No. 5,055,448 (1991); Ali, U.S. Pat. No. 4,766,108 (1988); Ruffolo et al., *Drug News and Perspectives* 4(4), 217 (May 1991). Williams et al., have reported on potent hexapeptide oxytocin antagonists [*J. Med. Chem.*, 35, 3905 (1992)] which also exhibit weak vasopressin antagonistic activity in binding to $V_1$ and $V_2$ receptors. Peptidic vasopressin antagonists suffer from a lack of oral activity and many of these peptides are non-selective antagonists since they also exhibit partial agonist activity.

Non-peptidic vasopressin antagonists have recently been disclosed. Albright et al. describe tricyclic diazepines as vasopressin and oxytocin antagonists in U.S. Pat. No. 5,516,774 (1996); tetrahydrobenzodiazepine derivatives as vasopressin antagonists are disclosed in J. P. 0801460-A (1996); Ogawa et al., disclose benzoheterocyclic derivatives as vasopressin and oxytocin antagonists, and as vasopressin agonists in WO 9534540-A; Albright et al., disclose tricyclic benzazepine derivatives as vasopressin antagonists in U.S. Pat. No. 5,512,563 (1996); and Venkatesan et al., disclose tricyclic benzazepine derivatives as vasopressin and oxytocin antagonists in U.S. Pat. No. 5,521,173 (1996).

As mentioned above, desmopressin (1-desamino-8-D-arginine vasopressin) (Huguenin and Boissonnas, *Helv. Chim. Acta*, 49, 695 (1966)) is a vasopressin agonist. The compound is a synthetic peptide with variable bioavailability. An intranasal route is poorly tolerated and an oral formulation for nocturnal enuresis requires a 10–20 fold greater dose than the intranasal administration.

The compounds of this invention are non-peptidic and have a good oral bioavailability. They are selective vasopressin $V_2$ agonists, and have no $V_{1a}$ agonist effects so they do not raise blood pressure. In contrast, the prior art compounds (except some in WO 9534540-A) are vasopressin antagonists.

SUMMARY OF THE INVENTION

This invention relates to novel compounds selected from those of Formula (I):

(I)

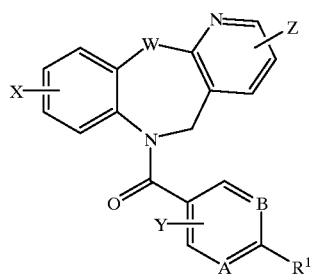

wherein:

W is O, or $NR^6$

A and B are, independently, carbon or nitrogen;

$R^1$ is —C≡C—$R^9$, alkanoyl of 2 to 7 carbon atoms or a moiety selected from the group of:

(a)
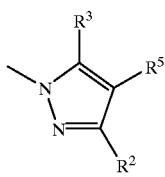

(b)
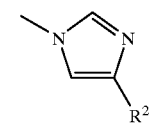

(c)
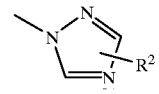

(d)
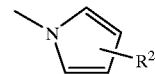

(e)
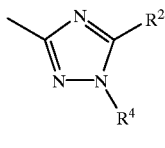

(f)
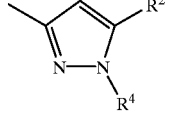

(g)
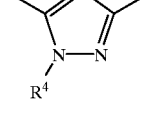

(h)
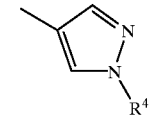

-continued (i)
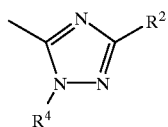

(j)
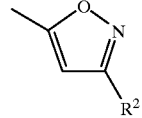

(k)
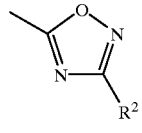

(l)
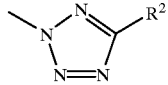

(m)
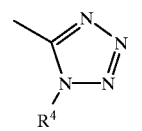

(n)
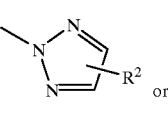

or (o)
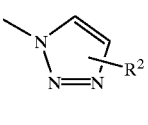

$R^2$, $R^3$ and $R^5$ are, independently, hydrogen, straight chain alkyl of 1 to 6 carbon atoms, branched chain alkyl of 3 to 7 carbon atoms, cycloalkyl of 3 to 7 carbon atoms, or perfluoroalkyl of 1 to 6 carbons;

$R^4$ is hydrogen, straight chain alkyl of 1 to 6 carbon atoms, branched chain alkyl of 3 to 7 carbon atoms, cycloalkyl of 3 to 7 carbon atoms, alkoxyalkyl of 2 to 7 carbon atoms, optionally substituted aralkyl of 7 to 12 carbon atoms, or an acyl substituent selected from the group consisting of alkanoyl of 2 to 7 carbon atoms, alkenoyl of 3 to 7 carbon atoms, cycloalkanoyl of 3 to 7 carbon atoms, arylalkanoyl having an alkane chain of from 1 to 6 carbon atoms, aroyl or heteroaroyl of 7 to 13 carbon atoms;

$R^6$ is hydrogen, acyl of 2 to 6 carbon atoms, straight chain alkyl of 1 to 6 carbon atoms, or branched chain alkyl of 3 to 7 carbon atoms;

X and Y are, independently, hydrogen, straight chain alkyl of 1 to 6 carbon atoms, branched chain alkyl of 3 to 7 carbon atoms, cycloalkyl of 3 to 7 carbon atoms, alkoxyalkyl of 2 to 7 carbon atoms, halogen, straight or branched chain alkoxy of 1 to 6 carbon atoms, hydroxy, $CF_3$, or perfluoroalkyl of 2 to 6 carbons;

Z is hydrogen or a straight chain alkyl group of 1 to 6 carbon atoms, branched chain alkyl of 3 to 7 carbon atoms, cycloalkyl of 3 to 7 carbon atoms, halogen, alkoxyalkyl of 2 to 7 carbons, or hydroxyalkyl of 1 to 6 carbons, or $CH_2NR^7R^8$;

$R^7$ and $R^8$ are, independently, hydrogen, straight chain alkyl of 1 to 6 carbon atoms, branched chain alkyl of 3 to 7 carbon atoms, aryl, or arylalkyl; or taken together with the nitrogen they form a five or six membered ring optionally containing one or more additional heteroatoms, preferably selected from N, S or O, such as $R^9$ is independently, hydrogen, a silyl containing group, or a lower alkyl of 1 to 6 carbons; and $R^{10}$ is a straight chain alkyl of 1 to 6 carbon atoms;

or a pharmaceutically acceptable salt, ester or prodrug form thereof.

Within the scope of this invention are subgeneric groups of the above mentioned compounds wherein W is O and A, B, X, Y, Z and $R^1$–$R^{10}$ are as defined above; and W is $NR^6$ and A, B, X, Y, Z and $R^1$–$R^{10}$ are as defined above.

Among the more preferred compounds of this invention are those selected from Formula (I):

(I)

wherein:

$R^1$ is alkanoyl of 2 to 7 carbon atoms or a moiety selected from the group of:

(a)

(b)

(e)

(f)

(g)

(h)

(i)

or (k)

$R^2$, $R^3$ and $R^5$ are, independently, hydrogen, straight chain alkyl of 1 to 6 carbon atoms, branched chain alkyl of 3 to 7 carbon atoms, cycloalkyl of 3 to 7 carbon atoms, or perfluoroalkyl of 1 to 6 carbons;

$R^4$ is hydrogen, straight chain alkyl of 1 to 6 carbon atoms, branched chain alkyl of 3 to 7 carbon atoms, cycloalkyl of 3 to 7 carbon atoms, alkoxyalkyl of 2 to 7 carbon atoms, optionally substituted aralkyl of 7 to 12 carbon atoms, or an acyl substituent selected from the group consisting of alkanoyl of 2 to 7 carbon atoms, alkenoyl of 3 to 7 carbon atoms, cycloalkanoyl of 3 to 7 carbon atoms, aroyl or heteroaroyl of 7 to 12 carbon atoms, optionally substituted with one or two alkyl groups of 1 to 6 carbon atoms, or arylalkanoyl of 1 to 6 carbon atoms;

$R^6$ is hydrogen, acyl of 2 to 6 carbon atoms, straight chain alkyl of 1 to 6 carbon atoms, or branched chain alkyl of 3 to 7 carbon atoms;

X and Y are, independently, hydrogen, straight chain alkyl of 1 to 6 carbon atoms, branched chain alkyl of 3 to 7 carbon atoms, cycloalkyl of 3 to 7 carbon atoms, alkoxyalkyl of 2 to 7 carbon atoms, halogen (including chlorine, bromine, fluorine, and iodine), straight chain
or branched chain alkoxy of 1 to 6 carbons, hydroxy,
CF$_3$, or perfluoroalkyl of 2 to 6 carbons;

Z is hydrogen or a straight chain alkyl group of 1 to 6
carbon atoms, branched chain alkyl of 3 to 7 carbon
atoms, cycloalkyl of 3 to 7 carbon atoms, halogen,
alkoxyalkyl of 2 to 7 carbons, hydroxyalkyl of 1 to 6
carbons, or CH$_2$NR$^7$R$^8$;

R$^7$ and R$^8$ are, independently, hydrogen, straight chain
alkyl of 1 to 6 carbon atoms, branched chain alkyl of 3
to 7 carbon atoms, aryl or arylalkyl; or taken together
with the nitrogen they form a five or six membered ring
optionally containing one or more additional
heteroatoms, preferably selected from N, S or O, most
preferably selected from N or O, such as

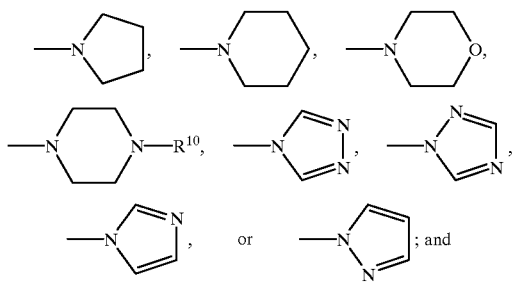

R$^8$ is a straight chain alkyl of 1 to 6 carbon atoms;
or a pharmaceutically acceptable salt, ester or prodrug form
thereof.

For the compounds defined above and referred to herein,
unless otherwise noted, aryl groups include, for example,
phenyl and naphthyl which can be substituted,
independently, with one or more substituents from the group
of hydrogen, halogen, cyano, straight chain alkyl of 1 to 6
carbon atoms, branched chain alkyl of 3 to 7 carbon atoms,
alkoxy of 1 to 6 carbons, CF$_3$, or phenyl, the phenyl
substituent being further optionally substituted with one or
more substituents selected from the group of hydrogen,
halogen, cyano, straight chain alkyl of 1 to 6 carbons,
branched chain alkyl of 3 to 7 carbons, or CF$_3$. The preferred
aryl groups herein are phenyl, biphenyl, and naphthyl,
substituted or unsubstituted.

For the compounds defined above and referred to herein,
unless otherwise noted, aroyl groups include, for example,
benzoyl and naphthoyl which can be substituted,
independently, with one or more substituents from the group
of hydrogen, halogen, cyano, straight chain alkyl of 1 to 6
carbon atoms, branched chain alkyl of 3 to 7 carbon atoms,
alkoxy of 1 to 6 carbons, CF$_3$, or phenyl, the phenyl
substituent being further optionally substituted with one or
more substituents selected from the group of hydrogen,
halogen, cyano, straight chain alkyl of 1 to 6 carbons,
branched chain alkyl of 3 to 7 carbons, or CF$_3$. The preferred
aroyl groups herein are benzoyl, (phenyl)benzoyl and
napthoyl, substituted or unsubstituted.

For the compounds defined above and referred to herein,
unless otherwise noted, heteroaroyl refers to a five or six
membered heterocyclic ring directly bonded to a carbonyl
radical, and containing one or two heteroatoms selected
from nitrogen, oxygen or sulfur, for example thiophene
carbonyl or pyridine carbonyl. The heteroaryl herein can be
substituted, independently, with one or more substituents
from the group of hydrogen, halogen, cyano, straight chain
alkyl of 1 to 6 carbon atoms, branched chain alkyl of 3 to 7
carbons, or CF$_3$.

For the compounds defined above and referred to herein,
unless otherwise noted, arylalkanoyl refers to groups such as
benzyl carbonyl or naphthylmethyl carbonyl containing an
alkyl group of 1 to 6 carbon atoms directly bonded to a
carbonyl radical, wherein the alkyl group is terminally
substituted by an aryl, and the aryl group is as defined
hereinbefore.

For the compounds defined above and referred to herein,
unless otherwise noted, aralkyl or arylalkyl refers to groups
such as benzyl or naphthylmethyl containing an alkyl
residue, preferably a lower alkyl residue of from 1 to 6
carbon atoms, most preferably from 1 to 3 carbon atoms,
terminally substituted by an aryl, wherein the aryl group is
as defined hereinbefore.

For the compounds defined above and referred to herein,
unless otherwise noted, the term halogen is meant to include
chlorine, bromine, fluorine and iodine.

The preferred compounds of this invention include:
[2-Chloro-4-(3-methyl-pyrazol-1-yl)-phenyl]-(5,11-
  dihydro-pyrido[2,3-b][1,5]benzodiazepin-6-yl)-
  methanone;
[2-Chloro-4-(5-methyl-pyrazol-1-yl)-phenyl]-(5,11-
  dihydro-pyrido[2,3-b][1,5]benzodiazepin-6-yl)-
  methanone;
[2-Bromo-4-(3-methyl-pyrazol-1-yl)-phenyl]-(5,11-
  dihydro-pyrido[2,3-b][1,5]benzodiazepin-10-yl)-
  methanone;
(5,11-Dihydro-pyrido[2,3-b][1,5]benzodiazepin-6-yl)-(4-
  fluoro-2-trifluoromethyl-phenyl)-methanone;
(5,11-Dihydro-pyrido[2,3-b][1,5]benzodiazepin-6-yl)-[4-
  (3-methyl-pyrazol-1-yl)-2-trifluoromethyl-phenyl]-
  methanone;
(5,11-Dihydro-pyrido[2,3-b][1,5]benzodiazepin-6-yl)-[4-
  (3-methyl-pyrazol-1-yl)-2-trifluoromethyl-phenyl]-
  methanone 1:1 salt with methanesulfonic acid;
(5,11-Dihydro-pyrido[2,3-b][1,5]benzodiazepin-6-yl)-[4-
  (3-methyl-pyrazol-1-yl)-2-trifluoromethyl-phenyl]-
  methanone 1:1 salt with hydrochloric acid;
4-(3-Methyl-pyrazol-1-yl)-2-trifluoromethyl-benzoic acid
  methylester;
4-(3-Methyl-pyrazol-1-yl)-2-trifluoromethyl-benzoic acid;
(5,11-Dihydro-pyrido[2,3-b][1,5]benzodiazepin-10-yl)-[4-
  (5-methyl-pyrazol-1-yl)-2-trifluoromethyl-phenyl]-
  methanone;
(5,11-Dihydro-pyrido[2,3-b][1,5]benzodiazepin-6-yl)-[2-
  trifluoromethyl-4-(3-trifluoromethyl-pyrazol-1-yl)-
  phenyl]-methanone;
(5-Methyl-5,11-dihydro-pyrido[2,3-b][1,5]benzodiazepin-
  10-yl)-[4-(3-methyl-pyrazol-1-yl)-2-trifluoromethyl-
  phenyl]-methanone;
(5,11-Dihydro-pyrido[2,3-b][1,5]benzodiazepin-10-yl)-[2-
  fluoro-4-(3-methyl-pyrazol-1-yl)-phenyl]-methanone;
(2,4-Difluoro-phenyl)-(5,11-dihydro-pyrido[2,3-b][1,5]
  benzodiazepin-10-yl)-methanone;
(5,11-Dihydro-pyrido[2,3-b][1,5]benzodiazepin-10-yl)-[4-
  fluoro-2-(3-methyl-pyrazol-1-yl)-phenyl]-methanone;
[2-Chloro-4-(3-methyl-pyrazol-1-yl)-phenyl]-(5-methyl-5,
  11-dihydro-pyrido[2,3-b][1,5]benzodiazepin-10-yl)-
  methanone;
(2-Chloro-4-fluoro-phenyl)-(5-methyl-5,11-dihydro-pyrido
  [2,3-b][1,5]benzodiaze pin-10-yl)-methanone;
(5,11-Dihydro-pyrido[2,3-b][1,5]benzodiazepin-10-yl)-[2-
  methyl-5-(3-methyl-pyrazol-1-yl)-phenyl]-methanone;
(5,11-Dihydro-pyrido[2,3-b][1,5]benzodiazepin-6-yl)-(5-
  fluoro-2-methyl-phenyl)-methanone;
[4-(3-tert-Butyl-pyrazol-1-yl)-2-trifluoromethyl-phenyl]-(5,
  11-dihydro-pyrido[2,3-b][1,5]benzodiazepin-10-yl)-
  methanone;

[2-Chloro-4-(3-methyl-pyrazol-1-yl)-phenyl]-(11H-5-oxa-4,10-diaza-dibenzo[a,d] cyclohepten-10-yl)-methanone;
[2-Chloro-4-(3-trifluoromethyl-pyrazol-1-yl)-phenyl]-(5,11-dihydro-pyrido[2,3-b][1,5]benzodiazepin-6-yl)-methanone;
[2-Chloro-4-(1-methyl-1H-pyrazol-3-yl)-phenyl]-(5,11-dihydro-pyrido[2,3-b][1,5]benzodiazepin-10-yl)-methanone;
[2-Chloro-4-(1-methyl-1H-pyrazol-3-yl)-phenyl]-(5-methyl-5,11-dihydro-pyrido[2,3-b][1,5]benzodiazepin-10-yl)-methanone;
6,11-Dihydro-5H-pyrido-[2,3-b][1,5]-benzodiazepine-5-one;
[2-Chloro-4-(5-methyl-1H-[1,2,4]triazol-3-yl)-phenyl]-(5,11-dihydro-pyrido[2,3-b][1,5]benzodiazepin-6-yl)-methanone;
[2-Bromo-4-(3-methyl-pyrazol-1-yl)-phenyl]-(11H-5-oxa-4,10-diazadibenzo[a,d] cyclohepten-10-yl)-methanone;
[4-(3-Methyl-pyrazol-1-yl)-2-trifluoromethyl-phenyl]-(11H-5-oxa-4,10-diazadibenzo[a,d] cyclohepten-10-yl)-methanone;
[2-Fluoro-4-(3-methyl-pyrazol-1-yl)-phenyl]-(11H-5-oxa-4,10-diazadibenzo[a,d] cyclohepten-10-yl)-methanone; and
[2-Chloro-4-(1-methyl-1H-pyrazol-3-yl)-phenyl]-(11H-5-oxa-4,10-diazadibenzo[a,d] cyclohepten-10-yl)-methanone.

It is understood by those practicing the art that some of the compounds of this invention depending on the definition of $R^2$, $R^3$, $R^4$, $R^5$, $R^6$, $R^7$, $R^8$, X, Y, and Z may contain one or more asymmetric centers and may thus give rise to optical isomers and diastereomers. The present invention includes such optical isomers and diastereomers; as well as the racemic and resolved, enantiomerically pure R and S stereoisomers; as well as other mixtures of the R and S stereoisomers and pharmaceutically acceptable salts thereof, which possess the indicated activity. Optical isomers may be obtained in pure form by standard procedures known to those skilled in the art. It is also understood that this invention encompasses all possible regioisomers, and mixtures thereof which possess the indicated activity. Such regioisomers may be obtained in pure form by standard separation procedures known to those skilled in the art.

The pharmaceutically acceptable salts are those derived from such organic and inorganic acids as: citric, lactic, acetic, tartaric, succinic, maleic, malonic, hydrochloric, hydrobromic, phosphoric, nitric, sulfuric, methanesulfonic, and similarly known acceptable acids.

Also according to the present invention there is provided a method of treating diseases, conditions or disorders in which vasopressin agonist activity is desired, the method comprising administering to a human or other mammal in need thereof an effective amount of a compound or a pharmaceutical composition of this invention. The present methods of treatment include those for diseases, conditions or disorders which make it desirable to release factor VIII and von Willebrand factor into the circulatory system, release tissue-type plasminogen activator (t-PA) in the blood circulation, or affect the renal conservation of water and urine concentration. Such methods of treatment include, but are not limited to, treatments for diabetes insipidus, nocturnal enuresis, nocturia, urinary incontinence, or bleeding and coagulation disorders in humans or other mammals.

The methods herein include facilitation in humans or other mammals of temporary delay of urination, which may also be described as controlling or treating the inability to temporarily delay urination, whenever desirable. This method is understood to include treatments facilitating the temporary delay of urination which are separate from and not included in the treatment of the conditions known as nocturnal enuresis and nocturia.

The present invention accordingly provides a pharmaceutical composition which comprises a compound of this invention in combination or association with a pharmaceutically acceptable carrier. In particular, the present invention provides a pharmaceutical composition which comprises an effective amount of a compound of this invention and a pharmaceutically acceptable carrier or excipient.

The compositions are preferably adapted for oral administration. However, they may be adapted for other modes of administration, for example, parenteral administration for patients suffering from heart failure.

In order to obtain consistency of administration, it is preferred that a composition of the invention is in the form of a unit dose. Suitable unit dose forms include tablets, capsules and powders in sachets or vials. Such unit dose forms may contain from 0.1 to 1000 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day. The compositions of the invention may be formulated with conventional excipients, such as a filler, a disintegrating agent, a binder, a lubricant, a flavoring agent and the like. They are formulated in conventional manner, for example, in a manner similar to that used for known antihypertensive agents, diuretics and β-blocking agents.

Also according to the present invention there are provided processes for producing the compounds of the present invention.

PROCESS OF THE INVENTION

The compounds of the present invention may be prepared according to one of the general processes outlined below. The compounds of general formula (I) wherein W is oxygen or $NR^6$ and $R^6$ is hydrogen, can be conveniently prepared as shown in Scheme I.

SCHEME I

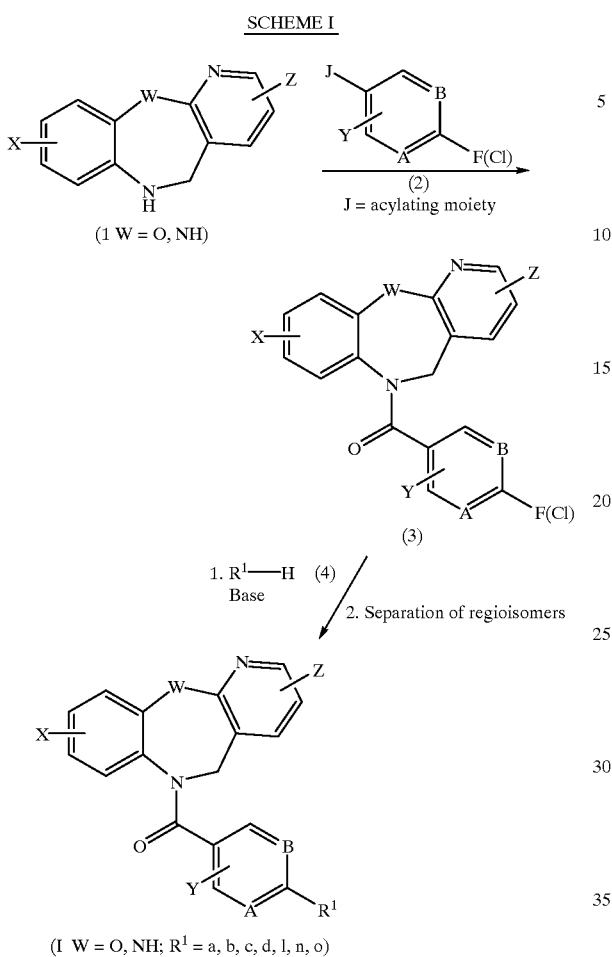

(I W = O, NH; R¹ = a, b, c, d, l, n, o)

Thus, a pyridobenzodiazepine (or benzoxazepine) of formula (1) is treated with an appropriately substituted haloaroyl(heteroaroyl) halide, preferably a fluoroaroyl or a fluoro(chloro)heteroaroyl chloride of formula (2, J=COCl), in the presence of an inorganic base such as potassium carbonate in a polar, aprotic solvent such as dimethylformamide; or an organic base such as 4-dimethylaminopyridine in an aprotic solvent such as dichloromethane or tetrahydrofuran at temperatures ranging from −40° C. to 50° C. to yield the intermediate acylated derivative (3).

Alternatively, the acylating species can be a mixed anhydride of the corresponding carboxylic acid, such as that prepared treating said acid with 2,4,6-trichlorobenzoyl chloride in an aprotic organic solvent such as dichloromethane according to the procedure of Inanaga et al., *Bull. Chem. Soc. Jpn.*, 52, 1989 (1979). Treatment of said mixed anhydride of general formula (2) with the pyridobenzodiazepine (or benzoxazepine) of formula (1) in a solvent such as dichloromethane and in the presence of an organic base such as 4-dimethylaminopyridine at temperatures ranging from 0° C. to the reflux temperature of the solvent, yields the intermediate acylated derivative (3) of Scheme I.

A compound of formula (3) is then treated with the sodium (potassium or lithium) salt of an appropriately substituted heterocycle of formula (4, wherein R¹ is selected from the a, b, c, d, l, n, or o group of heterocycles defined above) in an aprotic organic solvent such as dimethylformamide (or tetrahydrofuran) at temperatures ranging from ambient to the reflux temperature of the solvent, to yield a compound of general formula (I), wherein W is oxygen or NH, and A, B, X, Y, Z, R², R³, and R⁵ are as defined above, R⁶ is hydrogen, and R¹ is an heterocyclic moiety selected from the a, b, c, d, l, n or o group of heterocycles defined above and illustrated below.

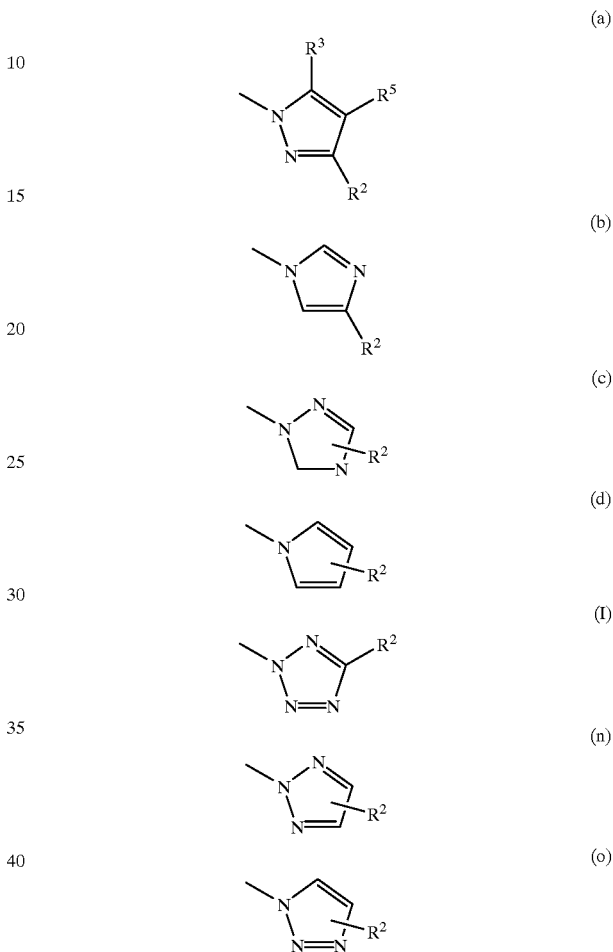

The condensation of the intermediate of formula (3) with the intermediate salt of formula (4) leads to a variable ratio of regioisomers of general formula (I) which are separated by means of chromatography and/or crystallization.

The preferred substituted fluoroaroyl and fluoro(chloro) heteroaroyl chlorides of formula (2) of Scheme I are either available commercially, or are known in the art, or can be readily prepared by procedures analogous to those in the literature for the known compounds.

The sodium (potassium or lithium) salts of the heterocycle of formula (4, wherein R¹ is selected from the a, b, c, d, l, n or o group of heterocycles defined above) of Scheme I are prepared by treatment of said heterocycle with a strong base such as sodium, potassium or lithium hydride or a metal alkoxide at temperatures ranging from −40° C. to ambient in an aprotic organic solvent such as dimethylformamide or tetrahydrofuran.

Alternatively, the compounds of general formula (I) described in Scheme I can be prepared according to the process outlined in Scheme II.

SCHEME II

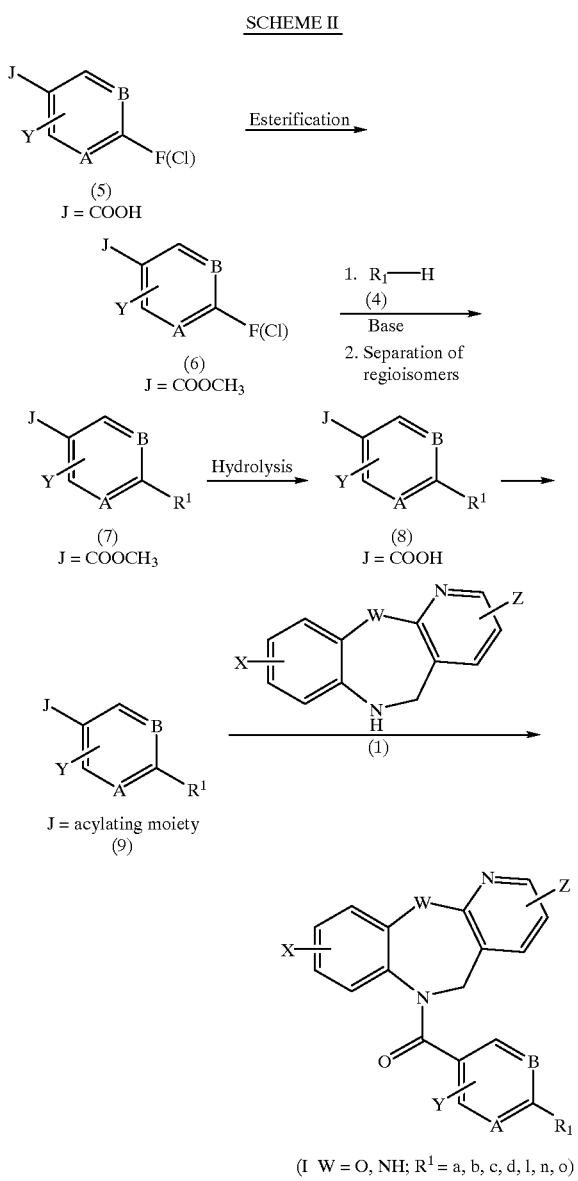

Thus, an appropriately substituted fluoroaryl or fluoro(chloro)heteroaryl carboxylic acid of formula (5) is esterified using methods known in the art, such as treatment with oxalyl chloride or thionyl chloride in an alcohol solvent such as methanol, in the presence of a catalytic amount of dimethylformamide; or by condensation with an alcohol such as methanol, in the presence of an acid catalyst such as para-toluenesulfonic acid at temperatures ranging from ambient to reflux temperature of the solvent.

The resulting ester of formula (6) is reacted with the sodium (potassium or lithium) salt of an appropriately substituted heterocycle of formula (4, wherein $R^1$ is selected from the a, b, c, d, l, n or o group of heterocycles defined above) in a polar aprotic organic solvent such as dimethylformamide at temperatures ranging from ambient to reflux temperature of the solvent, to yield an intermediate ester of general formula (7). The condensation of (6) with (4) leads to a variable ratio of regioisomers of general formula (7) which are separated by means of chromatography and/or crystallization.

Subsequent hydrolysis of the intermediate ester of formula (7) with an aqueous base such as sodium hydroxide in methanol (or lithium hydroxide in tetrahydrofuran) affords the carboxylic acid of general formula (8).

The intermediate carboxylic acid (8) is then converted into an acylating agent, preferably an acid chloride or a mixed anhydride of general formula (9) using any of the procedures described hereinbefore.

Subsequent condensation of the pyridobenzodiazepine (or benzoxazepine) of formula (1) with the intermediate acylating agent of formula (9) according to any of the procedures described hereinbefore, yields the desired compounds of formula (I) of Scheme I, wherein $R^1$ is selected from the a, b, c, d, l, n or o group of heterocycles defined above.

The appropriately substituted fluoroaryl or fluoro(chloro)heteroaryl carboxylic acids of formula (5) of Scheme II are either available commercially, or are known in the art, or can be readily prepared by procedures analogous to those in the literature for known compounds.

Alternatively, the substituted carboxylic acids of formula (8) of Scheme II can be prepared according to the process outlined in Scheme III.

SCHEME III

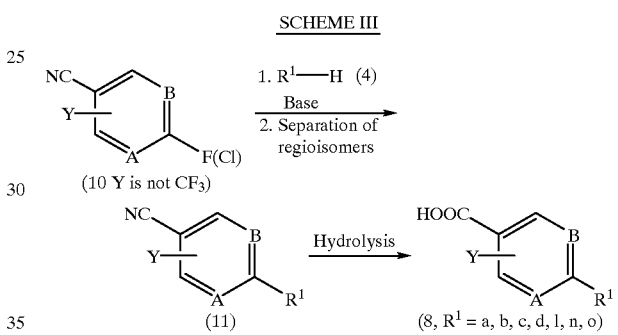

Thus, a fluoroaryl or fluoro(chloro)heteroaryl nitrile of formula (10) is reacted with the sodium (potassium or lithium) salt of an appropriately substituted heterocycle of formula (4, wherein $R^1$ is selected from the a, b, c, d, l, n or o group of heterocycles defined above) in a polar aprotic organic solvent such as dimethylformamide at temperatures ranging from ambient to the reflux temperature of the solvent, to yield an intermediate of general formula (11). Condensation of (10) with the intermediate (4) leads to a variable ratio of regioisomers of general formula (11) which are separated by means of chromatography and/or crystallization. Hydrolysis of the intermediate nitrile of formula (11, wherein Y is not $CF_3$) is preferentially carried out with an inorganic acid such as dilute sulfuric acid, at temperatures ranging from ambient to 60° C.

Alternatively, hydrolysis of the nitrile (11) can be carried out by heating in the presence of a strong alkaline base such as sodium hydroxide in an alcohol solvent such as ethanol, with or without a phase transfer catalyst such as benzyldimethyltetradecyl ammonium chloride.

The resulting carboxylic acid of formula (8) is then converted into the desired compounds of formula (I) of Scheme I (wherein $R^1$ is selected from the a, b, c, d, l, n and o group of heterocycles defined above) by procedures analogous to those described hereinbefore.

The appropriately substituted fluoroaryl or fluoro(chloro)heteroaryl nitrites of formula (10) of Scheme III are either available commercially, or are known in the art, or can be readily prepared by procedures analogous to those in the literature for known compounds.

Alternatively, the intermediate substituted carboxylic acids of formula (8, wherein $R^1$ is not b or d) of Scheme II can be prepared according to the process described in Scheme IV by sequential treatment of a nitrile of formula (11, wherein A and B are carbon, and $R^1$ is an heterocyclic moiety selected from the a, c, e, l, n and o, but not b or d group of heterocycles defined above) with basic hydrogen peroxide in dimethylsulfoxide essentially according to the procedure of Katritzky et al., *Synthesis*, 949 (1989); followed by hydrolysis of the resulting amides of formula (12) preferably by treatment with dilute sulfuric acid and sodium nitrite according to the procedure of Hales et al, *Tetrahedron*, 51, 7403 (1995).

SCHEME IV

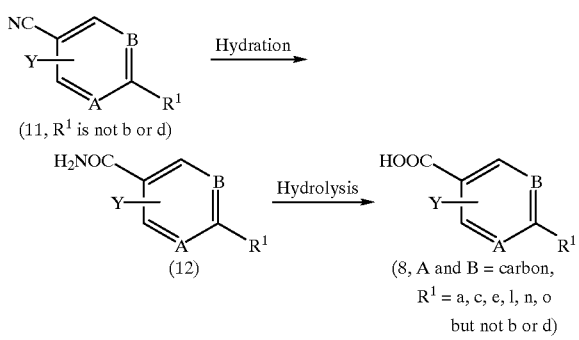

A preferred process for the preparation of the intermediate substituted carboxylic acids of formula (8) of Scheme II wherein $R^1$ is an heterocyclic moiety selected from the a group of $R^1$ heterocycles defined above, is outlined in Scheme V.

SCHEME V

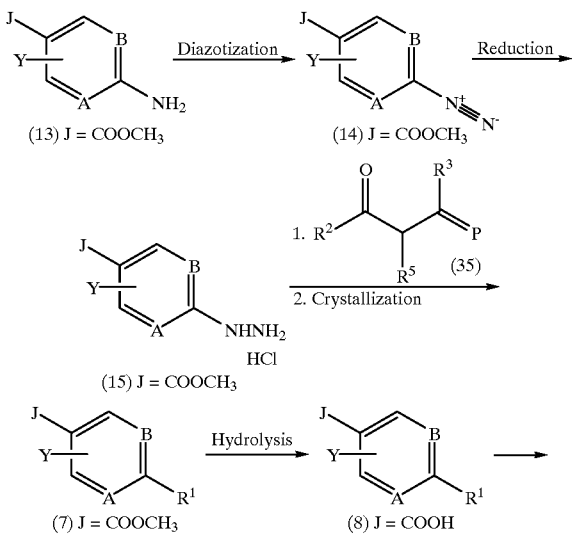

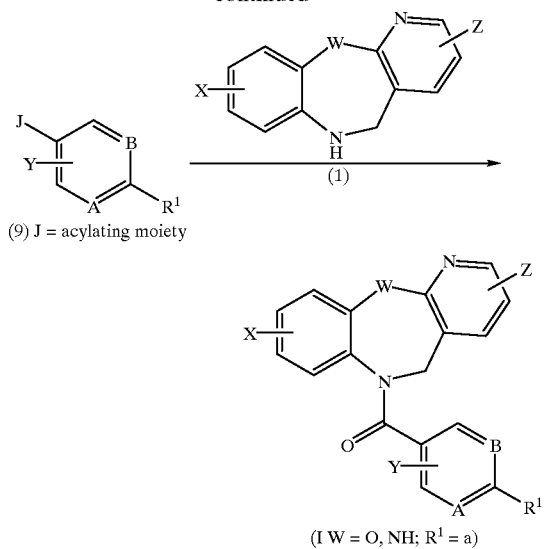

Thus, diazotization of an appropriately substituted aniline of general formula (13) followed by reduction of the resulting diazonium salt of formula (14) with tin (II) chloride in concentrated hydrochloric acid according to the procedure of Street et al., *J. Med. Chem.*, 36, 1529 (1993) provides the intermediate hydrazine hydrochloride salt of formula (15). Subsequent condensation of (15) with an aldehyde derivative of formula (35, wherein $R^2$ and $R^5$ are as defined above, $R^3$ is hydrogen, and P is a dialkylacetal) such as acetylacetaldehyde dimethyl acetal, or a ketone (or a ketone derivative) of formula (35, wherein $R^2$ and $R^5$ are as defined above, $R^3$ is not hydrogen, and P is O or a ketal) in a solvent such as aqueous methanol at temperatures ranging from ambient to 100° C. provides after crystallization, the desired intermediate ester of formula (7, wherein $R^1$ is selected from the a group of heterocycles defined above), which is then converted to the compound of formula (I, wherein $R^1$ is selected from the a group of heterocycles defined above and illustrated below) as outlined in Scheme II above (a)

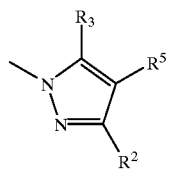

The compounds of general formula (I) wherein W is $NR^6$ and $R^6$ is other than hydrogen, and $R^1$ is selected from the a, b, c, d, l, n, or o group of heterocycles defined above, can be prepared by alkylation or acylation of the intermediate of formula (3, W=NH) of Scheme I, as outlined in Scheme VI.

SCHEME VI

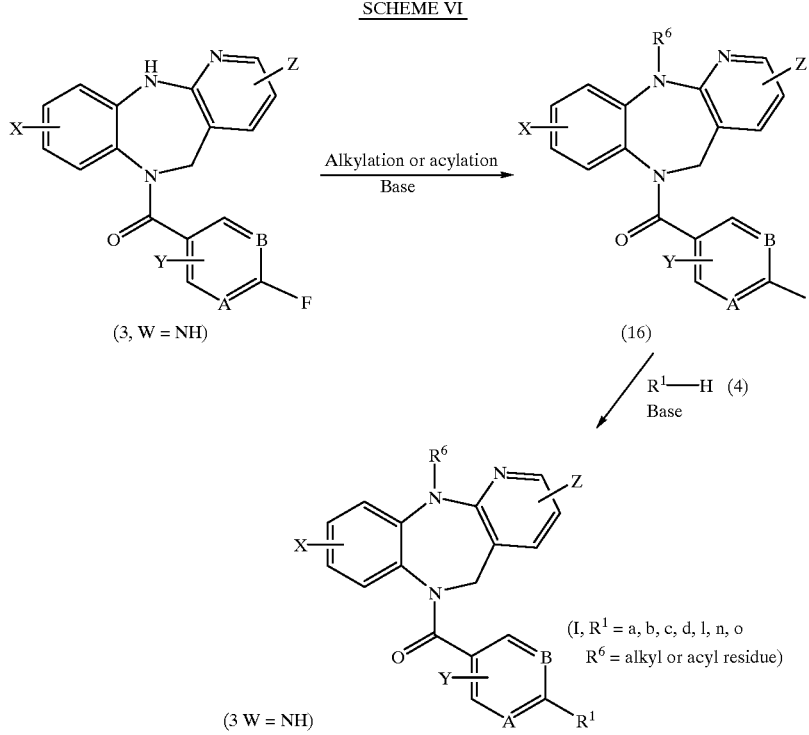

Thus, the intermediate compound (3, W=NH) of Scheme I is alkylated by treatment with a base such as sodium (or potassium) hydride and an alkylating agent such as an alkyl halide, preferably an alkyl chloride (bromide or iodide), in an aprotic solvent such as dimethylformamide or tetrahydrofuran at temperatures ranging from 0° C. to 80° C. to yield compounds of formula (16, wherein A, B, X, Y, Z, and $R^6$ are as defined above).

Alternatively, a compound of formula (3, W=NH) of Scheme I is acylated by treatment with a carboxylic acid halide or a carboxylic acid anhydride in the presence of an amine base such as pyridine or triethylamine in an aprotic solvent such as dichloromethane or with no addition of solvent when pyridine is used as the base, at temperatures ranging from −40° C. to ambient, to yield compounds of structure (16 wherein A, B, X, Y, Z, and $R^6$ are as defined above).

Subsequent treatment of the compounds of formula (16, wherein $R^6$ is either an alkyl or acyl moiety) with the sodium (potassium or lithium) salt of an appropriately substituted heterocycle of formula (4, wherein $R^1$ is selected from the a, b, c, d, l, n or o group of heterocycles defined above) in a polar aprotic organic solvent such as dimethylformamide at temperatures ranging from ambient to reflux temperature of the solvent, yields compounds of general formula (I), wherein W is $NR^6$, and $R^6$ is an alkyl or acyl residue; A, B, X, Y, Z, $R^2$, $R^3$, and $R^5$ are as defined above, and $R^1$ is an heterocyclic moiety selected from the group consisting of a, b, c, d, l, n or o, defined above and illustrated below.

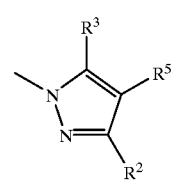

(a)

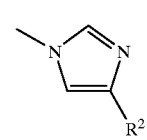

(b)

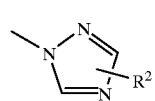

(c)

(d)

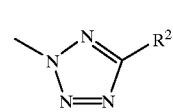

(l)

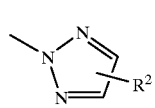

(n)

-continued

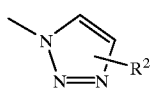
(o)

The alkylating and acylating agent(s) of Scheme VI are either available commercially, or are known in the art, or can be readily prepared by procedures analogous to those in the literature for known compounds.

Alternatively, a compound of general formula (I) of Scheme VI, can be prepared by a one-pot process outlined in Scheme VII.

SCHEME VII

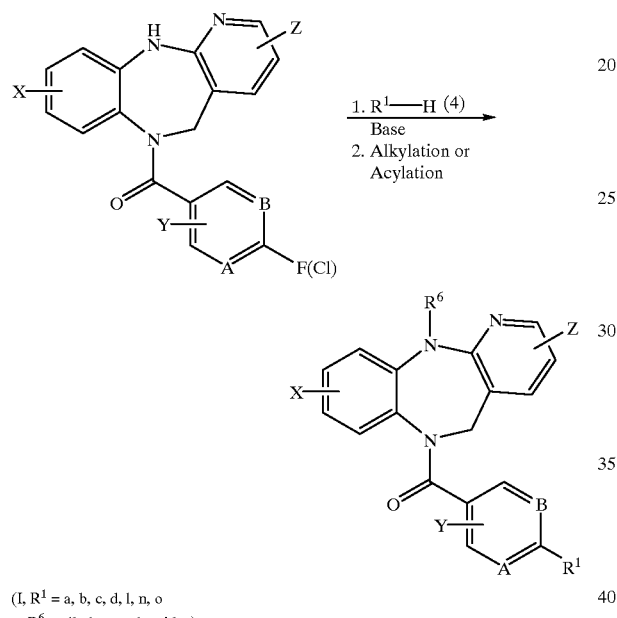

(I, $R^1$ = a, b, c, d, l, n, o
$R^6$ = alkyl or acyl residue)

Thus, a fluoroaryl or fluoro(chloro)heteroaryl intermediate of formula (3) of Scheme I (wherein W is NH) is reacted with the sodium (potassium or lithium) salt of an appropriately substituted heterocycle of formula (4, wherein $R^1$ is selected from the a, b, c, d, l, n or o group of heterocycles defined above) in a polar aprotic organic solvent such as dimethylformamide at temperatures ranging from ambient to the reflux temperature of the solvent, generating an intermediate of general formula (I, wherein W is NH) which without prior isolation, is further alkylated (or acylated) using the reaction conditions described hereinbefore to provide the desired compound of formula (I, wherein W is $NR^6$, and $R^6$ is an alkyl or acyl residue). This process leads also to a variable ratio of regioisomers of general formula (I), wherein W is $NR^6$, and $R^6$ is an alkyl or acyl residue; A, B, X, Y, Z, $R^2$, $R^3$, $R^4$ and $R^5$ are as defined above, and $R^1$ is an heterocyclic moiety defined as in Scheme VI. The regioisomers of formula (I) can be separated by means of chromatography and/or crystallization.

The compounds of general formula (I) of Scheme I wherein A and B are carbon, $R^2$ is hydrogen, and $R^1$ is an heterocyclic moiety selected from the g group of heterocycles described above, may be prepared according to the general process outlined in Scheme VIII.

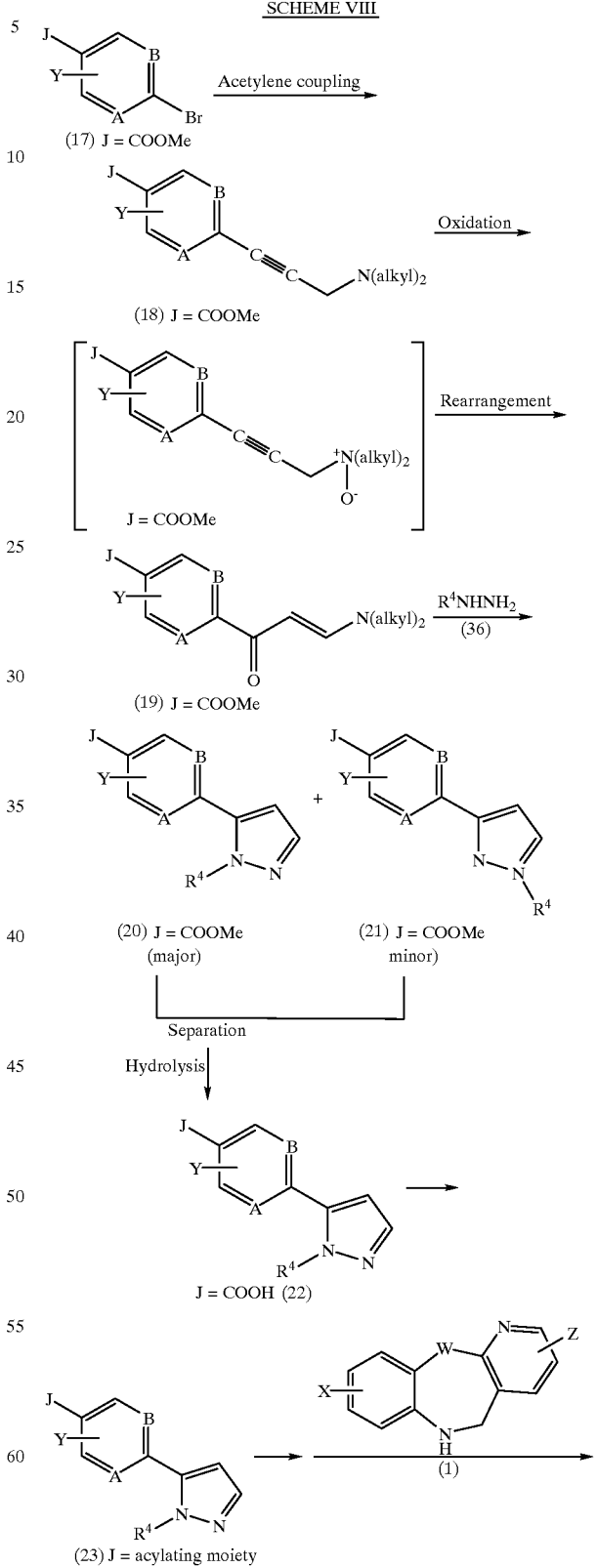

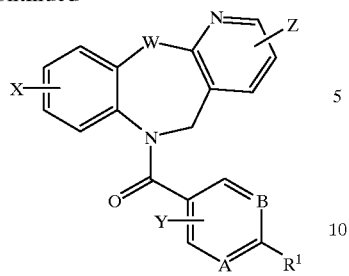

I (W = O, NH; A, B = carbon; $R^1$ = g)

Thus, an appropriately substituted haloaryl carboxylic acid ester, preferably a bromo (or iodo)phenyl methylester of formula (17, wherein A and B are carbon) is coupled with a dialkylamino propyne, in the presence of a catalyst such as bis(triphenylphosphine) palladium (II) chloride and copper (I) iodide in an organic base such as triethylamine as the solvent, and at temperatures ranging from ambient to 80° C. essentially according to the procedures of Alami et al., Tetrahedron Lett., 34, 6403 (1993), and of Sanogashira et al., Tetrahedron Lett., 4467 (1975), to provide the substituted acetylene intermediate of general formula (18).

The intermediate (18) is subsequently converted into its N-oxide by treatment with an oxidizing agent using any of a number of standard oxidative procedures (see Albini, Synthesis, 263, (1993)) or with a dioxirane reagent (see Murray, Chem. Rev., 1187 (1989)) in an aprotic organic solvent such as dichloromethane at temperatures below ambient. The intermediate N-oxide is not isolated but is rearranged in situ to an enone of general formula (19) by heating in a hydroxylic solvent such as methanol or by using any of the procedures of Dushin et al. This procedure provides a novel synthesis of enaminone compounds from propargylic amines (or their N-oxides) in hydroxylic solvents, which influence the ultimate outcome of the reaction. This new method of enaminone synthesis provides a convenient alternative to existing methods and further extends the range of starting materials that can be converted into enaminone products.

Although the precise mechanism by which a propargylic amine N-oxide is converted into an enaminone product has not been rigorously determined, it likely resembles two known processes; the thermal [2,3]-sigmatropic rearrangement of propargylic amine N-oxides (Craig, et al. Tetrahedron Lett., 4025, (1979); Hallstrom, et al., Tetrahedron Lett., 667, (1980); Khuthier, A-H, et al., J. Chem. Soc. Chem. Commun., 9, (1979) and the conversion of certain isoxazoles into enaminones (Liguori, et al., Tetrahedron, 44, 1255 (1988).

Treatment of (19) with a substituted hydrazine (36) in acetic acid at temperatures ranging from ambient to reflux leads to a mixture of regioisomeric compounds of general formulas (20) and (21) in a variable ratio. The major isomer of formula (20, wherein $R^2$ is H) is separated by means of chromatography and/or crystallization and is subsequently hydrolyzed to the desired carboxylic acid of formula (22).

The intermediate (22) is then converted into an acylating species, preferably an acid chloride (bromide or iodide) or a mixed anhydride of formula (23) by procedures analogous to those described hereinbefore. The acylating agent (23) is then used to acylate a pyridobenzodiazepine (or benzoxazepine) of formula (1) by any of the procedures described hereinbefore to yield the desired compound of formula (I), wherein W is O or NH, A and B are carbon, X, Y, Z, and $R^4$ are as defined above, $R^2$ is hydrogen, and $R^1$ is an heterocyclic moiety selected from the g group of heterocycles defined above and illustrated below.

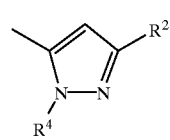

(g)

Likewise, treatment of (19) with an unsubstituted hydrazine (36, wherein $R^4$ is H) in acetic acid at temperatures ranging from ambient to the reflux temperature of the solvent yields the intermediate pyrazole ester of formula (24, $R^2$ and $R^4$ are H) as shown in Scheme IX. In this case the heterocyclic nitrogen of (24) can be alkylated or acylated to provide intermediates which can be converted to compounds of formula (I) wherein W is O or NH, A and B are carbon, X, Y, Z, and $R^4$ are as defined above, $R^2$ is hydrogen, and $R^1$ is an heterocyclic moiety selected from the f group of heterocycles defined above.

SCHEME IX

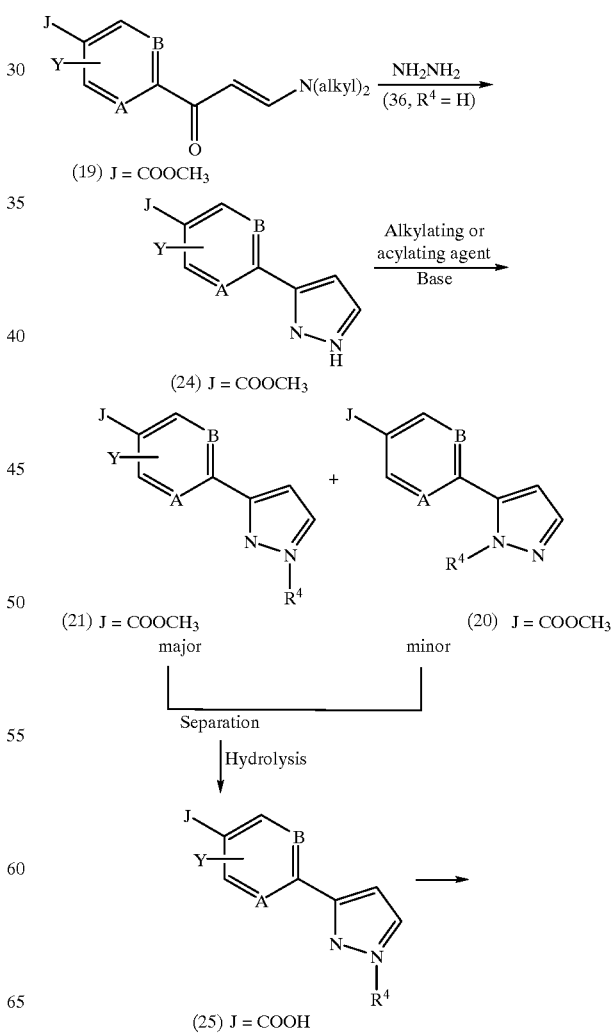

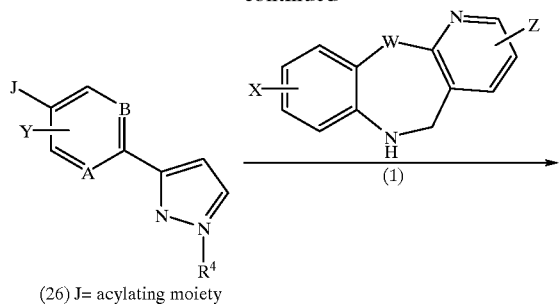

(26) J= acylating moiety

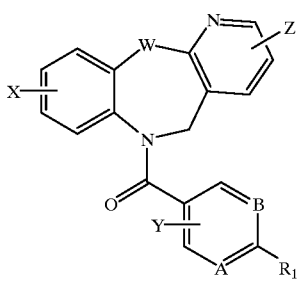

I (W = O, NH; A, B = carbon; $R^1$ = f)

Thus, the intermediate ester of formula (24, wherein $R^2$ is H, A and B are carbon) is alkylated by treatment with a base such as sodium or potassium hydride and an alkylating agent such as an alkyl halide, preferably an alkyl chloride (bromide or iodide) in an aprotic solvent such as dimethylformamide or tetrahydrofuran at temperatures ranging from 0° C. to 80° C. to yield a mixture of regioisomers of formulas (20) and (21) in a variable ratio. The major regioisomer of formula (21) is separated by chromatography and/or crystallization and is subsequently hydrolyzed to the desired carboxylic acid of formula (25), which is then converted to an acylating agent, preferably an acid chloride or a mixed anhydride by procedures analogous to those described hereinbefore. The acylating species of formula (26) is then used to acylate a pyridobenzodiazepine (or benzoxazepine) of formula (1) to yield the desired compound of formula (I), wherein W is O or NH, A and B are carbon, X, Y, Z, and $R^4$ are as defined above, $R^2$ is hydrogen, and $R^1$ is an heterocyclic moiety selected from the f group of heterocycles defined above and illustrated below.

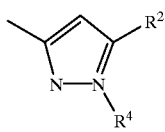
(f)

Compounds of general formula (I) wherein W=is O or NH, A and B are carbon, and $R^1$ is an heterocyclic moiety selected from the h group of heterocycles defined above, can be prepared as outlined in Scheme X.

SCHEME X

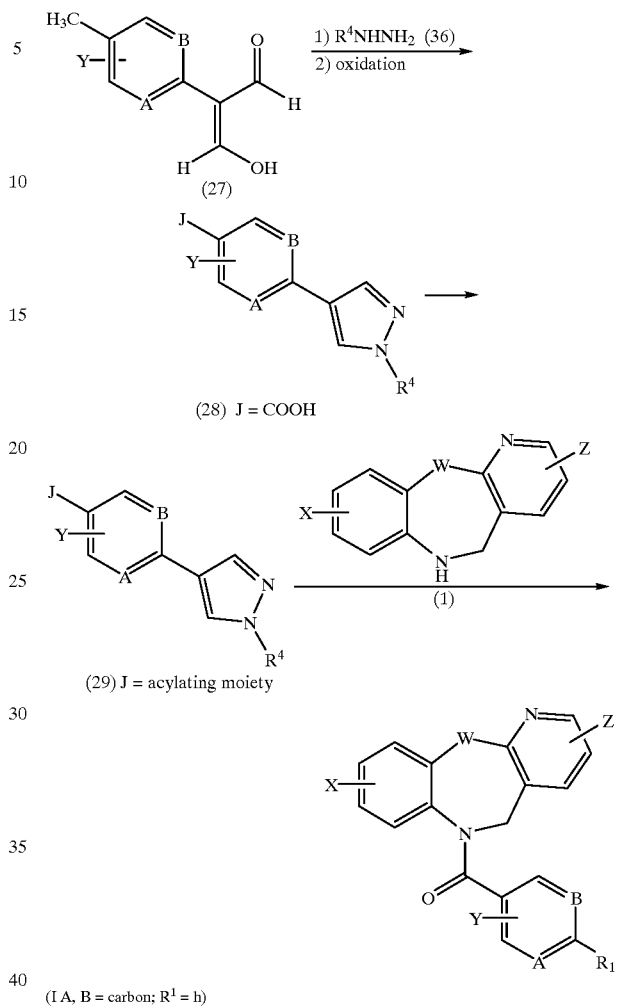

(I A, B = carbon; $R^1$ = h)

An appropriately substituted malondialdehyde of formula (27) is treated first with a hydrazine in acetic acid at temperatures ranging from ambient to the reflux temperature of the solvent and the intermediate pyrazole is oxidized preferably with potassium permanganate in a basic aqueous solution at temperatures ranging from ambient to the reflux temperature of the solvent to yield a carboxylic acid intermediate of formula (28). The acid (28) is converted into an acylating agent, preferably an acid chloride (bromide or iodide) or a mixed anhydride by procedures analogous to those described hereinbefore. The acylating agent of formula (29) is finally reacted with a pyridobenzodiazepine (or benzoxazepine) of formula (1) to yield compounds of general formula (I) wherein W is O or NH, A and B are carbon, X, Y, Z, and $R^4$ are as defined above, and $R^1$ is an heterocyclic moiety selected from the h group of heterocycles defined above and illustrated below.

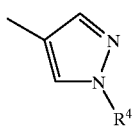

(h)

The preferred malondialdehydes of formula (27) and the hydrazines (36) of Scheme X are either available commercially, or are known in the art, or can be readily prepared by procedures analogous to those in the literature for known compounds, such as those of Knorr et al., *J. Org. Chem.*, 49, 1288 (1984) and Coppola et al., *J. Het. Chem.*, 51 (1974).

An alternative preparation of the intermediate carboxylic acids of formula (28) of Scheme X wherein Y is as defined above and $R^4$ is other than hydrogen, is outlined in Scheme XI.

SCHEME XI

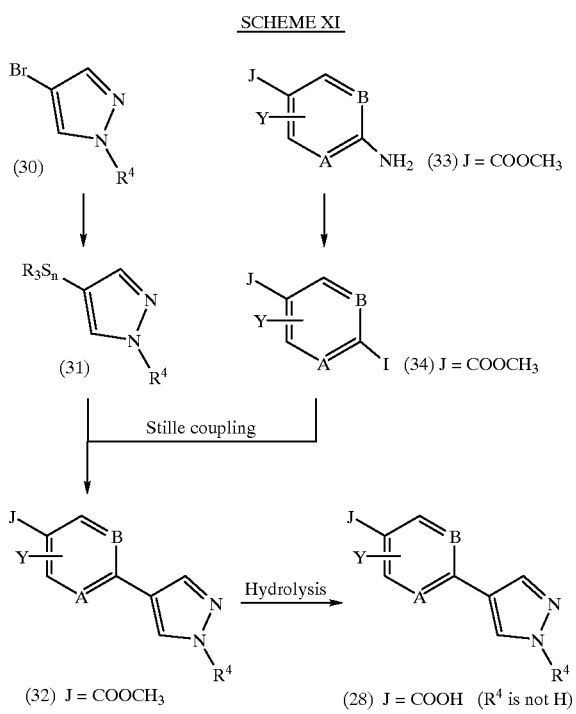

An organotin reagent of formula (31) is reacted in a Stille coupling reaction with an appropriately substituted aryl (heteroaryl) halide, preferably a bromide (or iodide) of formula (34) in the presence of a catalyst such as tetrakis (triphenylphosphine) palladium (0) and copper (I) iodide in an organic aprotic solvent such as dimethylformamide at temperatures ranging from ambient to 150° C., essentially according to procedures analogous to those of Farina et al., *J. Org. Chem.*, 59, 5905 (1994). Basic hydrolysis of the resulting ester of formula (32) with sodium hydroxide in aqueous alcohol or lithium hydroxide in aqueous tetrahydrofuran at temperatures ranging from ambient to the reflux temperature of the solvent yields the desired carboxylic acids of formula (28) of Scheme X.

In turn, the organotin reagents of formula (31) of Scheme XI wherein R is preferably an alkyl group, are conveniently prepared by metallation of a 4-bromo-N-alkylpyrazole of formula (30) with a trialkyltin halide, preferably a tributyltin chloride (or bromide) in the presence of a metallating agent such as n-butyl lithium in an aprotic organic solvent such as diethyl ether at temperatures ranging from −40° C. to ambient according to procedures analogous to those found in Martina et al., *Synthesis*, 8, 613 (1991).

The preferred N-alkyl substituted pyrazoles of formula (30) of Scheme XI are conveniently prepared from a 4-bromopyrazole by alkylation with an alkyl halide, preferably an alkyl chloride (bromide or iodide) in the presence of a base such as sodium (or potassium) hydride in an aprotic organic solvent such as dimethylformamide or tetrahydrofuran at temperatures ranging from 0° C. to 80° C. Alternatively, alkylation of the 4-bromopyrazole can be carried out with an alkylating agent mentioned above, and a strong alkaline base such as sodium hydroxide in the presence of a phase transfer catalyst, such as benzyldimethyltetradecyl ammonium chloride or benzyltrimethylammonium chloride (see Jones, *Aldrichimica Acta*, 9, 35 (1976)).

The preferred aryl (heteroaryl) iodides of formula (34) of Scheme XI are conveniently prepared by diazotization of the corresponding substituted anilines of formula (33) followed by reaction of the corresponding diazonium salt with iodine and potassium iodide in aqueous acidic medium essentially according to the procedures of Street et al., *J. Med. Chem.*, 36, 1529 (1993) and of Coffen et al., *J. Org. Chem.*, 49, 296 (1984).

The compounds of general formula (I) may be prepared also according to one of the general processes outlined below.

As shown in Scheme XII, a pyridobenzodiazepine (or benzoxazepine) of formula (1) is treated with an appropriately substituted acetylaroyl (heteroaroyl)halide preferably an acetylaroyl (heteroaroyl)chloride of formula (37, J=COCl) according to any of the procedures described hereinbefore, to yield the acylated derivative of formula (38). Treatment of (38) with a dialkylamide dialkylacetal such as a dimethylamide dimethyl acetal of formula (39, where alkyl is $CH_3$), in an aprotic organic solvent such as dichloromethane at temperatures ranging from 0° C. to the reflux temperature of the solvent according to the procedure of Lin et al., *J. Het. Chem.*, 345 (1977) yields the enone of formula (40). Treatment of (40) with hydroxylamine or a substituted hydrazine of formula (36) in acetic acid at temperatures ranging from ambient to the reflux temperature of the solvent provides the target compounds of formula (I) wherein W is O or NH, A, B, X, Y, Z, $R^2$ and $R^4$ are as defined above, and $R^1$ is an heterocyclic moiety selected from the f, g, or j group of heterocycles defined above and illustrated below.

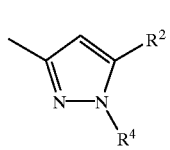

(f)

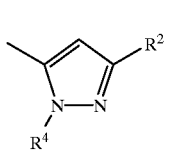

(g)

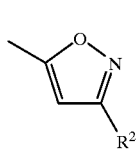

(j)

The preferred substituted acetylaroyl (heteroaroyl) chlorides of formula (37) of Scheme XII are conveniently prepared by treating the corresponding carboxylic acids with thionyl chloride at temperatures ranging from ambient to the reflux temperature of the solvent, or with oxalyl chloride in an aprotic solvent such as dichloromethane or tetrahydrofuran in the presence of a catalytic amount of dimethylformamide at temperatures ranging from 0° C. to 40° C.

The preferred dialkylamide dialkylacetals of formula (39) of Scheme XII are either available commercially, or are known in the literature, or can be conveniently prepared according to procedures analogous to those in the literature for the known compounds (see Kantlehner, *Chem. Ber.*, 105, 1340 (1972).

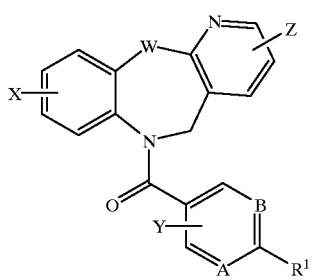

(I $R^1$ = f, g, j)

An alternate process for the preparation of intermediates of formula (38) of Scheme XII is illustrated in the following Scheme XIII.

SCHEME XII

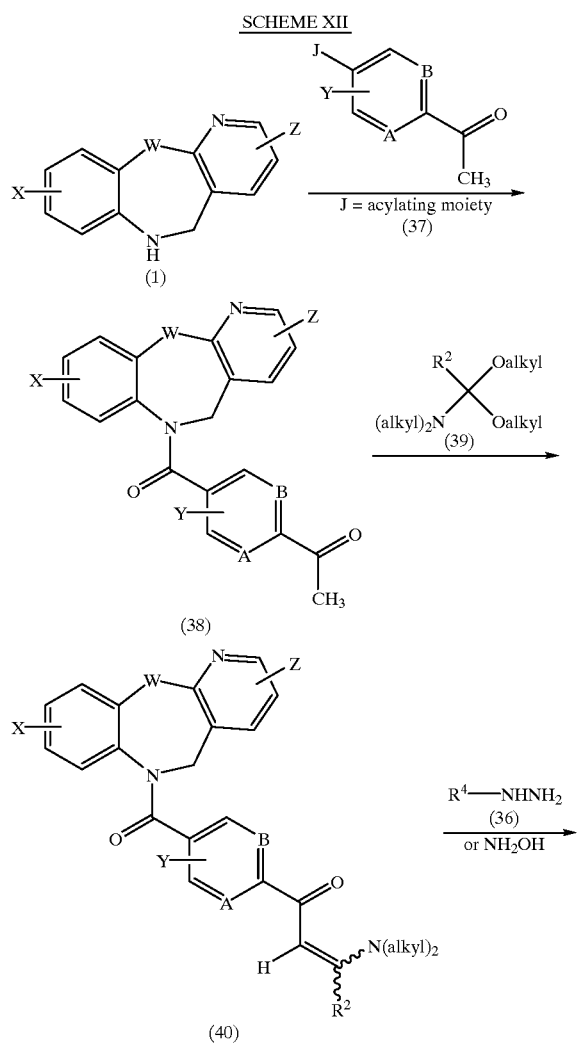

SCHEME XIII

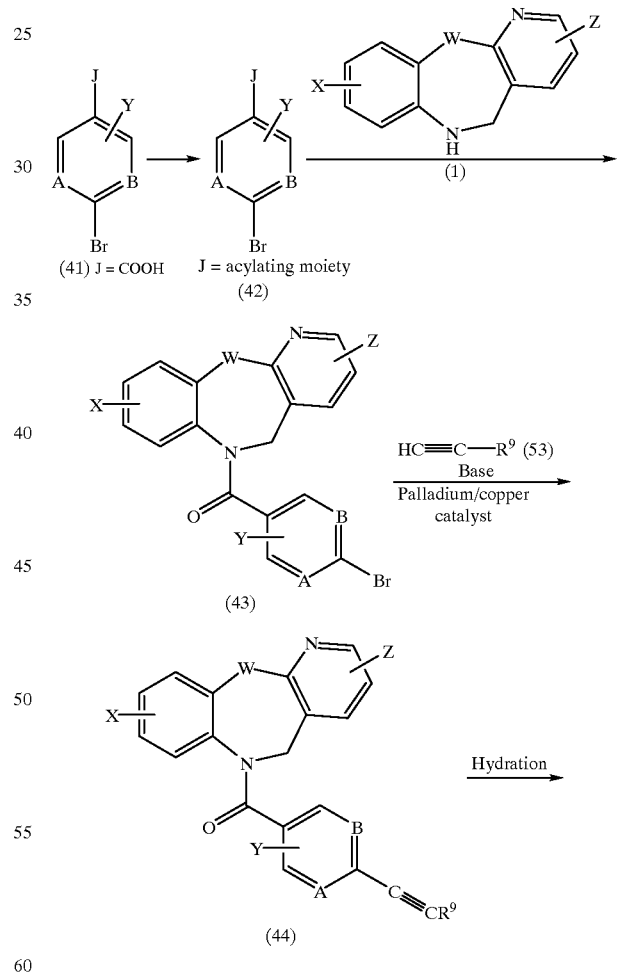

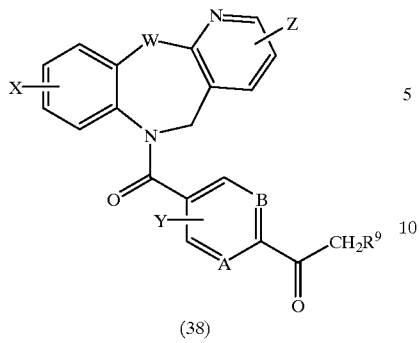

(38)

Scheme XIV

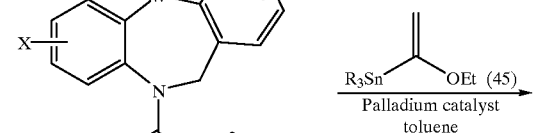

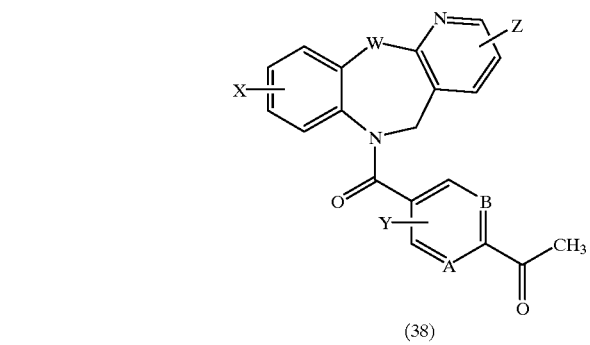

(38)

Thus, a pyridobenzodiazepine (or benzoxazepine) of formula (1) is treated with an appropriately substituted bromoaroyl(heteroaroyl) halide, preferably a bromoaroyl (heteroaroyl) chloride of formula (42) according to any of the procedures described hereinbefore, to yield the acylated intermediate of formula (43). The intermediate (43) is subsequently coupled with a monosubstituted acetylene of formula (53, wherein $R^9$ is preferably trimethylsilyl or lower alkyl of 1 to 6 carbon atoms) in the presence of pyridine and a catalyst such as bis(triphenylphosphine) palladium (II) chloride and copper (I) iodide in an organic base such as triethylamine as the solvent, in a sealed pressure tube at temperatures ranging from ambient to 100° C. essentially according to the procedure of Martinez et al., *J. Med. Chem.*, 52, 3491 (1987). The resulting acetylene intermediate of formula (44) is then hydrated by treatment with 1% sulfuric acid in an aprotic organic solvent such as tetrahydrofuran saturated with mercury (II) sulfate at ambient temperature essentially according to the procedure of Reed et al, *J. Org. Chem.*, 52, 3491 (1987) to provide the desired acyl compound of formula (38) wherein W is O or NH, and A, B, X, Y, and Z are as defined above, and $R^9$ is hydrogen or lower alkyl of 1 to 6 carbon atoms.

Alternatively, compound (44) where $R^9$ is trimethylsilyl is treated with n-tetrabutylammonium fluoride in an ether solvent such as tetrahydrofuran, to afford compound (44) where $R^9$ is hydrogen.

The preferred acylating agents of formula (42) of Scheme XIII are conveniently prepared by treating an appropriately substituted aryl(heteroaryl) carboxylic acid of formula (41) with thionyl chloride at temperatures ranging from ambient to the reflux temperature of the solvent, or with oxalyl chloride in an aprotic solvent such as dichloromethane or tetrahydrofuran in the presence of a catalytic amount of dimethylformamide at temperatures ranging from 0° C. to 40° C.

The acetylene intermediates (53) of Scheme XIII are either available commercially, or are known in the art, or can be readily prepared by procedures analogous to those in the literature for the known compounds.

As shown in Scheme XIV, the intermediate acetyl compounds (38) of Scheme XII can be prepared also by the Stille coupling of a bromo aryl (heteroaryl) compound of formula (43) of Scheme XIII with an (α-alkoxyvinyl)trialkyltin preferably an (α-ethoxyvinyl)tributyltin of formula (45), in the presence of a catalytic amount of bis (triphenylphosphine) palladium (II) chloride in an aprotic organic solvent such as toluene at temperatures ranging from ambient to the reflux temperature of the solvent, essentially according to the procedure of Kosugi et al., *Bull Chem. Soc. Jpn.*, 60, 767 (1987).

The preparation of the acetyl compound (38) can also be accomplished via the palladium-catalyzed arylation of a vinyl alkylether such as vinyl butylether, with the aryl halide intermediate of formula (43) according to the procedure of Cabri et al., *Tetrahedron Lett.*, 32, 1753 (1991).

The (α-alkoxyvinyl)trialkyltin intermediates (45) of Scheme XIV are either available commercially, or are known in the art, or can be readily prepared by procedures analogous to those in the literature for the known compounds.

Compounds in which $R^1$ contains three heteroatoms are prepared according to Scheme XV.

SCHEME XV

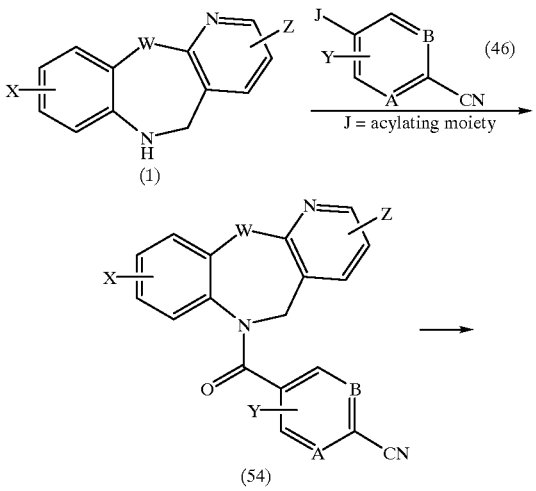

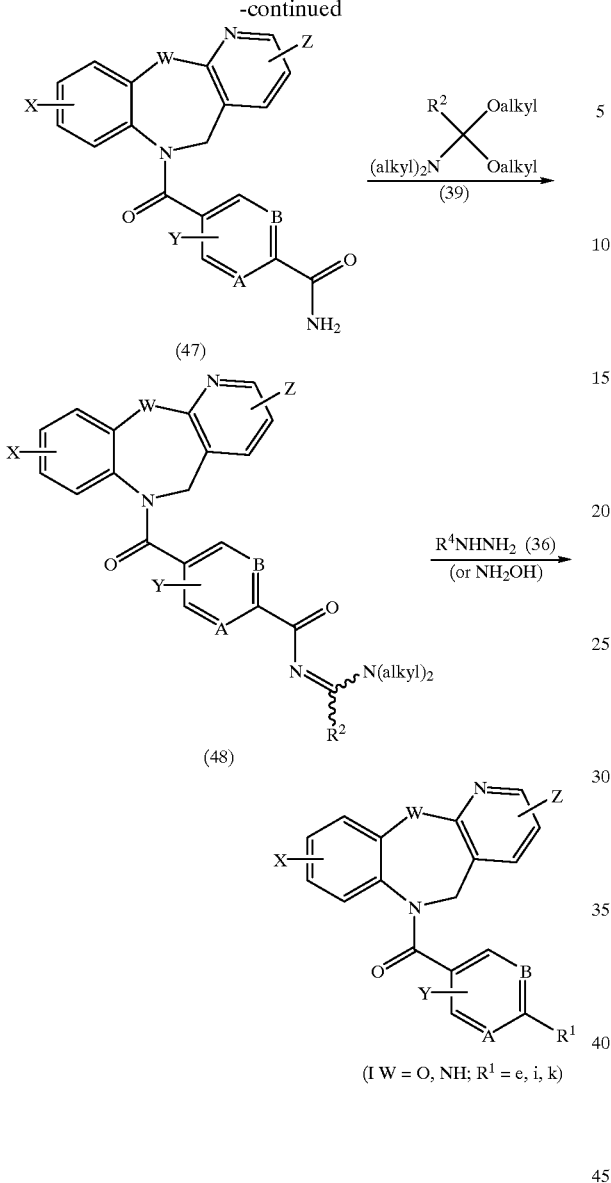

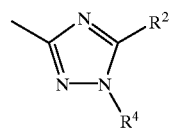
(e)

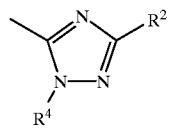
(i)

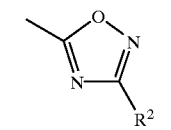
(k)

Another preferred process for the preparation of the intermediate amide of formula (47, where A, B are carbon) of Scheme XV is outlined in Scheme XVI. An appropriately substituted aryl nitrile of formula (49, A and B are carbon) is hydrated with basic hydrogen peroxide in dimethylsulfoxide essentially according to the procedure of Katritzky et al., *Synthesis*, 949 (1989), to provide the intermediate amide (50). Subsequent hydrolysis of the ester moiety gives the carboxylic acid intermediate (51) which is then converted into the acylating species of formula (52) by using any of the procedures described hereinbefore. Treatment of a pyridobenzazepine (or benzoxazepine) of formula (1) with (52) using any of the procedures described hereinbefore provides the desired intermediate amide (47, where A and B are carbon).

SCHEME XVI

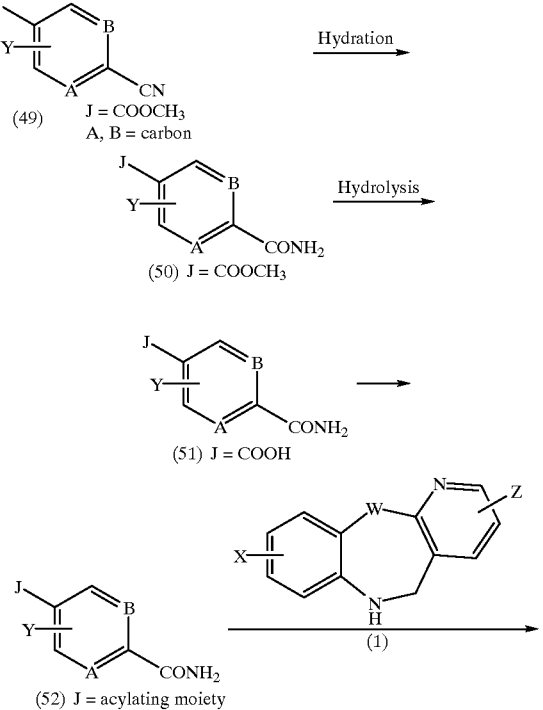

Thus, a pyridobenzodiazepine (or benzoxazepine) of formula (1) is treated with an appropriately substituted cyanoaroyl (heteroaroyl) halide, preferably a cyanoaroyl (heteroaroyl) chloride of formula (46) according to any of the procedures described hereinbefore, to yield an intermediate nitrile of formula (54) which in turn, is converted to an amide intermediate of general formula (47) by treatment with an inorganic acid such as sulfuric acid at temperatures ranging from ambient to 50° C. Treatment of the amide (47) with a dialkylamide dialkylacetal such as a dimethylamide dimethylacetal of formula (39, wherein alkyl is $CH_3$) in an aprotic organic solvent such as dichloromethane or tetrahydrofuran at temperatures ranging from 0° C. to 80° C. yields the intermediate of formula (48). Treatment of (48) with hydroxylamine or a hydrazine of formula (36) in acetic acid at temperatures ranging from ambient to reflux yields the desired target compounds of formula (I) wherein W is O or NH, A, B, X, Y, Z, $R^2$ and $R^4$ are as defined above, and $R^1$ is an heterocyclic moiety selected from the e, i or k group of heterocycles defined above and illustrated below.

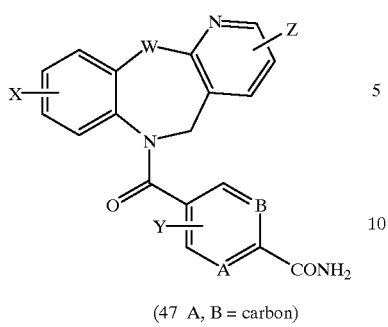

(47 A, B = carbon)

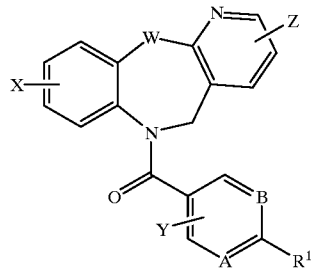

(I, W = O or NH, R1 = e, i, and R4 is not H)

Another preferred process to prepare compounds of general formula (I) of Scheme XV where W is O or NH, $R^1$ is an heterocyclic moiety selected from the e or i group of heterocycles defined above, and $R^4$ is not hydrogen, is shown in Scheme XVII.

SCHEME XVII

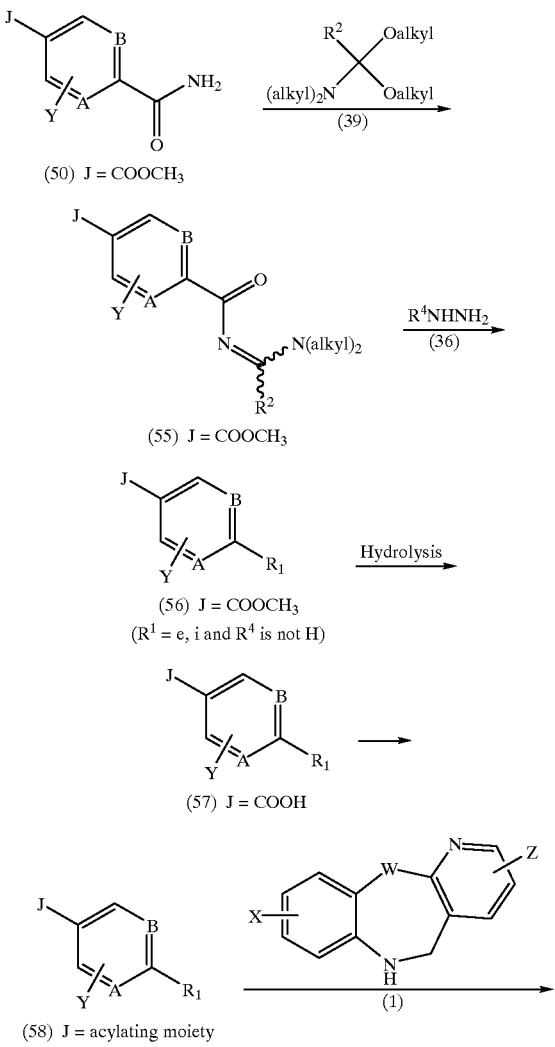

Thus, an appropriately substituted amide of formula (50) of Scheme XVI is treated with a dialkylamide dialkylacetal such as a dimethylamide dimethylacetal of formula (39, where alkyl is $CH_3$) at temperatures ranging from 0° C. to 100° C. to provide the intermediate of formula (55). Treatment of (55) with a substituted hydrazine of formula (36) in acetic acid at temperatures ranging from ambient to reflux, yields the desired intermediate triazole ester of formula (56). The ester (56) is subsequently hydrolyzed to the carboxylic acid of formula (57, wherein $R^1$ is an heterocyclic moiety selected from the e or i group of heterocycles defined above, and $R^4$ is not hydrogen) which is then converted to an acylating agent, preferably an acid chloride or a mixed anhydride of formula (58) by procedures analogous to those described hereinbefore. The acylating species (58) is used to acylate a pyridobenzodiazepine (or benzoxazepine) of formula (1) to yield the desired compound of formula (I) wherein W is O or NH, A, B, X, Y, Z and $R^2$ are as defined above, $R^1$ is an heterocyclic moiety selected from the e and i group of heterocycles defined above and illustrated below, and $R^4$ is not hydrogen.

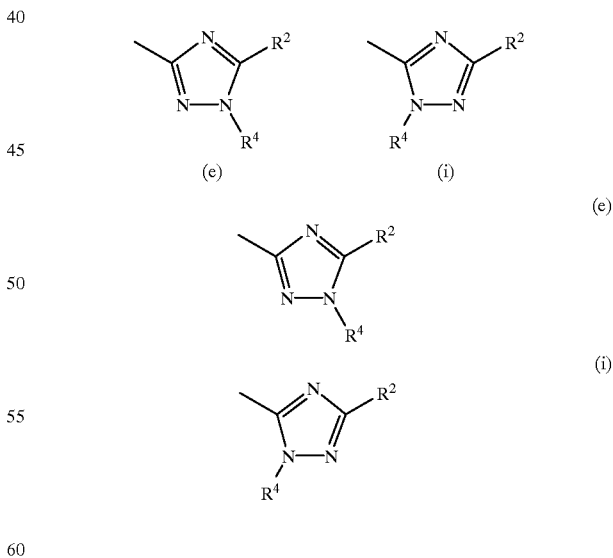

Alternatively, the compounds of general formula (I) of Scheme XV wherein W is O or NH, $R^1$ is an heterocyclic moiety selected from the e or i group of heterocycles defined above, and $R^4$ is not hydrogen can be prepared as illustrated in Scheme XVIII.

SCHEME XVIII

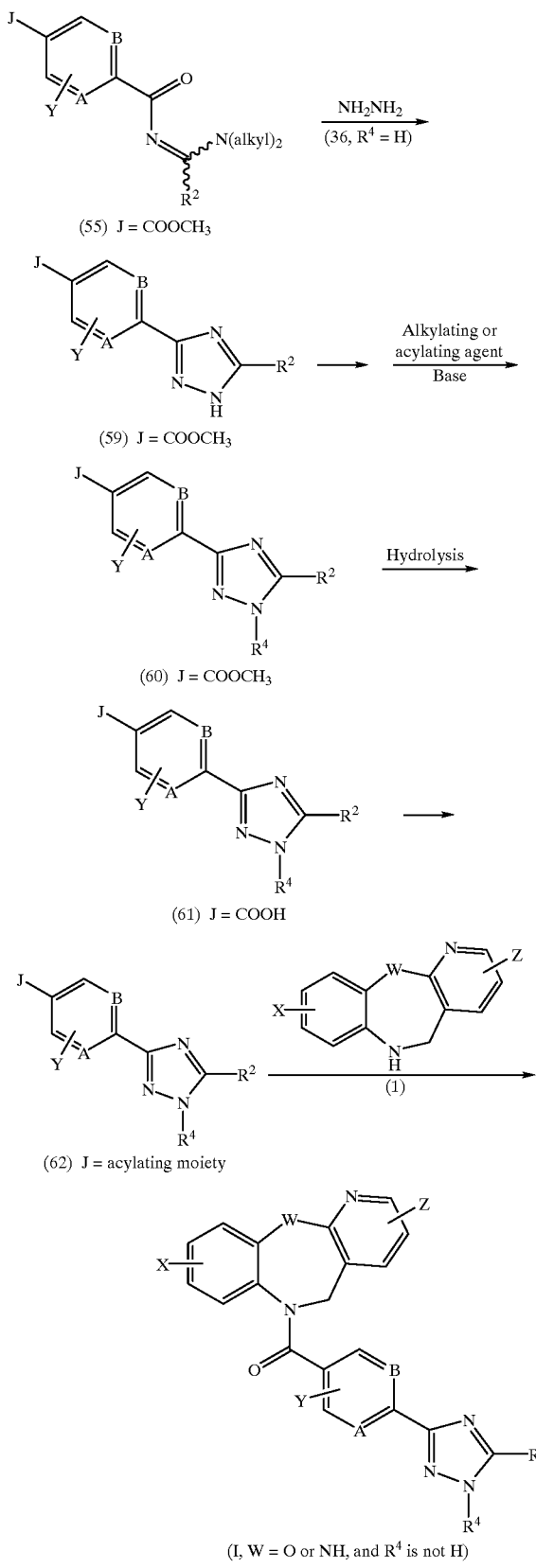

(I, W = O or NH, and R⁴ is not H)

Treatment of the intermediate ester of formula (55) of Scheme XVII with an unsubstituted hydrazine (36, where R⁴ is H) in acetic acid at temperatures ranging from ambient to the reflux temperature, yields the intermediate triazole ester of formula (59). In this case the heterocyclic nitrogen can be alkylated or acylated by procedures analogous to those described hereinbefore, to yield the substituted triazole ester of formula (60). The ester (60) is subsequently hydrolyzed to the carboxylic acid of formula (61) which is then converted into an acylating species, preferably an acid chloride or mixed anhydride of formula (62), by procedures analogous to those described hereinbefore. The acylating agent (62) is used to acylate a pyridobenzodiazepine (or benzoxazepine) of formula (1) to yield the desired compound of formula (I) wherein W is O or NH, X, Y, Z, A, B and R² are as defined above, R¹ is a heterocyclic moiety selected from the e or i group of heterocycles defined above, and R⁴ is not hydrogen.

Alternatively, a compound of general formula (I) of Scheme XV wherein W is O or NH, A, B, X, Y, Z and R² are as defined above, R¹ is an heterocyclic moiety selected from the e and i group of heterocycles defined above and illustrated below, and R⁴ is hydrogen, can be conveniently prepared from a compound of formula (I) of Scheme XVIII wherein R⁴ is an optionally substituted aralkyl group, preferably a p-methoxybenzyl group by using a number of procedures which include hydrogenolysis or treatment with a strong acid such as trifluoroacetic acid at temperatures ranging from 0° C. to reflux temperature, essentially according to the procedure of Buckle et al., *J. Chem. Soc. Perkin Trans.* 1, 627 (1982).

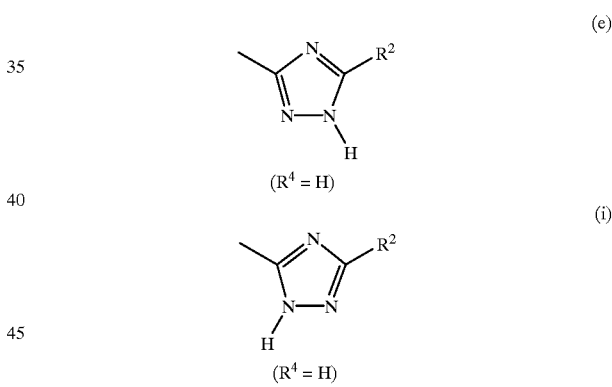

The preferred process to prepare compounds of general formula (I) in which R¹ contains four heteroatoms, W is O or NH, and R⁴ is hydrogen is outlined in Scheme XIX.

SCHEME XIX

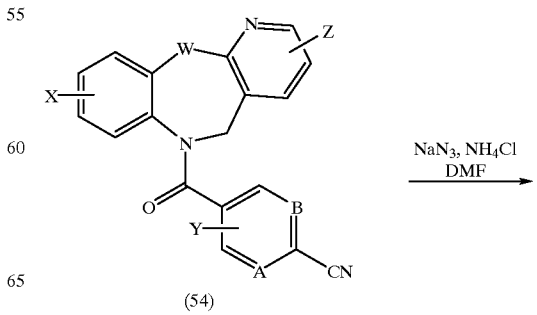

(54)

-continued

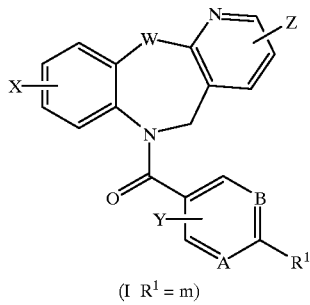

(I R$^1$ = m)

Treatment of the nitrile intermediate of formula (54) of Scheme XV with sodium azide and ammonium chloride in an aprotic organic solvent such as dimethylformamide at temperatures ranging from ambient to the reflux temperature of the solvent, yields the desired compound of formula (I) wherein W is O or NH, A, B, X, Y, and Z are as defined above, R$^1$ is an heterocyclic moiety selected from the m group of heterocycles defined above and illustrated below, and R$^4$ is hydrogen.

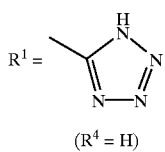

(R$^4$ = H)

The compounds of general formula (I) wherein R$^1$ is an heterocyclic moiety selected from the group e, f, g, h, i, j, or k, and W is NR$^6$ and R$^6$ is other than hydrogen, can be preferably prepared by alkylation or acylation of a compound of formula (I, W is NH) of Schemes VIII, IX, X, XII, and XV, as outlined in Scheme XX.

SCHEME XX

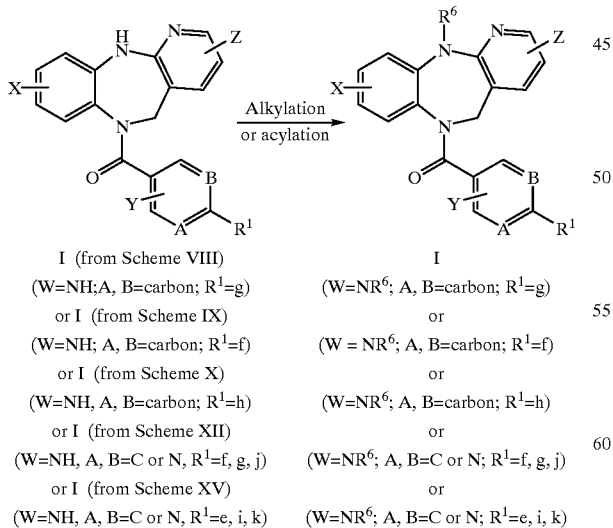

I (from Scheme VIII)
(W=NH; A, B=carbon; R$^1$=g)
or I (from Scheme IX)
(W=NH; A, B=carbon; R$^1$=f)
or I (from Scheme X)
(W=NH, A, B=carbon; R$^1$=h)
or I (from Scheme XII)
(W=NH, A, B=C or N, R$^1$=f, g, j)
or I (from Scheme XV)
(W=NH, A, B=C or N, R$^1$=e, i, k)

(W=NR$^6$; A, B=carbon; R$^1$=g)
or
(W = NR$^6$; A, B=carbon; R$^1$=f)
or
(W=NR$^6$; A, B=carbon; R$^1$=h)
or
(W=NR$^6$; A, B=C or N; R$^1$=f, g, j)
or
(W=NR$^6$; A, B=C or N; R$^1$=e, i, k)

Thus, the compounds of formula (I, W is NH) of Schemes VIII, IX, X, XII, and XV are alkylated by treatment with a base such as sodium (or potassium) hydride and an alkylating agent such as an alkyl halide, preferably an alkyl chloride (bromide or iodide) in an aprotic solvent such as dimethylformamide or tetrahydrofuran at temperatures ranging from 0° C. to 80° C. to yield compounds of formula (I) wherein W is NR$^6$ and R$^6$ is alkyl, and A, B and R$^1$ are as defined in Scheme XX and illustrated below.

Alternatively, the compounds of formula (I, W is NH) of Schemes VIII, IX, X, XII, and XV are acylated by treatment with a carboxylic acid halide or a carboxylic acid anhydride in the presence of an amine base such as pyridine or a trialkylamine such as triethylamine in an aprotic solvent such as dichloromethane or with no addition of solvent when pyridine is used as the base, at temperatures ranging from −40° C. to ambient, to yield compounds of formula (I) wherein W is NR$^6$ and R$^6$ is acyl, and A, B and R$^1$ are as defined in Scheme XX and illustrated below.

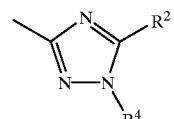
(e)

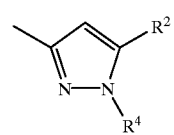
(f)

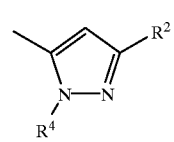
(g)

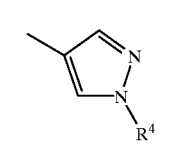
(h)

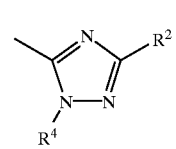
(i)

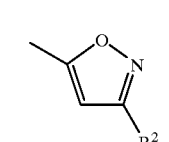
(j)

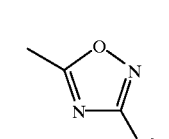
(k)

The compounds of general formula (I) wherein R$^1$ is an heterocyclic moiety selected from the group e, i, k, or m, and W is NR$^6$ and R$^6$ is other than hydrogen, can be conveniently prepared as shown in Scheme XXI.

SCHEME XXI

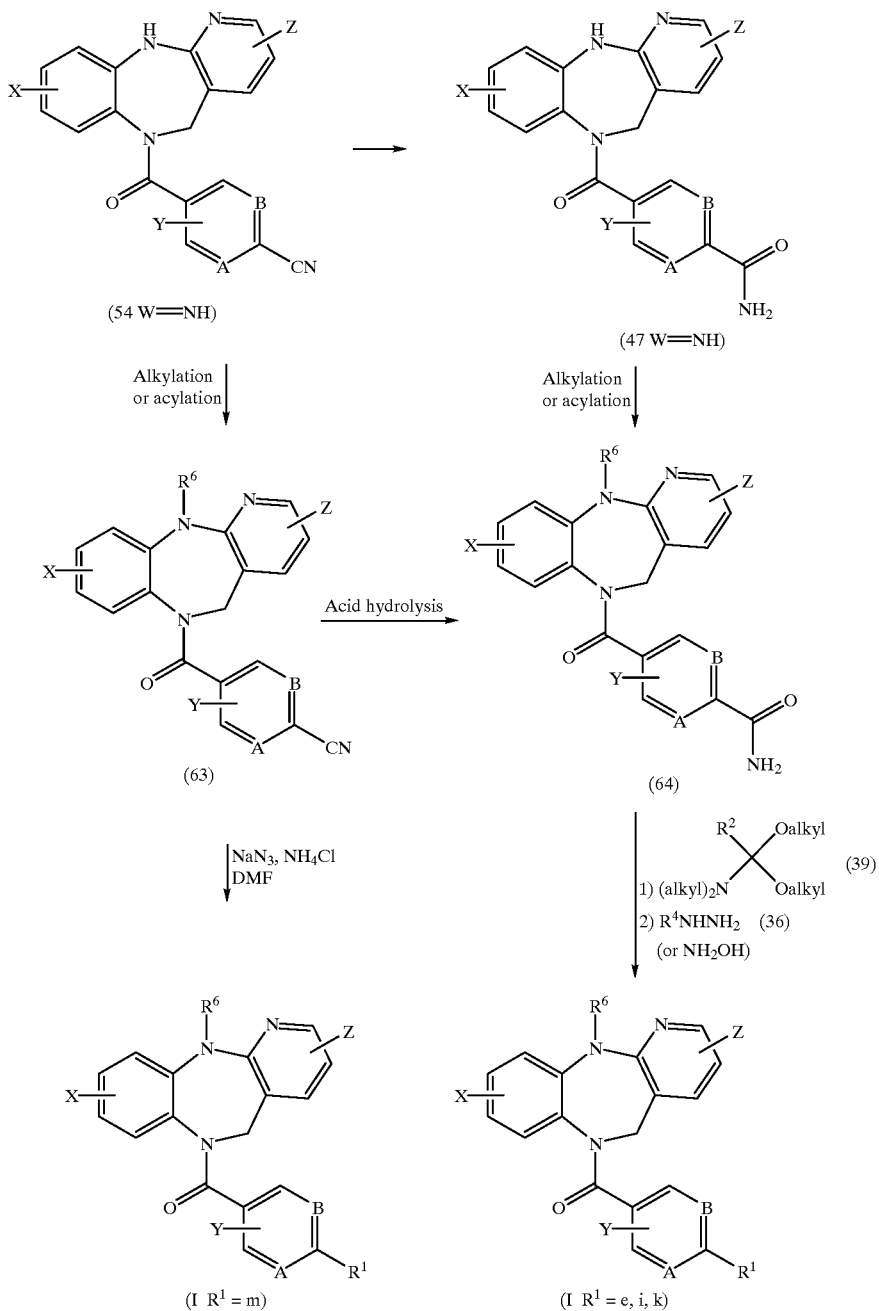

Thus a nitrile of formula (54, W is NH) of Scheme XV can be alkylated by treatment with a base such as sodium (or potassium) hydride and an alkylating agent such as an alkyl halide, preferably an alkyl chloride (bromide or iodide) in an aprotic solvent such as dimethylformamide or tetrahydrofuran at temperatures ranging from 0° C. to 80° C. to yield an alkylated nitrile of formula (63, W is $NR^6$ and $R^6$ is alkyl).

Conversely (54) can be acylated by treatment with a carboxylic acid halide or a carboxylic acid anhydride in the presence of an amine base such as pyridine or a trialkylamine such as triethylamine in an aprotic solvent such as dichloromethane or with no addition of solvent when pyridine is used as the base, at temperatures ranging from −40° C. to ambient, to yield compounds of formula (63, W is $NR^6$ and $R^6$ is acyl).

In a likely fashion using procedures analogous to those used for the nitrile (54, W=NH) above, an amide of formula (47, W is NH) of Scheme XV can be alkylated or acylated to yield alkylated or acylated intermediates of general formula (64, W=$NR^6$ and $R^6$=alkyl or acyl residue).

The intermediate nitrile (63) and amide (64) of Scheme XXI can then be converted respectively to either the compound of formula (I), wherein W is $NR^6$ and $R^6$=alkyl or acyl, and $R^1$ is selected from the group m of heterocycles defined in Scheme XIX, or to the compound of formula (I) wherein W=$NR^6$ and $R^6$ is alkyl or acyl and $R^1$ is selected from the group e, i or k of heterocycles defined in Scheme XV and illustrated below, by using procedures identical to those outlined in those same Schemes.

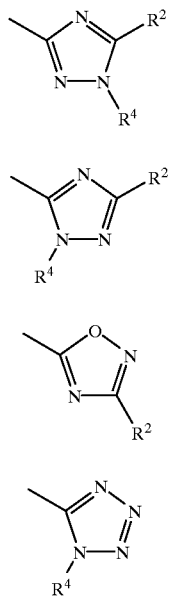

The subject compounds of the present invention were tested for biological activity according to the following procedures.

Vasopressin $V_2$ Agonist Effects of Test Compounds in Normal Conscious Water-Loaded Rats Male or female normotensive Sprague-Dawley rats (Charles River Laboratories, Inc., Kingston, N.Y.) of 350–500 g body weight were supplied with standard rodent diet (Purina Rodent Lab. Chow 5001) and water ad libitum. On the day of test, rats were placed individually into metabolic cages equipped with devices to separate the feces from the urine and containers for collection of urine. A test compound or a reference agent was given at an oral dose of 10 mg/kg in a volume of 10 ml/kg. The vehicle used was 20% dimethylsulfoxide (DMSO) in 2.5% preboiled corn starch. Thirty minutes after dosing the test compound, rats were gavaged with water at 30 ml/kg into the stomach using a feeding needle. During the test, rats were not provided with water or food. Urine was collected for four hours after dosing of the test compound. At the end of four hours, urine volume was measured. Urinary osmolality was determined using a Fiske One-Ten Osmometer (Fiske Associates, Norwood, Ma., 02062) or an Advanced CRYOMATIC Osmometer, Model 3C2 (Advanced Instruments, Norwood, Ma.). Determinations of $Na^+$, $K^+$ and $Cl^-$ ion were carried out using ion specific electrodes in a Beckman SYNCHRON EL-ISE Electrolyte System analyzer. The urinary osmolality should increase proportionally. In the screening test, two rats were used for each compound. If the difference in the urine volume of the two rats was greater than 50%, a third rat was used. The results of this study are shown in Table I, below.

TABLE 1

| Example | Urine Volume (% decrease)[a] | Changes in Urinary Osmolality[b] | Rat Type[c] |
|---|---|---|---|
| 1 | 80 | 272 | CD |
| 2 | 61 | 288 | CD |
| 3 | 85 | 346 | CD |
| 4 | 87 | 339 | CD |
| 6 | 25 | 103 | CD |
| 7 | 69 | 283 | CD |
| 8 | 72 | 298 | CD |
| 9 | 59 | 372 | CD |
| 10 | 63 | 276 | CD |
| 11 | 71 | 375 | CD |
| 12 | −2 | 101 | CD |
| 13 | 6 | 106 | CD |
| 14 | 83 (1 mg/kg) | 321 | CD |
| 15 | 98 (1 mg/kg) starch only | 1363 | CD |
| 16 | 41 | 142 | CD |
| 17 | 72 | 262 | CD |
| 18 | 76 | 234 | CD |
| 20 | 10 | 89 | CD |
| 24 | 86 | 615 | CD |

[a]Percent decrease in urine volume vs. control at a dose of 10 mg/kg
[b]Osmolality changes expressed as percent of control at a dose of 10 mg/kg
[c]Rat model used: Sprague-Dawley (CD)

The following examples are presented to illustrate rather than limit the scope of invention.

EXAMPLE 1

[2-Chloro-4-(3-methyl-pyrazol-1-yl)-phenyl]-(5,11-dihydro-pyrido [2,3-b][1,5]benzodiazepin-6-yl)-methanone Step A. 6,11-Dihydro-5H-pyrido[2,3-b][1,5]benzodiazepin-5-one 1:1 salt with hydrochloric acid A mixture of 1,2-phenylene diamine (52 g, 480 mmol) and chloronicotinic acid (76 g, 482 mmol) in cyclohexanol (480 mL) was refluxed under nitrogen for 2.5 hours. A precipitate appeared soon after the heating was initiated. The warm reaction mixture was carefully poured onto ice-cold dichloromethane (1000 mL) under vigorous stirring. The semisolid mass was collected, washed thoroughly with dichloromethane and dried in vacuo to yield 98.9 g (83%) of the title compound which was used in the next step without further purification.

Step B. 6,11-Dihydro-5H-pyrido[2,3-b][1,5]benzodiazepine

Diborane dimethylsulfide complex (35 mL) was added via syringe to a suspension of 6,11-dihydro-5H-pyrido[2,3-b][1,5]benzodiazepin-5-one 1:1 salt with hydrochloric acid of Step A (25 g, 0.1 mole) in dioxane (230 mL) under nitrogen. The mixture was sonicated overnight at room temperature and then evaporated to dryness in vacuo. The green residue was treated with cold 2N hydrochloric acid and diethyl ether. The cold aqueous layer was basified with 50% aqueous sodium hydroxide (to pH 9) and the basic layer extracted with ethyl acetate. The organic extracts were dried over anhydrous potassium carbonate, and evaporated to dryness to yield a burgundy solid (24.35 g, 61.4%). This crude material was purified by trituration with diethyl ether. The solid was collected, washed and dried in vacuo. The mother liquors from different runs were combined and the mixture (18.5 g) flash chromatographed (on silica Merck-60, eluant 20% ethyl acetate in hexane) to provide additional material homogeneous by TLC (yellow solid, 11 g).

Step C. 2-Chloro-4-fluorobenzoyl chloride

A suspension of the 2-chloro-4-fluorobenzoic acid (13.61 g, 78 mmol) in dichloromethane (85 mL) containing a few drops of dimethylformamide was treated dropwise under nitrogen with a 2M solution of oxalyl chloride in dichloromethane (1.2 equivalents). After gas evolution subsided, the reaction mixture was refluxed for an additional 25 minutes and then evaporated to dryness in vacuo. The crude acid chloride was used as such in the next step.

Step D. (2-Chloro-4-fluorophenyl)-(5,11-dihydro-pyrido[2,3-b][1,5]benzodiazepin-6-yl)-methanone To a solution of 6,11-dihydro-5H-pyrido[2,3-b][1,5] benzodiazepine of Step B (12.8 g, 65 mmol) in dimethylformamide (120 mL) under nitrogen was added potassium carbonate (19.76 g, 143 mmol). The mixture was cooled and treated dropwise with a solution of crude 2-chloro-4-fluorobenzoyl chloride of Step C (78 mmol) in dimethylformamide (50 mL). After stirring at room temperature for 75 minutes the mixture was diluted with water and extracted with dichloromethane. The organic extracts were dried over magnesium sulfate and evaporated to dryness. The crude material was purified by flash chromatography (on silica Merck-60, hexane-ethyl acetate gradient from 95:5 to 80:20) to provide the pure title compound (14.25 g, 62%) along with some less pure material (2.7 g). The pure material is an off-white crystalline solid, which is used as such in the next step.

NMR (DMSO-$d_6$, 400 MHz): δ 4.13 and 5.42 (dd, 2 H, CONCH$_2$), 6.52 (m, 1H), 6.71–6.79 (m, 2H), 6.98–7.16 (2 m, 2H), 7.23–7.33 (m, 3H), 7.58 (m, 1H), 8.10 (m, 1H), 9.53 (s, 1H, NH); MS (EI, m/z): 353/355 [M]$^+$, 196.

Step E. [2-Chloro-4-(3-methyl-pyrazol-1-yl)-phenyl]-(5,11-dihydro-pyrido[2,3-b][1,5]benzodiazepin-6-yl)-methanone Sodium hydride (60% suspension in oil, 1.8 g, 45.19 mmol) was washed with hexane, dried under nitrogen and resuspended in dry dimethylformamide (130 mL). Neat 3-methyl pyrazole (3.71 g, 45.19 mmol) was added dropwise at 0° C. After the gas evolution subsided the cooling bath was removed and stirring was continued at room temperature. The (2-chloro-4-fluorophenyl)-(5,11-dihydropyrido[2,3-b][1,5]benzodiazepin-6-yl)-methanone of Step D (8.11 g, 22.59 mmol) was added in one portion and the mixture was placed in an oil bath (preheated at 130° C.) for 2 hrs. After cooling, the mixture was partitioned between water and ethyl acetate. The organic extracts were dried over sodium sulfate, and evaporated to dryness in vacuo. The residue was dissolved in dichloromethane and absorbed onto a silica Merck-60 flash column. Elution with a hexane-ethyl acetate gradient (from 95:5 to 3:2) provided the desired product along with some mixed fractions containing the tide compound and its more polar 5-methylpyrazole regioisomer of Example 2. The title compound crystallized by sonication from hexane-ethanol as a white solid (6.4 g, 68%), m.p. 207° C.

NMR (DMSO-$d_6$, 400 MHz): δ 2.21 (s, 3H), 4.14 and 5.45 (dd, 2H, CONCH$_2$), 6.32 (m, 1H, pyrazole CH), 6.51 (m, 1H), 6.74–6.79 (2m, 2H), 6.98 (m, 1H), 7.25 (m, 2H), 7.58–7.70 (mm, 3H), 8.11 (m, 1H), 8.38 (m, 1H, pyrazole CH), 9.55 (s, 1H, NH); MS (EI, m/z): 415/417 [M]$^+$; (+FAB, m/z): 416/418 [M+H]$^+$; Anal. Calc'd for C$_{23}$H$_{18}$ClN$_5$O: C 66.43; H 4.36; N 16.84. Found: C 66.11; H 4.42; N 16.64.

EXAMPLE 2

[2-Chloro-4-(5-methyl-pyrazol-1-yl)-phenyl] (5,11-dihydro-pyrido [2,3-b][1,5]benzodiazepin-6-yl)-methanone The fractions (0.543 g) containing a mixture of 3-methyl and 5-methylpyrazole regioisomers obtained as described in Example 1, Step E were subjected to flash chromatography (silica gel Merck-60, eluant: toluene-ethyl acetate 90:10 followed by toluene-ethyl acetate-acetonitrile 90:10:5) to provide 0.327 g of the already described 3-methyl isomer of Example 1 and 0.105 g of the title compound as an amorphous solid upon sonication from ether-hexane.

NMR (DMSO-$d_6$, 400 MHz): δ 2.27 (s, 3H), 4.16 and 5.45 (dd, 2H, CONCH$_2$), 6.25 (m, 1H), 6.54 (m, 1H, pyrazole CH), 6.79 (m, 2H), 7.01 (m, 1H), 7.26 (m, 1H), 7.40–7.54 (mm, 3H), 7.61 (m, 1H), 8.11 (m, 1H, pyrazole CH), 9.56 (s, 1H, NH); MS [EI, m/z]: 415/417 [M]$^+$, 219/221, 196.

EXAMPLE 3

[2-Bromo-4-(3-methyl-pyrazol-1-yl)-phenyl]-(5,11-dihydro-pyrido [2,3-b][1,5]benzodiazepin-6-yl)-methanone Step A. 2-Bromo-4-fluorobenzoyl chloride A suspension of 2-bromo-4-fluorobenzoic acid (6.87 g, 31.37 mmol) in dichloromethane (70 mL) containing a few drops of dimethylformamide was treated dropwise under nitrogen with a 2M solution of oxalyl chloride in dichloromethane (1.16 equivalents). After gas evolution subsided, the reaction mixture was refluxed for an additional 25 minutes and then the solution was evaporated to dryness in vacuo. The crude acid chloride was used as such in the next step.

Step B. [2-Bromo-4-fluorophenyl]-(5,11-dihydro-pyrido [2,3-b][1,5]benzodiazepin-6-yl)-methanone To a solution of 6,11-dihydro-5H-pyrido[2,3-b][1,5] benzodiazepine of Example 1, Step B (5.15 g, 26.1 mmol) in dimethylformamide (70 mL) under nitrogen was added potassium carbonate (7.95 g, 57.51 mmol). The mixture was cooled and treated dropwise with a solution of crude 2-bromo4-fluorobenzoyl chloride of Step A (31.37 mmol) in dimethylformamide (30 mL). After stirring at room temperature for 75 minutes the mixture was diluted with water and extracted with dichloromethane. The organic extracts were dried over magnesium sulfate and evaporated to dryness to give a brown solid foam. The crude material was dissolved in dichloromethane and absorbed onto a silica Merck-60 flash column. Elution with a hexane-ethyl acetate gradient (from 95:5 to 75:25) provided the pure title compound (6.18 g, 59.5%) along with some impure material (1.2 g). The pure material was triturated with hexane to provide an off-white solid foam, which was used as such in the next step.

NMR (DMSO-$d_6$, 400 MHz): δ 4.13 and 5.42 (dd, 2 H, CONCH$_2$), 6.53 (m, 1H), 6.74–6.79 (m, 2H), 6.98–7.16 (2 m, 3H), 7.25 (m, 1H), 7.40–7.50 (broad s, 1H), 7.59 (m, 1H), 8.1 (m, 1H), 9.54 (s, 1H, NH); MS (EI, m/z): 397/399 [M]$^+$, 196.

Step C. [2-Bromo-4-(3-methyl-pyrazol-1-yl)-phenyl]-(5,11-dihydro-pyrido [2,3-b][1,5]benzodiazepin-6-yl)-methanone Sodium hydride (60% suspension in oil, 1.2 g, 30.15 mmol) was washed with hexane, dried under nitrogen and resuspended in dry dimethylformamide (110 mL). Neat 3-methylpyrazole (2.47 g, 30.15 mmol) was added dropwise at 0° C. After the gas evolution subsided the cooling bath was removed and stirring was continued at room temperature. The [2-bromo-4-fluorophenyl]-(5,11-dihydro-pyrido [2,3-b][1,5]benzodiazepin-6-yl)-methanone of Step B (6 g, 18.07 mmol) was added in one portion to the clear solution. The mixture was placed in an oil bath (preheated at 130° C.) for 40 minutes, cooled and partitioned between water and ethyl acetate. The organic extracts were dried over magnesium sulfate and evaporated to dryness. The crude material was dissolved in dichloromethane and absorbed onto a silica Merck-60 flash column. Elution with a hexane-ethyl acetate gradient (from 95:5 to 75:25) provided the less polar title compound (3.87 g) along with a mixture of 3- and 5-methylpyrazole regioisomers (0.860 g). The title compound (3.5 g, 51%) crystallized by sonication from hexane-ethanol, m.p. 208–209° C. (dec).

NMR (DMSO-$d_6$, 400 MHz): δ 2.21 (s, 3H), 4.15 and 5.44 (dd, 2H, CONCH$_2$), 6.31 (m, 1H, pyrazole CH), 6.52 (m, 1H), 6.77–6.80 (2m, 2H), 6.99 (m, 1H), 7.25 (m, 1H), 7.59–7.63 (2 m, 2H), 7.88 (m, 1H), 8.11 (m, 1H), 8.37 (s, 1H, pyrazole CH), 9.55 (s, 1H, NH); MS (+EI, m/z): 459/461 [M]$^+$, 265/263; Anal. Calc'd for $C_{23}H_{18}BrN_5O$: C 60.01, H 3.94, N 15.21. Found: C 59.92, H 4.05, N 15.01.

EXAMPLE 4

(5,11-dihydro-pyrido[2,3-b][1,5]benzodiazepin-6-yl)-[4-(3-methyl-pyrazol-1-yl)-2-trifluoromethyl-phenyl]-methanone Step A. 2-Trifluoromethyl-4-fluorobenzoyl chloride A suspension of 2-trifluoromethyl-4-fluorobenzoic acid (16.85 g, 81 mmol) in dichloromethane (150 mL) containing a few drops of dimethylforrnamide was treated dropwise under nitrogen with oxalyl chloride (8.5 mL, 97.4 mmol). After the gas evolution subsided, the reaction mixture was refluxed for an additional 10 minutes, and then evaporated to dryness in vacuo. The crude acid chloride was used as such in the next step.

Step B. (5,11-Dihydro-pyrido[2,3-b][1,5]benzodiazepin-6-yl)-(4-fluoro-2-trifluoromethyl-phenyl)-methanone To a solution of 6,11-dihydro-5H-pyrido[2,3-b][1,5]benzodiazepine of Example 1, Step B (10.6 g, 53.8 mmol) in dimethylformamide (125 mL) under nitrogen was added potassium carbonate (22.4 g, 162 mmol). The mixture was cooled and treated dropwise with a solution of crude 2-trifluoromethyl-4-fluorobenzoyl chloride of Step A (81 mmol) in dimethylformamide (25 mL). After stirring at room temperature for 2 hours, the mixture was diluted with water and extracted with dichloromethane. The organic extracts were dried over magnesium sulfate and evaporated to dryness. The crude material was dissolved in dichloromethane and purified by flash chromatography (on silica Merck-60, hexane-ethyl acetate 80:20) to provide the pure title compound (6.9 g, 33.1%) which was crystallized by sonication from ethanol-hexane, m.p. 183–185° C.

NMR (DMSO-$d_6$, 400 MHz) δ 4.16 and 5.43 (dd, 2 H, CONCH$_2$), 6.56 (m, 1H), 6.64 (m, 1H), 6.79 (m, 1H), 7.02 (m, 1H), 7.26–7.40 (m, 3H), 7.58–7.65 (m, 2H), 8.12 (m, 1H), 9.59 (s, 1H, NH); MS (EI, m/z): 387 [M]$^+$; Anal. Calc'd for $C_{20}H_{13}F_4N_3O$: C 62.02, H 3.38, N 10.85. Found: C 62.06, H 3.22, N 10.67.

Step C. (5,11-Dihydro-pyrido[2,3-b][1,5]benzodiazepin-6-yl)-[4-(3-methyl-pyrazol-1-yl)-2-trifluoromethyl-phenyl]-methanone Sodium hydride (60% suspension in oil, 0.83 g, 20.8 mmol) was washed once with hexane, dried under nitrogen and resuspended in dry dimethylformamide (60 mL). 3-methyl pyrazole (0.90 mL, 11.2 mmol) was added in one portion. After the gas evolution subsided the stirring was continued at room temperature. The (5,11-dihydro-pyrido[2,3-b][1,5]benzodiazepin-6-yl)-(4-fluoro-2-trifluoromethyl phenyl)-methanone of Step B (3.6 g, 9.3 mmol) was added in one portion and the mixture was placed in an oil bath (preheated at 130° C.) for 30 minutes. After cooling, the mixture was partitioned between water and ethyl acetate. The organic extracts were dried over sodium sulfate, and evaporated to dryness. The residue was dissolved in dichloromethane and absorbed onto a silica Merck-60 flash column. Elution with 25% ethyl acetate in hexane provided 3.3 g (79%) of the desired product as a foam which crystallized by sonication from ethanol-hexane, m.p. 212–214° C. Further elution with 30% ethyl acetate in hexane yielded the more polar 5-methylpyrazole regioisomer of Example 6.

NMR (DMSO-$d_6$, 400 MHz): δ 2.23 (s, 3H, CH$_3$), 4.17 and 5.45 (dd, 2H, CONCH$_2$), 6.35 (m, 1H, pyrazole CH), 6.54 (m, 1H), 6.68 (m, 1H), 6.80 (m, 1H), 7.00 (m, 1H), 7.29 (m, 1H), 7.60 (m, 1H), 7.85 (m, 1H), 8.04 (m, 1H), 8.13 (m, 1H), 8.46 (m, 1H, pyrazole CH), 9.61 (s, 1H, NH); MS (EI, m/z): 449 [M]$^+$; Anal. Calc'd for $C_{24}H_{18}F_3N_5O$: C 64.14, H 4.04, N 15.58. Found: C 64.01, H 4.01, N 15.45.

EXAMPLE 5

(5,11-dihydro-pyrido[2,3-b][1,5]benzodiazepin-6-yl)-[4-(3-methyl-pyrazol-1-yl)-2-trifluoromethyl-phenyl]-methanone Step A. 4-Fluoro-2-trifluoromethylbenzoic acid methyl ester A suspension of 4-fluoro-2-trifluoromethylbenzoic acid (25.6 g, 123.0 mmol) in dichloromethane (250 mL) containing a few drops of dimethylformamide was treated dropwise under nitrogen with oxalyl chloride (11.3 mL, 129.5 mmol). After the gas evolution subsided, the reaction mixture was refluxed for an additional 15 minutes. The mixture was cooled and methanol (50 mL) was added. After stirring for 2 hrs, the reaction was concentrated, and the residue was partitioned between dichloromethane and water. The organic phase was washed with saturated aqueous sodium bicarbonate, dried over sodium sulfate, and evaporated to dryness to give 18.0 g (65.9%) of the title compound as a golden oil.

NMR (DMSO-$d_6$, 400 MHz): δ 3.85 (s, 3H), 7.67 (m, 1H), 7.80 (m, 1H), 7.95 (m, 1H)MS (EI, m/z): 222 [M]$^+$.

The aqueous layer was acidified with 2 N hydrochloric acid and the white solid was collected by filtration to give 7.5 g (29.3%) of the starting 4-fluoro-2-trifluoromethylbenzoic acid.

Step B. 4-(3-Methyl-pyrazol-1-yl)-2-trifluoromethyl benzoic acid methyl ester

Sodium hydride (60% suspension in oil, 3.85 g, 96.3 mmol) was washed with hexane, dried under nitrogen and resuspended in dry dimethylformamide (150 mL). A solution of 3-methylpyrazole (7.75 mL, 96.3 mmol) in dimethylformarnide (50 mL) was added dropwise at ambient temperature. Stirring was continued until the gas evolution subsided, and then a solution of methyl 4-fluoro-2-trifluoromethylbenzoic acid methylester of Step A (17.8 g, 80.1 mmol) in dimethylformamide (50 mL) was added dropwise to the clear solution. After stirring for 30 min at room temperature, the reaction was quenched with saturated aqueous ammonium chloride and extracted with ethyl acetate. The organic extracts were dried over sodium sulfate and evaporated to dryness. The residue was dissolved in 1:1 mixture of dichloromethane and hexane and absorbed onto a silica Merck-60 flash column. Elution with a dichloromethane-hexane gradient (from 1:1 to 4:1) provided the title compound (13.6 g, 59.7%) as a white solid, m.p. 59–61° C.

NMR (DMSO-$d_6$, 400 MHz): δ 2.28 (s, 3H), 3.86 (s, 3H, CO$_2$CH$_3$), 6.43 (m, 1H, pyrazole CH), 7.97 (m, 1H), 8.18 (m, 1H), 8.23 (m, 1H), 8.62 (m, 1H, pyrazole CH); MS (EI, m/z): 284 [M]$^+$; Anal. Calc'd for $C_{13}H_{11}F_3N_2O_2$: C 54.93, H 3.90, N 9.86. Found: C 54.80, H 3.73 N 9.81.

Step C. 4-(3-Methyl-pyrazol-1-yl)-2-trifluoromethyl benzoic acid

To a solution of 4-(3-methylpyrazol-1-yl)-2-trifluoromethybenzoic acid methylester of Step B (1.19 g, 4.2 mmol) in methanol (10 mL) was added 2.5 N sodium hydroxide (3.3 mL, 8.3 mmol). The mixture was heated at reflux for 90 minutes, cooled and concentrated. The residue was partitioned between ethyl acetate and 1N hydrochloric acid. The organic extracts were dried over sodium sulfate and evaporated to dryness to give the title compound (1.14 g, quantitative yield) as a white solid, m.p. 192–194° C.

NMR (DMSO-$d_6$, 400 MHz): δ 2.28 (s, 3H), 6.42 (m, 1H, pyrazole CH), 7.95 (m, 1H), 8.14 (m, 1H), 8.20 (m, 1H), 8.61 (m, 1H, pyrazole CH), 13.4–13.7 (broad s, 1H, COOH); MS (+FAB, m/z): 271 [M+H]$^+$; Anal. Calc'd for $C_{12}H_9F_3N_2O_2$: C 53.34, H 3.36, N 10.37. Found: C 53.35, H 3.29, N 10.21.

Step D. (5,11-Dihydro-pyrido[2,3-b][1,5]benzodiazepin-6-yl)-[4-(3-methyl-pyrazol-1-yl)-2-trifluoromethyl-phenyl]-methanone To a solution of 4-(3-methyl-pyrazol-1-yl)-2-trifluoromethyl benzoic acid (1.1 g, 4.1 mmole) of Step C, and triethylamine (0.57 mL, 4.1 mmol) in dichloromethane (20 mL) was added 1,3,5-trichlorobenzoyl chloride (0.63 mL, 4.0 mmol). After stirring for 5.5 hours, 6,11-dihydro-5H-pyrido[2,3-b][1,5]benzodiazepine of Example 1, Step B (0.67 g, 3.4 mmol) and 4-dimethylamino pyridine (0.42 g, 3.4 mmol) were added. After stirring for an additional 18 hours, the mixture was poured into saturated aqueous sodium bicarbonate. The organic phase was washed with brine, dried over sodium sulfate, and evaporated to dryness. The residue was dissolved in dichloromethane and absorbed onto a silica Merck-60 flash column. Elution with hexane-ethyl acetate (gradient from 8:2 to 7:3) provided the title product (0.89 g, 58.2%) as a foam which crystallized by sonication from ethanol-hexane, m.p. 212–214° C. This material was identical to the compound of Example 4.

EXAMPLE 6

(5,11-dihydro-pyrido[2,3-b[]1,5benzodiazepin-6-yl)-[4-(5-methyl-pyrazol-1-yl)-2-trifluoromethyl-phenyl]-methanone The title compound (0.350 g, 8%) was obtained as described in Example 4 above, as a foam which crystallized by sonication from ethanol-hexane, m.p. 238–240° C.

NMR (DMSO-$d_6$, 400 MHz): δ 2.29 (s, 3H), 4.19 and 5.46 (dd, 2H, CONCH$_2$), 6.28 (m, 1H, pyrazole CH), 6.57 (m, 1H), 6.71 (m, 1H), 6.80 (m, 1H), 7.02 (m, 1H), 7.29 (m, 1H), 7.58–7.67 (m, 4H), 7.81 (m, 1H), 8.13 (m, 1H), 9.63 (s, 1H, NH); MS (+FAB, m/z): 450 [M+H]$^+$; Anal. Calc'd for $C_{24}H_{18}F_3N_5O$+0.09 $CH_2Cl_2$ +0.13 $C_4H_8O_2$: C 63.09, H 4.13, N 14.95. Found: C 63.39, H 4.23, N 14.89.

EXAMPLE 7

(5,11-dihydro-pyrido[2,3-b][1,5benzodiazepin-6-yl)-]2-trifluoromethyl-4-(3-trifluoromethyl-pyrazol-1-yl)-phenyl]-methanone Sodium hydride (60% suspension in oil, 0.17 g, 4.25 mmol) was washed with hexane, dried under nitrogen and resuspended in dry dimethylformamide (10 mL). 3-trifluoromethyl pyrazole (0.34 g, 2.5 mmol ) was added in one portion. After the gas evolution subsided stirring was continued at room temperature. The (5,11-dihydro-pyrido[2,3-b][1,5]benzodiazepin-6-yl)-(4-fluoro-2-trifluoromethyl-phenyl)-methanone of Example 4, Step B (0.75 g, 1.94 mmol) was added in one portion and the mixture was placed in an oil bath (preheated at 130° C.) overnight. After cooling, the mixture was partitioned between water and ethyl acetate. The organic extracts were dried over sodium sulfate, and evaporated to dryness in vacuo. The residue was crystallized from ethanol to yield the title compound (0.57 g, 57.3%) as an off-white solid, m.p. 127–129° C.

NMR (DMSO-$d_6$, 400 MHz): δ 4.19 and 5.46 (dd, 2H, CONCH$_2$), 6.54 (m, 1H), 6.70 (m, 1H), 6.80 (m, 1H), 7.02 (m, 1H), 7.07 (m, 1H, pyrazole CH), 7.29 (m, 1H), 7.61 (m, 1H), 8.00 (m, 1H), 8.05–8.16 (m, 2H), 8.84 (m, 1H, pyrazole CH), 9.63 (s, 1H, NH); MS (EI, m/z): 503 [M]$^+$; Anal. Calc'd for $C_{24}H_{15}F_6N_5O$: C 57.26, H 3.00, N 13.91. Found: C 57.07, H 2.97, N 13.58.

EXAMPLE 8

(11-methyl-5,11-dihydro-pyrido[2,3-b][1,5]benzodiazepin-6-yl)-[4-(3-methyl-pyrazol-1-yl)-2-trifluoromethyl-phenyl]methanone Sodium hydride (60% suspension in oil, 0.12 g, 3.0 mmol) was washed with hexane, dried under nitrogen and resuspended in dry dimethylformamide (20 mL). Neat 3-methylpyrazole (0.13 mL, 1.61 mmol) was added dropwise at ambient temperature. Stirring was continued until the gas evolution subsided, and then the (5,11-dihydro-pyrido [2,3-b][1,5]benzodiazepin-6-yl)-(4-fluoro-2-trifluoromethyl-phenyl)methanone of Example 4, Step B (0.52 g, 1.34 mmol) was added in one portion to the clear solution. The mixture was placed in an oil bath (preheated at 130° C.) for 30 minutes. After cooling, sodium hydride (60% suspension in oil, 0.080 g, 2.0 mmol, washed with hexane) and methyl iodide (0.25 mL, 4.0 mmol) were added. The reaction mixture was stirred for an additional 15 minutes, and then partitioned between water and ethyl acetate. The organic extracts were dried over sodium sulfate and evaporated to dryness. The residue was dissolved in dichloromethane and absorbed onto a silica Merck-60 flash column. Elution with 20% ethyl acetate in hexane provided the title product (0.28 g, 45.1%) as a foam which crystallized by sonication from ethanol-hexane as a white solid, m.p. 188–190° C.

NMR (DMSO-$d_6$, 400 MHz): δ 2.23 (s, 3H, CCH$_3$), 3.55 (s, 3H, NCH$_3$), 4.37–4.43 (broad s, 1H, CONCH$_2$), 5.71–5.76 (broad s, 1H, CONCH$_2$), 6.35 (m, 1H, pyrazole CH), 6.89–6.93 (m, 3H), 7.19–7.24 (m, 2H), 7.31 (m, 1H), 7.61 (m, 1H), 7.90 (m, 1H), 8.06 (m, 1H), 8.24 (m, 1H), 8.48 (m, 1H, pyrazole CH); MS (EI, m/z): 463 [M]$^+$; Anal. Calc'd for $C_{25}H_{20}F_3N_5O$: C 64.79, H 4.35, N 15.11. Found: C 64.55, H 4.29, N 15.04.

EXAMPLE 9

(5,11-dihydro-pyrido[2,3-b][1,5]benzodiazepin-6-yl)-[2-fluoro-4-(3-methyl-pyrazol-1-yl)-phenyl]-methanone Step A. 2,4-Difluoro benzoylchloride A suspension of 2,4-difluorobenzoic acid (3.6 g, 22.8 mmol) in dichloromethane (40 mL) containing a few drops of dimethylformamide was treated dropwise under nitrogen with oxalyl chloride (2.4 mL, 27.5 mmol). After gas evolution subsided, the reaction mixture was refluxed for an additional 15 minutes, and then the solution was evaporated to dryness in vacuo. The crude acid chloride was used as such in the next step.

Step B. (2,4-Difluoro-phenyl)-(5,11-dihydro-pyrido[2,3-b][1,5]benzodiazepin-10-yl)-methanone To a solution of 6,11-dihydro-5H-pyrido[2,3-b][1,5]benzodiazepine of Example 1, Step B (3.0 g, 15.2 mmol) in dimethylformamide (35 mL) under nitrogen was added potassium carbonate (6.3 g, 45.6 mmol) followed by a solution of the crude 2,4-difluorobenzoylchloride of Step A (22.8 mmol) in dimethylformamide (15 mL). After stirring at room temperature for 20 minutes, the reaction mixture was washed with water and stirred to give a solid which was collected by filtration. The solid was dissolved in chloroform and washed with 1 N sodium hydroxide and brine. The organic phase was dried over sodium sulfate and evaporated to dryness. The crude material was dissolved in dichloromethane and absorbed onto a silica Merck-60 flash column. Elution with 20% ethyl acetate in hexane provided the title compound (2.6 g, 51%) as a white foam which crystallized by sonication from hexane-ethanol, m.p. 16114 163° C.

NMR (DMSO-$d_6$, 400 MHz): δ 4.12–5.46 (dd, 2H, CONCH$_2$), 6.52 (m, 1H), 6.67 (m, 1H), 6.76 (m, 1H), 6.98–7.07 (m, 3H), 7.26 (m, 1H), 7.35 (m, 1H), 7.57 (m, 1H), 8.10 (m, 1H), 9.56 (s. 1H, NH); MS (EI, m/z): 337 [M]$^+$; Anal. Calc'd for $C_{19}H_{13}F_2N_3O$: C 67.65; H 3.88; N 12.46. Found: C 67.30; H 3.98; N 12.10.

Step C. (5,11-Dihydro-pyrido[2,3-b][1,5]benzodiazepin-10-yl)-[2-fluoro-4-(3-methyl-pyrazol-1-yl)-phenyl]-methanone 0.19 hydrate Sodium hydride (60% suspension in oil, 0.48 g, 12.0 mmol) was washed with hexane, dried under nitrogen and resuspended in dry dimethylformamide (60 mL). Neat 3-methylpyrazole (0.48 mL, 6.0 mmol) was added. Stirring was continued until the gas evolution subsided. The (2,4-difluoro-phenyl)-(5,11-dihydro-pyrido[2,3-b][1,5]benzodiazepin-10-yl)-methanone of Step B (2.0 g, 5.9 mmol) was added in one portion to the clear solution. The mixture was placed in an oil bath (preheated at 130° C.) for 1 hour, cooled and partitioned between water and ethyl acetate. The organic extracts were dried over sodium sulfate and evaporated to dryness. The crude material was dissolved in dichloromethane and absorbed onto a silica Merck-60 flash column. Elution with hexane-ethyl acetate (gradient from 9:1 to 1:1) provided the title compound along with the more polar 4-fluoro regioisomer of Example 10. The title compound (0.30 g, 12.7%) was obtained as a foam which crystallized by sonication from hexane-ethanol, m.p. 122–125° C.

NMR (DMSO-$d_6$, 400 MHz): δ 2.21 (s, 3H, CH$_3$), 4.13 and 5.48 (dd, 2H, CONCH$_2$), 6.32 (m, 1H, pyrazole CH), 6.51 (m, 1H), 6.70 (m, 1H), 6.77 (m, 1H), 7.01 (m, 1H), 7.27 (m, 1H), 7.35 (m, 1H), 7.41 (m, 1H), 7.53–7.59 (m, 2H), 8.10 (m, 1H), 8.35 (m, 1H, pyrazole CH), 9.57 (s, 1H, NH); MS (EI, m/z): 399 [M]$^+$; Anal. Calc'd for $C_{23}H_{18}FN_5O$+ 0.19 H$_2$O: C 68.57, H 4.60, N 17.38. Found: C 68.53, H 4.68, N 17.56.

EXAMPLE 10

(5,11-Dihydro-pyrido[2,3-b][1,5]benzodiazepin-10-yl)-[4-fluoro-2-(3-methyl-pyrazol-1-yl)-phenyl]-methanone solvate with 0.20 ethanol The title product was obtained along with its 2-fluoro regioisomer as described in Example 9. The material was further purified by preparative HPLC (Waters silica cartridge, 55:45 hexane-ethyl acetate as the eluant, flow rate 150 mL/min, detection at 254 nm) to give the pure title compound (0.25 g, 10.6%) as a foam which crystallized by sonication from hexane-ethanol, m.p. 180–181° C. MS (EI, m/z): 399 [M]$^+$; Anal. Calc'd for $C_{23}H_{18}FN_5O$+0.20 $C_2H_6O$: C 68.78, H 4.74, N 17.14. Found: C 68.67, H 4.76, N 16.97.

EXAMPLE 11

[2-Chloro-4-(3-methyl-pyrazol-1-yl)-phenyl]-(5-methyl-5,11-dihydro-pyrido[2,3-b[]1,5] benzodiazepin-10-yl)-methanone Step A. (2-Chloro-4-fluoro-phenyl)-(5-methyl-5,11-dihydro-pyrido[2,3-b][1,5]benzodiazepin-10-yl)-methanone Sodium hydride (60% suspension in oil, 0.76 g, 19 mmol) was washed once with hexane, dried under nitrogen and resuspended in dry dimethylformamide (10 mL). A solution of (2-chloro-4-fluorophenyl)-(5,11-dihydro-pyrido [2,3-b][1,5]benzodiazepin-6-yl)-methanone of Example 1, Step D (6.12 g, 17.3 mmol) in dimethylformamide (50 mL) was added dropwise at 0° C. After the gas evolution subsided the cooling bath was removed and stirring was continued at room temperature. Methyl iodide (2.51 g, 17.7 mmol) was added in one portion to the yellow solution, and stirring was continued for 1 hour. The mixture was partitioned between 20% aqueous sodium chloride and dichloromethane. The organic extracts were dried over magnesium sulfate and evaporated to dryness. The residue was dissolved in dichloromethane and absorbed onto a silica Merck-60 flash column. Elution with hexane-ethyl acetate gradient (from 95:5 to 85:15) provided the title product (4.55 g, 72%) as a white crystalline solid, m.p. 222–223° C.

NMR (DMSO-$d_6$, 400 MHz): δ 3.46 (s, 3H, NCH$_3$), 4.37 and 5.67 (2 broad m, 2H, CONCH$_2$), 6.87–6.97 (m, 2H), 7.06–7.14 (m, 2H), 7.20–7.32 (m, 3H), 7.36 (m, 1H), 7.60 (m, 1H), 8.21 (m, 1H); MS (EI, m/z): 367/369 [M]$^+$; (+FAB, m/z): 368/370 [M+H]$^+$; Anal. Calc'd for $C_{20}H_{15}ClFN_3O$: C 65.31, H 4.11, N 11.42. Found: C 65.04, H 4.14, N, 11.27.

Step B. [2-Chloro-4-(3-methyl-pyrazol-1-yl)-phenyl]-(5-methyl-5,11-dihydro-pyrido[2,3-b][1,5]benzodiazepin-10-yl)-methanone Sodium hydride (60% suspension in oil, 0.264 g, 6.6 mmol) was washed with hexane, dried under nitrogen and resuspended in dry dimethylformamide (8 mL). Neat 3-methylpyrazole (0.541 g, 6.6 mmol) was added dropwise at 0° C. After the gas evolution subsided the cooling bath was removed and stirring was continued at room temperature. The (2-chloro-4-fluoro-phenyl)-(5-methyl-5,11-dihydro-pyrido[2,3-b[]1,5]benzodiazepin-10-yl)-methanone of Step A (1.21 g, 3.3 mmol) was added in one portion to the clear solution. The mixture was placed in an oil bath (preheated at 130° C.) for 30 minutes, cooled and partitioned between 20% aqueous sodium chloride and dichloromethane. The organic extracts were dried over magnesium sulfate and evaporated to dryness. The residue was dissolved in dichloromethane and absorbed onto a silica Merck-60 flash column. Elution with hexane-ethyl acetate (gradient from 95:5 to 70:30) provided the less polar title compound (0.936 g, 66%) along with some mixture of 3- and 5-methylpyrazole regioisomers (0.220 g). The title compound crystallized by sonication from hexane-ethanol as a white solid, m.p. 218–219° C. (dec).

NMR (DMSO-$d_6$, 400 MHz): δ 2.21 (s, 3H, pyrazole C—CH$_3$), 3.49 (s, 3H, NCH$_3$), 4.39 and 5.69 (broad dd, 2H, CONCH$_2$), 6.32 (m, 1H, pyrazole CH), 6.88–6.94 (mm, 2H), 7.10 (m, 1H), 7.18–7.24 (m, 1H), 7.26–7.30 (mm, 2H), 7.59–7.65 (m m, 2H), 7.77 (m, 1H), 8.22 (m, 1H), 8.38 (s, 1H, pyrazole CH); MS (EI, m/z): 429/431 [M]$^+$, 219, 195; Anal. Calc'd for $C_{24}H_{20}ClN_5O$: C 67.05, H 4.69, N 16.29. Found: C 67.26, H 4.69, N 16.15.

EXAMPLE 12

(5,11-Dihydro-pyrido[2,3-b][1,5]benzodiazepin-10-yl)-[2-methyl-5-(3-methyl-pyrazol-1-yl)-phenyl]-methanone Step A. 5-Fluoro-2-methyl benzoylchloride A suspension of 5-fluoro-2-methyl benzoic acid (2.31 g, 15.0 mmol) in dichloromethane (30 mL) containing a few drops of dimethylformamide was treated dropwise under nitrogen with oxalyl chloride (1.6 mL, 18.3 mmol). After gas evolution subsided, the reaction mixture was refluxed for an additional 10 minutes, and then evaporated to dryness. The crude acid chloride was used as such in the next step.

Step B. (5,11-Dihydro-pyrido[2,3-b][1,5]benzodiazepin-6-yl)-(5-fluoro-2-methyl-phenyl)-methanone To a solution of 6,11-dihydro-5H-pyrido[2,3-b][1,5] benzodiazepine of Example 1, Step B (2.0 g, 10.1 mmol) in dimethylformamide (15 mL) under nitrogen was added potassium carbonate (4.1 g, 29.7 mmol). The mixture was treated dropwise with a solution of crude 5-fluoro-2-methyl benzoyl chloride of Step A (15.0 mmol) in dimethylformamide (10 mL). After stirring at room temperature for 15 minutes, the mixture was diluted with water and stirred to give a solid mass which was collected by filtration. The solid was dissolved in chloroform and washed with 1 N sodium hydroxide and brine. The organic layer was dried over sodium sulfate and evaporated to dryness to give a purple oil. The crude material was dissolved in dichloromethane and absorbed onto a silica Merck-60 flash column. Elution with 20% ethyl acetate in hexane provided 1.88 g (55.8%) of the title product as a foam which was crystallized by sonication from ethanol-hexane, m.p. 138–140° C.

NMR (DMSO-$d_6$, 400 MHz): δ 1.95 (s, 3H, $CH_3$), 4.11 and 5.46 (dd, 2H, $CONCH_2$), 6.53 (m, 1H), 6.75–6.80 (m, 2H), 6.81–7.06 (m, 4H), 7.24 (m, 1H), 7.60 (m, 1H), 8.11 (m, 1H), 9.57 (s, 1H, NH); MS (EI, m/z): 333 $[M]^+$; Anal. Calc'd for $C_{20}H_{16}FN_3O$: C 72.06, H 4.84, N 12.60. Found: C 71.88, H 4.78, N 12.67.

Step C. (5,11-Dihydro-pyrido[2,3-b][1,5]benzodiazepin-10-yl)-[2-methyl-5-(3-methyl-pyrazol-1-yl)-phenyl]-methanone Sodium hydride (60% suspension in oil, 0.25 g, 6.25 mmol) was washed with hexane, dried under nitrogen and resuspended in dry dimethylformamide (10 mL). Neat 3-methylpyrazole (0.28 mL, 3.5 mmol) was added in one portion at ambient temperature. Stirring was continued until the gas evolution subsided. The 5,11-dihydro-pyrido[2,3-b][1,5]benzodiazepin-6-yl)-(5-fluoro-2-methyl-phenyl)-methanone of Step B (0.75 g, 1.94 mmol) was added in one portion to the clear solution. The mixture was heated to reflux for 26 hours, cooled and partitioned between water and ethyl acetate. The organic extracts were dried over sodium sulfate and evaporated to dryness. The residue was dissolved in dichloromethane and absorbed onto a silica Merck-60 flash column. Elution with hexane-ethyl acetate (gradient from 8:2 to 7:3) provided the title product (0.55 g, 51.5%) as a pale yellow foam which was crystallized by sonication from hexane-ethanol, m.p. 209–210° C.

NMR (DMSO-$d_6$, 400 MHz): δ 1.94 (s, 3H, $CH_3$), 2.23 (s, 3H, pyrazole $CH_3$), 4.13 and 5.49 (dd, 2H, $CONCH_2$), 6.28 (m, 1H, pyrazole CH), 6.50 (m, 1H), 6.78 (m, 2H), 6.97 (m, 1H), 7.07 (m, 1H), 7.24 (m, 1H), 7.51 (m, 1H), 7.62 (m, 1H), 8.11 (m, 1H, pyrazole CH), 8.19 (m, 1H), 9.60 (s, 1H, NH); MS (EI, m/z): 395 $[M]^+$; Anal. Calc'd for $C_{24}H_{21}N_5O$: C 72.89, H 5.35, N 17.71. Found: C 72.57, H 5.49, N 17.46.

EXAMPLE 13

[4-(3-tert-Butyl-pyrazol-1-yl)-2-trifluoromethyl-phenyl]-(5,11-dihydro-pyrido[2,3-b][1,5]benzodiazepin-10-yl)-methanone Sodium hydride (60% suspension in oil, 0.12 g, 3.0 mmol) was washed with hexane, dried under nitrogen and resuspended in dry dimethylformamide (10 mL). 3-tert-butylpyrazole (0.20 g, 1.6 mmol) was added in one portion at ambient temperature, and the stirring was continued until the gas evolution subsided. The (5,11-dihydro-pyrido [2,3-b][1,5]benzodiazepin-6-yl)-[4-fluoro-2-trifluoromethyl-phenyl]-methanone of Example 4, Step B (0.50 g, 1.3 mmol) was added in one portion to the clear solution. The mixture was placed in an oil bath (preheated at 130° C.) for 30 minutes and then heated at reflux for 5 hours. After cooling, the mixture was partitioned between water and ethyl acetate. The organic extracts were dried over sodium sulfate and evaporated to dryness. The crude residue was dissolved in dichloromethane and absorbed onto a silica Merck-60 flash column. Elution with 25% ethyl acetate in hexane provided the title product (0.23 g, 36.0%) as a foam which crystallized by trituration with hexane-ether, m.p. 136–140° C.

NMR (DMSO-$d_6$, 400 MHz): δ 1.26 (s, 9H, $C(CH_3)_3$), 4.17 and 5.45 (dd, 2H, $CONCH_2$), 6.47 (m, 1H, pyrazole CH), 6.54 (m, 1H), 6.68 (m, 1H), 6.80 (m, 1H), 7.00 (m, 1H), 7.28 (m, 1H), 7.60 (m, 1H), 7.87 (m, 1H), 8.04 (m, 1H), 8.13 (m, 1H), 8.47 (m, 1H, pyrazole CH), 9.62 (s, 1H, NH); MS (EI, m/z): 491 $[M]^+$; Anal. Calc'd for $C_{27}H_{24}F_3N_5O$: C 65.98, H 4.92, N 14.25. Found: C 65.75, H 4.92, N 13.95.

EXAMPLE 14

(5,11-dihydro-pyrido[2,3-b][1,5]benzodiazepin-6-yl)-[4-(3-methyl-pyrazol-1-yl)-2-trifluoromethyl-phenyl]-methanone 1:1 salt with trifluoromethanesulfonic acid To a solution of (5,11-dihydro-pyrido[2,3-b][1,5] benzodiazepin-6-yl)-[2-trifluoromethyl-4-(3-methyl-pyrazol-1-yl)-phenyl]-methanone of Example 4, Step C (0.51 g, 1.13 mmol) in dichloromethane (10 mL) was added methanesulfonic acid (0.074 mL, 1.14 mmol). After stirring overnight at room temperature, hexane was added and the precipitate was collected by filtration to give the title salt (0.54 g, 87.6%) as a white solid, m.p. 256–257° C.

MS (+FAB, m/z): 450 $[M+H]^+$; Anal. Calc'd for $C_{24}H_{18}F_3N_5O+CH_4O_3S+0.15\ C_6H_{14}$: C 55.70, H 4.35, N 12.54. Found: C 55.37, H 4.48, N 12.45.

EXAMPLE 15

(5,11-dihydro-pyrido[2,3-b][]1,5]benzodiazepin-6-yl)-[4-(3-methyl-pyrazol-1-yl)-2-trifluoromethyl-phenyl]-methanone 1:1 salt with hydrochloric acid To a solution of (5,11-dihydro-pyrido[2,3-b][1,5] benzodiazepin-6-yl)-[2-trifluoromethyl-4-(3-methyl-pyrazol-1-yl)-phenyl]-methanone of Example 4, Step C (0.55 g, 1.22 mmol) in dichloromethane (10 mL) was added 1N hydrochloric acid in ether (1.22 mL). The mixture was stirred for 1 hour and the precipitate was collected by filtration to give the title salt (0.50 g, 84.1%) as an amorphous white solid.

MS (EI, m/z): 449 $[M]^+$; Anal. Calc'd for $C_{24}H_{18}F_3N_5O+1.04\ HCl+0.10\ CH_2Cl_2$: C 58.38, H 3.91, N 14.12. Found: C 58.23, H 4.07, N 14.03.

EXAMPLE 16

[2-Chloro-4-(3-methyl-pyrazol-1-yl)-phenyl]-(11H-5-oxa-4,10-diaza-dibenzo[a,d]cyclohepten-10-yl)-methanone Step A. 6H-Pyrido[2,3-b][1,5]benzoxazepine Under an atmosphere of nitrogen, lithium aluminum hydride (0.258 g, 6.877 mmol) was added portionwise under stirring to 6H-pyrido[2,3-b][1,5]benzoxazepin-5-one (0.636 g, 3 mmol) in 25 mL of tetrahydrofuran. After heating at reflux for 3 hours, excess lithium aluminum hydride was decomposed by the stepwise addition of 0.3 mL of water, 0.3 mL of 1N sodium hydroxide, 0.9 mL of water, and 3.8 g sodium sulfate. The solids were filtered and washed with ethyl acetate. The filtrate was evaporated under reduced pressure to give crude product (0.45 g) which was purified by flash chromatography (on silica Merck 60, dichloromethane-ethyl acetate, 19:1). The title compound was obtained as a yellow solid (0.10 g, 17%).

NMR (DMSO-$d_6$, 400 MHz): δ 4.32 (d, 2H, $CH_2N$), 6.09 (t, 1H, NH);, 6.56 (t, 1H), 6.62 (d, 1H), 6.82 (t, 1H), 7.00 (d, 1H), 7.18 (m, 1H), 7.79 (d, 1H), 8.165 (m 1H). MS (EI, m/z): 198 $[M]^+$;

Step B. (2-Chloro-4-fluoro-phenyl)-(11H-5-oxa-4,10-diaza-dibenzo[a,d]cyclohepten-10-yl)-methanone Under anhydrous conditions a mixture of 2-chloro-4-fluorobenzoic acid (0.37 g, 2.12 mmol) and oxalyl chloride (0.303 mL, 2.3 mmol) in 10 mL of dichloromethane containing a catalytic amount of dimethylforrnamide was stirred at room temperature until gas evolution ceased. The crude acid chloride solution was then added portionwise to a stirred solution of 6H-pyrido[2,3-b][1,5]benzoxazepine of Step A (0.45 g, 2.12 mmol) and triethylamine (0.35 mL, 2.5 mmol) in 15 mL of dichloromethane. The reaction mixture was stirred overnight at ambient temperature, washed with water and dried over sodium sulfate. Evaporation of the solvent provided the crude title compound as a gummy solid which was used as such in the next step.

NMR (DMSO-$d_6$, 400 MHz): δ 5.1 (broad, 2H, $CH_2N$), 6.9–7.5 (m, 8H), 7.92 (d, 1H), 8.22 (m, 1H); MS (EI, m/z): 354 $[M]^+$, 319, 198, 157.

Step C. [2-Chloro-4-(3-methyl-pyrazol-1-yl)-phenyl]-(11H-5-oxa-4,10-diaza-dibenzo[a,d]cyclohepten-10-yl)-methanone Under an atmosphere of nitrogen, 3-methylpyrazole (0.161 mL, 2.0 mmol) was added to a slurry of hexane washed potassium hydride (0.08 g, 2.0 mmol) in 5 mL of dry dimethylformamide. The mixture was stirred at ambient temperature until gas evolution ceased. A solution of 2-chloro-4-fluoro-phenyl-(11H-5-oxa4,10-diaza-dibenzo[a,d]cyclohepten-10-yl)-methanone of Step B (0.79 g, 2.14 mmol) in 10 mL of dimethylformamide was added. The mixture was heated at 130° C. for 3.5 hours, cooled and partitioned between ethyl acetate and brine. The organic phase was washed with water, dried over sodium sulfate and concentrated to dryness in vacuo. The crude product was purified by flash chromatography (on silica Merck 60, dichloromethane-ethyl acetate gradient from 19:1 to 9:1) to give the title compound as a white solid (0.18 g, 21%), m.p. 220–222° C.

NMR (DMSO-$d_6$, 400 MHz): δ 2.218 (s, 3H, $CH_3$), 5.106 (broad 2H, $CH_2N$), 6.325 (d, 1H), 6.927 (t, 1H), 7.03 (d, 1H), 7.21 (m, 2H), 7.27 (d, 1H), 7.44 (m, 1H), 7,67 (d, 1H), 7.70 (s, 1H), 7.88, (d, 1H), 8.24 (m, 1H), 8.397 (d, 1H). MS (EI, m/z): 416 $[M]^+$, 219.

EXAMPLE 17

[2-Chloro-4-(3-trifluoromethyl-pyrazol-1-yl)-phenyl]-(5,11-dihydro-pyrido[2,3-b[]1,5]benzodiazepin-6-yl)-methanone Sodium hydride (60% suspension in oil, 0.195 g) was washed with hexane, dried under nitrogen and resuspended in dry dimethylformamide (10 mL). 3-trifluoromethyl pyrazole (0.364 g) was added dropwise at 0° C. After the gas evolution subsided the solution was brought to room temperature. The (2-chloro-4-fluorophenyl)-(5,11-dihydro-pyrido [2,3-b][1,5]benzodiazepin-6-y)-methanone of Example 1, Step D (0.787 g, 2.23 mmol) was added in one portion and the mixture was placed in an oil bath (preheated at 130° C.) for 4.5 hours. The mixture was cooled and partitioned between saturated aqueous ammonium chloride and ethyl acetate. The organic extracts were dried over sodium sulfate and evaporated to dryness in vacuo. The residue was dissolved in dichloromethane and absorbed onto a silica Merck-60 flash column. Elution with hexane-ethyl acetate (gradient from 95:5 to 3:2) provided the desired product (0.727 g, 69%) which crystallized by sonication from hexane-ethanol as an off-white solid, m.p. 183–185° C.

NMR (DMSO-$d_6$, 400 MHz): δ 4.16 and 5.45 (dd, 2H, $CONCH_2$), 6.52 (m, 1H), 6.78 (m, 2H), 7.01 (m, 2H), 7.04 (m, 1H, pyrazole CH), 7.26 (m, 1H), 7.61 (m, 1H), 7.74–7.84 (2m, 2H), 8.12 (m, 1H), 8.74 (m, 1H, pyrazole CH), 9.58 (s, 1H, NH); MS (EI, m/z): 469/471 $[M]^+$, 273/275, 196; Anal. Calc'd for $C_{23}H_{15}ClF_3N_5O$: C 58.80, H 3.22, N, 14.91. Found: C 58.67, H 3.14, N 14.83.

EXAMPLE 18

[2-Chloro-4-(1-methyl-1-H-pyrazol-3-yl)-phenyl]-(5,11-dihydro-pyrido[2,3-b][1,5]benzodiazepin-10-yl)-methanone Step A. 2-Chloro-4-(3-dimethylaminopropyl-1-yl)-benzoic acid methyl ester Under an atmosphere of nitrogen, a mixture of 4-bromo-2-chlorobenzoic acid methyl ester (25.13 g, 101 mmol), 1-dimethylamino-2-propyne (16 mL, 150 mmol), bis (triphenylphosphine)palladium(II) chloride (1.0 g) and copper (I) iodide (0.15 g) in 100 mL of triethylamine was heated at 60° C. for 2 hours. The cooled reaction mixture was filtered through Solka floc and the cake was washed with ethyl acetate. The filtrate was partitioned between ethyl acetate and dilute aqueous sodium thiosulfate. The organic layer was washed with water, brine and dried over sodium sulfate. The dark solution was filtered through a plug of Merck-60 silica gel and the filtrate was concentrated in vacuo to give the title compound (23.8 g, 95% ) as an orange oil, which was used as such in the next step.

NMR (DMSO-$d_6$, 300 MHz): δ 2.25 (s, 6H, $NCH_3$), 3.475 (s, 2H, $CCH_2N$), 3.84 (s, 3H, $OCH_3$), 7.5 (dd, 1H), 7.62 (s, 1H), 7.8 (d, 1H).

Step B. 2-Chloro-4-(3-dimethylamino-2-propen-1-yl)-benzoic acid methyl ester

Under an atmosphere of nitrogen, purified meta-chloroperbenzoic acid (16.0 g, 93 mmol) was added portionwise to a stirred solution of 2-chloro-4-(3-dimethylaminopropyl-1-yl)-benzoic acid methyl ester of Step A (23.5 g, 93.4 mmol) in 200 rnL of dichloromethane at −10° C. After the addition was complete, the solution was stirred at reduced temperature for 30 minutes and then filtered through a column of basic alumina (400 g, Brockman activity I) packed with dichloromethane-methanol (9:1, v/v). The intermediate N-oxide was eluted with the above solvent system. The dichloromethane was then carefully replaced with methanol by evaporation at or below room temperature, taking care that the mixture is never allowed to evaporate to dryness. The methanolic solution was heated at 60° C. overnight, and then was concentrated in vacuo. The residue was purified by flash chromatography (on Merck-60 silica gel, hexane-ethyl acetate 1:1) to give 12.1 g of a slightly impure product. Trituration with diethyl ether provided the pure title compound (6.15 g, 48%) as an orange solid.

NMR (DMSO-d$_6$, 300 MHz): δ 2.98 (s, 3H, NCH$_3$), 3.2 (s, 3H, NCH$_3$), 3.83 (s, 3H, OCH$_3$), 5.85 (d, 1H, vinyl H), 7.75–8.0 (m, 4H, vinyl H+ArH).

Step C. 2-Chloro-4-(1H-pyrazol-3-yl)-benzoic acid methyl ester

A solution of 2-chloro-4-(3-dimethylamino-2-propen-1-yl)-benzoic acid methyl ester of Step B (6.13 g, 22.9 mmol) and anhydrous hydrazine (1.44 mL, 45.8 mmol) in 15 mL of glacial acetic acid was heated at 90° C. for 30 minutes. The reaction mixture was concentrated in vacuo and the residue partitioned between ethyl acetate and water. The organic layer was washed with water and brine and dried over sodium sulfate. The solvent was evaporated and the residual solid triturated with diethyl ether-hexane to give the title compound (5.1 g, 94% ) as an orange solid.

NMR (DMSO-d$_6$, 300 MHz): δ 3.85 (s, 3H, OCH$_3$), 6.9 (d, 1H), 7.9 (m, 3H), 8.0 (d, 1H), 13.15 (broad, 1H, NH).

Step D. 2-Chloro-4-(1-methyl-1H-pyrazol-3-yl)-benzoic acid methyl ester

Under an atmosphere of nitrogen, a solution of 2-chloro-4-(1H-pyrazol-3-yl)-benzoic acid methyl ester of Step C (5.0 g, 21.1 mmol) in 50 mL of dry dimethylformamide was added dropwise to a stirred mixture of hexane washed sodium hydride (0.51 g, 21.1 mmol) in 5 mL of dry dimethylformamide. The mixture was stirred at ambient temperature for 30 minutes, methyl iodide (2.7 mL, 42.2 mmol) was added to the resulting solution and the stirring was continued overnight at room temperature. The reaction mixture was poured into water and extracted with ethyl acetate. The organic layer was washed with water, brine and dried over sodium sulfate. Removal of solvent in vacuo afforded 4.8 g of an orange oil. Flash chromatography of the crude material (on silica gel Merck-60, hexane-ethyl acetate, 4:1) provided 2.9 g (55%) of the desired 1-methylpyrazole regioisomer.

NMR (DMSO-d$_6$, 300 MHz): δ 3.84 (s, 3H, CH$_3$), 3.9 (s, 3H CH$_3$), 6.875 (d, 1H), 7.8 (d, 1H), 7.85 (s, 2H), 7.95 (s, 1H).

Step E. 2-Chloro-4-(1-methyl-1H-pyrazol-3-yl)-benzoic acid

A solution of 2-chloro-4-(1-methyl-1H-pyrazol-3-yl)-benzoic acid methyl ester of Step D (2.9 g, 11.6 mmol) in 20 mL of methanol containing 5 mL of 2.5 N sodium hydroxide was stirred at ambient temperature overnight. An additional 2.0 mL of 2.5 N sodium hydroxide were added and the solution was gently heated for 30 minutes. The reaction mixture was concentrated in vacuo, diluted with water, and acidified with 2N hydrochloric acid. The precipitate was collected and thoroughly dried to give 2.55 g (93%) of the title compound.

NMR (DMSO-d$_6$, 300 MHz): δ 3.9 (s, 3H, NCH$_3$), 6.85 (d, 1H), 7.82 (m, 3H), 7.95 (s, 1H), 13.3 (broad, 1H, COOH).

Step F. [2-Chloro-4-(1-methyl-1H-pyrazol-3-yl)-phenyl]-(5,11-dihydro-pyrido[2,3-b][1,5]benzodiazepin-10-yl)-methanone Under anhydrous conditions a solution of 2-chloro-4-(1-methyl-1H-pyrazol-3-yl)-benzoic acid of Step E (2.1 g, 8.88 mmol) and triethylamine (1.3 mL, 9.2 mmol) in 75 mL of dichloromethane was treated in one portion with 2,4,6-trichlorobenzoyl chloride (1.48 mL, 9.2 mmol) and stirred at ambient temperature for 2 hours. To the solution was added the 6,11-dihydro-5H-pyrido[2,3-b][1,5]benzodiazepine of Example 1, Step B (1.74 g, 8.9 mmol) followed by 4-dimethylaminopyridine (1.1 g, 8.9 mmol) and stirring was continued for 18 hours. The reaction mixture was washed sequentially with saturated sodium bicarbonate and brine. After drying over sodium sulfate, the solution was concentrated to small volume and absorbed onto silica Merck-60. Elution with ethyl acetate-hexane (gradient from 4:3 to 2:1) gave the pure title compound as a syrup which crystallized from diethylether. The white solid (0.78 g, 23% yield based on recovered starting material) melted at 196–197° C.

NMR (DMSO-d$_6$, 400 Mhz): δ 3.831 (s, 3H, NCH$_3$), 4.13 (d, 1H), 5.43 (d, 1H), 6.497 (t, 1H), 6.71 (d, 1H), 6.76 (m, 2H), 6.97 (t, 1H), 7.24 (d, 1H), 7.6 (m, 3H), 7.705 (d, 1H), 8.10(dd, 1H), 9.544 (s, 1H, NH); MS (EI, m/z): 415/417 [M]$^+$, 219/221; Anal. Calc'd for C$_{23}$H$_{18}$ClN$_5$O: C 66.42, H 4.36, N 16.84. Found: C 66.20, H 4.49, N 16.59.

EXAMPLE 19

[2-Chloro-4-(1-methyl-1H-pyrazol-3-yl)-phenyl]-(5,11-dihydro-pyrido[2,3-b][1,5]benzodiazepin-10-yl)-methanone Under anhydrous conditions a mixture of the 2-chloro-4-(1-methyl-1H-pyrazol-3-yl)-benzoic acid of Example 18, Step E (1.9 g, 8.05 mmol) and oxalyl chloride (0.79 mL, 9.0 mmol) in 20 mL of dichloromethane containing a catalytic amount of dimethylformamide was stirred at ambient temperature for 1 hour. The solvent was evaporated and the solid acid chloride was dissolved in 5 mL of dimethylformamide and added directly to a mixture of 6,11-dihydro-5H-pyrido [2,3-b][1,5]benzodiazepine of Example 1, Step B (1.59 g, 8.05 mmol) and potassium carbonate (1.25 g, 9.0 mmol). After stirring for 2 hours at ambient temperature the reaction mixture was partitioned between ethyl acetate and water. The organic phase was washed with water and brine, dried over sodium sulfate, and concentrated to small volume. Flash chromatography of the residue (on silica Merck 60, ethyl acetate-hexane, gradient from 4:3 to 2: 1) gave the product as a syrup which crystallized from diethyl ether (1.8 g, 61% yield, based on recovered starting material) as a white solid, m.p. 196–197° C. Another recrystallization from ethanol-diethyl ether provided a higher melting polymorph, m.p. 202° C. as determined by differential scanning calorimetry.

MS (+FAB, m/z): 416/418 (M+H)$^+$. Anal. Calc'd for C$_{23}$H$_{18}$ClN5O: C 66.42, H 4.36, N 16.84. Found: C 66.20, H 4.42, N 16.80.

EXAMPLE 20

[2-Chloro-4-(1-methyl-1H-pyrazol-3-yl)-phenyl]-(5-methyl-5,11-dihydro-pyrido[2,3-b][1,5] benzodiazepin-10-yl)-methanone Under anhydrous conditions, a solution of [2-chloro-4-(1-methyl-1H-pyrazol-3-yl)-phenyl]-(5,11-dihydro-pyrido [2,3-b][1,5]benzodiazepin-10-yl)-methanone of Example 19 (0.382 g, 0.92 mmol) in 10 mL of tetrahydrofuran was added dropwise to a stirred slurry of hexane washed sodium hydride (0.025 g, 1.02 mmol) in 2 mL of tetrahydrofuran. After the gas evolution ceased, methyl iodide (1 mL) was added and stirring was continued for 2 hours. The reaction mixture was partitioned between ethyl acetate and water. The organic layer was washed with brine and dried over sodium sulfate. The solvent was removed and the crude product purified by flash chromatography (on silica Merck-60, dichloromethane-ethyl acetate 2:1) to give the title compound (0.18 g, 47%). Crystallization from diethylether provided a light yellow solid (0.16 g), m.p. 249–250° C.

NMR (DMSO-d$_6$, 400 MHz): δ 3.491 (s, 3H NCH$_3$), 3.835 (s, 3H, NCH$_3$), 4.18 (broad, 1H), 5.7 (broad, 1H), 6.497 (t, 1H), 6.72 (d, 1H), 6.88 (m, 2H), 7.08 (d, 1H), 7.19 (m, 2H), 7.25 (d, 1H), 7.6 (m, 2H), 7.69 (d, 1H), 7.71 (d, 1H), 8.215 (dd, 1H). MS (EI, m/z): 429/431 [M]$^+$, 219/221.

EXAMPLE 21

[2-Chloro-4-(3-methyl-pyrazol-1-yl)-phenyl]-(5,11-dihydro-pyrido [2,3-b][1,5]benzodiazepin-6-yl)-methanone Step A. 2-Chloro-4-(3-methyl-1H-pyrazol-1-yl)-benzoic acid methyl ester Under anhydrous conditions a stirred suspension of hexane washed potassium hydride (0.424 g, 10.6 mmol) in 5 mL of dimethylformamide was treated in one portion with 3-methyl pyrazole (0.85 mL, 10.6 mmol). After the gas evolution ceased, 2-chloro-4-fluorobenzoic acid methyl ester (2.0 g, 10.6 mmol) was added to the clear solution. The mixture was heated at 130° C. for 15 minutes, cooled, and partitioned between ethyl acetate and brine. The organic layer was washed with water and brine, and dried over sodium sulfate. Removal of solvent afforded 2.2 g of a yellow oil consisting of a mixture of 3-methyl and 5-methylpyrazole regioisomers. In addition, about 20% of the acid derived from hydrolysis of the ester was detected by analysis of the NMR spectrum of the crude product. The desired 3-methylpyrazole regioisomer was separated from the 5-methyl isomer of Example 22 by flash chromatography (on silica Merck-60, dichloromethane-hexane 2:1) and was isolated as a white solid (1.55 g, 56%).

NMR (DMSO-d$_6$, 400 MHz): δ 2.264 (s, 3H, CCH$_3$), 3.845 (s, 3H, OCH$_3$), 6.40 (d, 1H), 7.865 (dd, 1H), 7.93 (d, 1H), 8.00 (s, 1H), 8.535 (d, 1H). MS (EI, m/z): 250/252 [M]$^+$, 219.

Step B. 2-Chloro-4-(3-methyl-1H-pyrazol-1-yl)-benzoic acid

A solution of 2-chloro-4-(3-methyl-1H-pyrazol-1-yl)-benzoic acid methyl ester of Step A (1.42 g, 5.6 mmol) in 20 mL of tetrahydrofuran containing 6 mL of 1 M aqueous lithium hydroxide was stirred overnight at ambient temperature. The reaction mixture was partitioned between ethyl acetate and 1 N hydrochloric acid. The organic layer was washed with water and brine, and dried over sodium sulfate. Evaporation of the solvent afforded the title compound (1.05 g, 78%), m.p. 192–193° C.

NMR (DMSO-d$_6$, 400 MHz): δ 2.268 (s, 3H, CCH$_3$), 6.40 (d, 1H), 7.84 (dd, 1H), 7.92 (d, 1H), 8.00 (s, 1H), 8.53 (d, 1H), 13.32 (broad, 1H, COOH); MS (EI, m/z): 236/238 [M]$^+$, 219; Anal. Calc'd for C$_{11}$H$_9$ClN$_2$O$_2$: C, 55.83, H 3.83, N 11.84. Found: C 55.79, H 3.98, N 11.73.

Step C. [2-Chloro-4-(3-methyl-pyrazol-1-yl)-phenyl]-(5,11-dihydro-pyrido[2,3-b][1,5]benzodiazepin-6-yl)-methanone In the manner of Example 5, Step D, employing 2-chloro-4-(3-methyl-1H-pyrazol-1-yl)-benzoic acid of Step B (0.971 g, 4.1 mmol), triethylamine (0.57 mL, 4.1 mmol), 1,3,5-trichlorobenzoylchloride (0.63 mL, 4.0 mmol), 6,11-dihydro- 5H-pyrido[2,3-b][1,5]benzodiazepine of Example 1, Step B (0.67 g, 3.4 mmol) and 4-dimethylamino pyridine (0,42 g, 3.4 mmol) in dichloromethane (20 mL), was obtained a compound identical to that of Example 1.

EXAMPLE 22

2-Chloro-4-(5-methyl-1H-pyrazol-1-yl)-benzoic acid methyl ester

The title compound was prepared as described in Example 21, Step A and separated from the 3-methylpyrazole isomer of Example 21 by flash chromatography (on silica Merck-60, eluant: dichloromethane). It was obtained as a white solid (0.20 g, 7.5%).

NMR (DMSO-d$_6$, 400 Mhz): δ 2.425 (s, 3H, CCH$_3$), 3.875 (s, 3H, OCH$_3$), 6.33 (s, 1H), 7.65 (m, 2H), 7.79 (s, 1H), 7.95 (d, 1H). MS (EI, m/z): 250/252 [M]$^+$, 219.

EXAMPLE 23

(2-Chloro-4-fluorophenyl)-(5,11-dihydro-pyrido[2,3-b[]1,5]benzodiazepin-6-yl-methanone To a solution of 6,11-dihydro-5H-benzo[b]pyrido[2,3-e][1,4]diazepine of Example 1, Step B (0.100 g, 0.51 mmol) in tetrahydrofuran (5 mL) was added 4-dimethylamino pyridine (0.190 g, 1.55 mmol) followed by 2-chloro-4-fluoro benzoylchloride (0.100 mL, 0.76 mmol). The mixture was stirred overnight at room temperature and then evaporated to dryness. The residue was partitioned between aqueous saturated ammonium chloride and dichloromethane. The organic layer was dried over sodium sulfate and evaporated to dryness to provide the title compound identical to the material described in Example 1, Step D.

EXAMPLE 24

[2-Chloro-4-(5-methyl-1H-[1,2,4]triazol-3-yl)-phenyl]-(5,11-dihydro-pyrido[2,3-b][1,5] benzodiazepin-6-yl)-methanone Step A. 2-Chloro-terephthalamic acid methyl ester A mixture of 2-chloro-4-cyano benzoic acid methyl ester (12.4 g, 63.4 mmol) and potassium carbonate (1.3 g, 9.4 mmol) in dimethylsulfoxide (40 mL) was treated dropwise under cooling with 30% hydrogen peroxide (7.6 mL). The mixture was allowed to warm to room temperature and stirred overnight. The solution was quenched with water and the resulting precipitate collected by filtration. The crude material was dissolved in dichloromethane and absorbed on a silica gel Merck-60 flash column. Elution with a dichloromethane-methanol gradient (from 98:2 to 90:10) provided the title compound (10 g, 74%) as a white solid, m.p. 154–156° C.

NMR (DMSO-d$_6$, 400 MHz): δ 3.87 (s, 3H), 7.67 (s, 1H, NH);, 7.86–7.91 (m, 2H), 8.00–8.01 (m, 1H), 8.20 (s, 1H, NH); MS (EI, m/z): 213 [M]$^+$; Anal. Calc'd for C$_9$H$_8$ClNO$_3$: C 50.60, H 3.77, N 6.56. Found: C 50.36, H 3.66, N 6.44.

Step B. 2-Chloro N-(1-dimethylaminoethylidene)-terephthalamic acid methyl ester

A mixture of 2-chloro-terephthalamic acid methyl ester of Step A (1.02 g, 4.8 mmol) and N,N -dimethylacetamide dimethyl acetal (3.5 mL, 23.9 mmol) was heated at 90° C. for 30 minutes under nitrogen. The solution was cooled, and excess reagent was removed under high vacuum to provide a brown oil which was used as such in the next step.

NMR (DMSO-d$_6$, 400 MHz): δ 2.29 (s, 3H), 3.14 (s, 3H), 3.16 (s, 3H), 3.87 (s, 3H), 7.83–7.85 (m, 1H), 8.00–8.06 (m, 2H); MS (EI, m/z): 282 [M]$^+$;

Step C. 2-Chloro-4-(5-methyl-1H-[1,2,4]triazol-3-yl)-benzoic acid methyl ester

Anhydrous hydrazine (0.30 mL, 9.6 mmol) was added via syringe to a solution of the intermediate of Step B (4.8 mmol) in glacial acetic acid (6 mL) under a nitrogen atmosphere. The reaction was heated at 90° C. for 30 minutes, then cooled and concentrated in vacuo to a light brown solid. The solid was redissolved in aqueous methanol and the solution neutralized with saturated aqueous sodium bicarbonate. The mixture was extracted with dichloromethane and ethyl acetate, the extracts were combined and dried over sodium sulfate. Evaporation of the solvents yielded a solid which was triturated with ether to provide the title product (0.81 g, 67%) as an off-white solid, m.p. 196–198° C.

NMR (DMSO-$d_6$, 400 MHz): δ 2.41 (s, 3H), 3.86 (s, 3H), 7.90–8.05 (m, 3H), 13.94 (s, 1H); MS (EI, m/z): 251 [M]$^+$; Anal. Calc'd for $C_{11}H_{10}ClN_3O_2$: C 52.50, H 4.01, N, 16.70. Found: C 52.68, H 3.83, N 16.50.

Step D. 2. Chloro-4-[1-(4-methoxy-benzyl)-5-methyl-1H-[1,2,4]triazol-3-yl]-benzoic acid methyl ester 0.03 solvate with dichloromethane Sodium hydride (60% suspension in oil, 0.30 g, 7.5 mmol) was washed with hexane and resuspended in dry dimethylformamide (20 mL) under a nitrogen atmosphere. The triazole intermediate of Step C (1.36 g, 5 mmol) was added and the mixture was stirred for one hour. p-Methoxybenzyl chloride (0.75 mL, 5.5 mmol) was added and after stirring for 3 hours, the reaction was quenched with water and extracted with ethyl acetate. The extracts were combined, dried over anhydrous sodium sulfate and concentrated in vacuo. The residue was dissolved in dichloromethane and absorbed on a silica Merck 60 flash column. Elution with 3% ethyl acetate in dichloromethane provided the title compound (1.23 g, 666.2%) as a white solid, m.p. 102–104° C.

NMR (DMSO-$d_6$, 400 MHz): δ 2.48 (s, 3H), 3.72 (s, 3H), 3.86 (s, 3H), 5.35 (s, 2H), 6.90–6.92 (m, 2H), 7.23–7.25 (m, 2H), 7.89–8.02 (m, 3H); MS (EI, m/z): 371 [M]$^+$; Anal. Calc'd for $C_{19}H_{18}ClN_3O_3$+0.03 $CH_2Cl_2$: C 61.05, H 4.86, N 11.22. Found: C 60.83, H 4.96, N, 11.18.

Step E. 2-Chloro-4-[1-(4-methoxy-benzyl)-5-methyl-1H-[1,2,4]-triazol-3-yl]-benzoic acid 0.10 hydrate 0.04 solvate with ethyl acetate A solution of the ester intermediate of Step D (1.6 g, 4.3 mmol) in methanol (15 mL) was treated with 2.5 N aqueous sodium hydroxide (3.5 mL, 8.8 mL) under a nitrogen atmosphere. The mixture was refluxed for two hours, cooled and concentrated in vacuo. The residue was partitioned between ethyl acetate and water. The aqueous layer was acidified with IN aqueous HCl. The precipitate was collected by filtration to provide the title compound (1.25 g, 81.2%) as a white solid, m.p. 154–156° C.

NMR (DMSO-$d_6$, 400 MHz): δ 2.47 (s, 3H), 3.72 (s, 3H), 5.34 (s, 2H), 6.90–6.93 (m, 2H), 7.23–7.25 (m, 2H), 7.87–7.99 (m, 3H), 13.40 (s, 1H); MS (EI, m/z): 357 [M]$^+$; Anal. Calc'd for $C_{18}H_{16}ClN_3O_3$+0.10 $H_2O$+0.04 $C_4H_8O_2$: C 60.07, H 4,59, N 11.57; Found: C 59.75, H 4.41, N 11.43.

Step F. 2-Chloro-4-[1-(4-methoxy-benzyl)-5-methyl-1H-[1,2,4]-triazol-3-yl]-benzoyl chloride A suspension of the acid of Step E (1 g, 2.8 mmol) in dichloromethane containing a few drops of dimethylformamide was treated dropwise under nitrogen with oxalyl chloride (0.30 mL, 3.4 mmol). After gas evolution subsided, the reaction mixture was refluxed for another 15 minutes and then evaporated to dryness in vacuo to provide the title compound which was used as such in the next step.

Step G. {2-Chloro-4-[1-(4-methoxy-benzyl)-5-methyl-1H-[1,2,4]triazol-3-yl]-phenyl}-(5,11-dihydro-pyrido[2,3-b][1,5]benzodiazepin-6-yl)-methanone 0.06 dichloromethane solvate To a solution of 6,11-dihydro-5H-pyrido[2,3-b][1,5] benzodiazepine of Example 1, Step B (0.55 g, 2.8 mmol) in dimethylformamide (10 mL) under nitrogen was added solid potassium carbonate (0.39 g, 2.8 mmol). The mixture was treated dropwise with a solution of the crude acid chloride (2.8 mmol) of Step F in dimethylformamide (10 mL). After stirring at room temperature for 90 minutes, the reaction mixture was diluted with water and extracted with ethyl acetate. The organic extracts were combined and washed with 1N aqueous sodium hydroxide, dried over sodium sulfate and evaporated to dryness. The residue was dissolved in dichloromethane and absorbed on a column of flash silica Merck-60. Less polar impurities were eluted with 1:1 ethyl acetate-hexane. Further elution with 2% methanol in dichloromethane provided the title compound as a white solid (0.57 g, 38%), m.p. 218–221° C.

NMR (DMSO-$d_6$, 400 MHz): δ 2.42 (s, 3H), 3.71 (s, 3H), 4.14 and 5.44 (dd, 2H), 5.29 (s, 2H), 6.49 (m, 1H), 6.74–6.80 (m, 2H), 6.88–6.99 (m, 3H), 7.18–7.26 (m, 4H), 7.60 (m, 1H), 7.65–7.75 (m, 2H, ArH), 8.11 (m, 1H), 9.55 (s, 1H); MS (ESI, m/z): 537 [M+H]$^+$; Anal. Calc'd for $C_{30}H_{25}ClO_2$+ 0.06 $CH_2Cl_2$: C 66.60, H 4.67, N 15.50. Found: C 66.24, H 4.85, N 15.23.

Step H. [2-Chloro-4-(5-methyl-1H-[1,2,4]-triazol-3-yl)-phenyl]-(5,11-dihydro-pyrido[2,3-b][1,5]benzodiazepin-6-yl)-methanone A solution of the triazole intermediate of Step G (0.54 g, 1.01 mmol) in trifluoroacetic acid (15 mL) was heated at reflux for seven days under a nitrogen atmosphere. The mixture was cooled and the trifluoroacetic acid removed in vacuo. The residue was dissolved in water and neutralized with saturated aqueous sodium bicarbonate. The mixture was extracted with ethyl acetate, the extracts were dried over sodium sulfate and concentrated in vacuo to give a pale yellow solid. The residue was dissolved in ethyl acetate-methanol and absorbed on a silica Merck-60 flash column. Elution with a solvent gradient (from 100% ethyl acetate to 5% methanol in ethyl acetate) provided the title compound (0.23 g, 54.6%) as a white solid, m. p. >270° C.

NMR (DMSO-$d_6$, 400 MHz): δ 2.36 (s, 3H), 4.15 and 5.45 (dd, 2H, CONCH$_2$), 6.50 (m, 1H), 6.75–6.80 (m, 2H), 6.98 (m, 1H), 7.19–7.27 (m, 2H), 7.60 (m, 1H), 7.70–7.79 (m, 2H), 8.11 (m, 1H), 9.54 (s, 1H), 13.78 (s, 1H); MS (+FAB, m/z): 417 [M+H]$^+$; Anal. Calc'd for $C_{22}H_{17}ClN_6O$: C 63.39, H 4.11, N 20.16. Found: C 63.14, H 4.13, N, 19.90.

EXAMPLE 25

[2-Bromo-4-(3-methyl-pyrazol-1-yl)-phenyl]-(11H-5-oxa-4,10-diaza-dibenzo[a,d]cyclohepten-10-yl)-methanone The title compound may be prepared in a manner analogous to that of the 2-chloro analog of Example 16, by reacting 6H-pyrido[2,3-b][1,5]benzoxazepine of Example 16, Step A, with 2-bromo-4-fluorobenzoyl chloride of Example 3, Step A. Subsequent reaction of the intermediate (2-bromo-4-fluoro-phenyl)-(11H-5-oxa-4,10-diaza-dibenzo [a,d]cyclohepten-10-yl)-methanone with the sodium salt of 3-methylpyrazole in a manner analogous to that of Example 16, Step C will provide the title compound.

EXAMPLE 26

[4-(3-Methyl-pyrazol-1-yl)-2-trifluoromethyl-phenyl]-(11H-5-oxa-4,10-diaza-dibenzo[a,d]cyclohepten-10-yl)-methanone The title compound may be prepared in a manner analogous to that of the 2-chloro analog of Example 16, by reacting 6H-pyrido[2,3-b][1,5]benzoxazepine of Example 16, Step A with 2-trifluoromethyl-4-fluorobenzoyl chloride of Example 4, Step A. Subsequent reaction of the intermediate (4-fluoro-2-trifluoromethyl-phenyl)-(11H-5-oxa-4,10-diaza-dibenzo[a,d]cyclohepten-10-yl)-methanone with the sodium salt of 3-methylpyrazole in a manner analogous to that of Example 16, Step C will provide the title compound.

EXAMPLE 27

[2-Fluoro-4-(3-methyl-pyrazol-1-yl)-phenyl]-(11H-5-oxa-4,10-diaza-dibenzo[a,d]cyclohepten-10-yl)-methanone The title compound may be prepared in a manner analogous to that of the 2-chloro analog of Example 16, by reacting 6H-pyrido[2,3-b][1,5]benzoxazepine of Example 16, Step A with 2,4-difluoro benzoylchloride of Example 9, Step A. Subsequent reaction of the intermediate (2,4-difluoro-phenyl)-(11H-5-oxa-4,10-diaza-dibenzo[a,d]cyclohepten-10-yl)-methanone with the sodium salt of 3-methylpyrazole in a manner analogous to that of Example 16, Step C will provide the title compound.

EXAMPLE 28

[2-Chloro-4-(1-methyl-1H-pyrazol-3-yl)-phenyl]-(11H-5-oxa-4,10-diaza-dibenzo[a,d]cyclohepten-10-yl)-methanone The title compound may be prepared in a manner analogous to that of the pyrazole analog of Example 19, by reacting the intermediate 2-chloro-4-(1-methyl-1H-pyrazol-3-yl)-benzoylchloride of Example 19 with 6H-pyrido[2,3-b][1,5]benzoxazepine of Example 16, Step A.

What is claimed:
1. A compound of the formula (I):

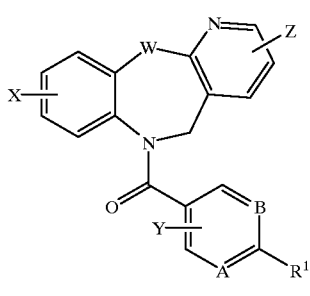

(I)

wherein:

W is $NR^6$

A and B are, independently, carbon or nitrogen;

$R^1$ is —C≡C—$R^9$, alkanoyl of 2 to 7 carbon atoms or a moiety selected from the group of:

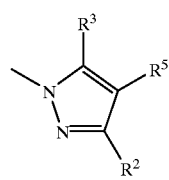

(a)

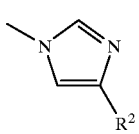

(b)

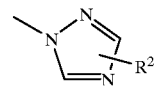

(c)

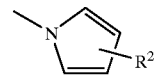

(d)

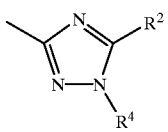

(e)

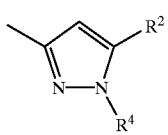

(f)

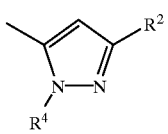

(g)

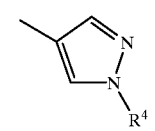

(h)

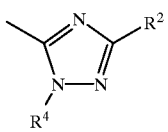

(i)

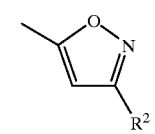

(j)

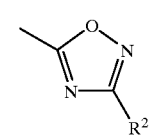

(k)

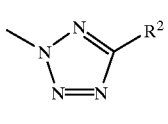

(l)

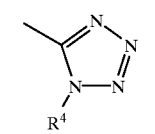

(m)

-continued

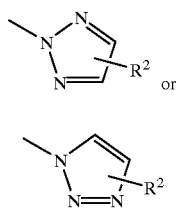

(n)

(o)

R², R³ and R⁵ are, independently, hydrogen, straight chain alkyl of 1 to 6 carbon atoms, branched chain alkyl of 3 to 7 carbon atoms, cycloalkyl of 3 to 7 carbon atoms, or perfluoroalkyl of 1 to 6 carbons;

R⁴ is hydrogen, straight chain alkyl of 1 to 6 carbon atoms, branched chain alkyl of 3 to 7 carbon atoms, cycloalkyl of 3 to 7 carbon atoms, alkoxyalkyl of 2 to 7 carbon atoms, optionally substituted aralkyl of 7 to 12 carbon atoms, or an acyl substituent selected from the group consisting of alkanoyl of 2 to 7 carbon atoms, alkenoyl of 3 to 7 carbon atoms, cycloalkanoyl of 3 to 7 carbon atoms, arylalkanoyl having an alkane chain of from 1 to 6 carbon atoms, aroyl or heteroaroyl of 7 to 13 carbon atoms;

R⁶ is hydrogen, acyl of 2 to 6 carbon atoms, straight chain alkyl of 1 to 6 carbon atoms, or branched chain alkyl of 3 to 7 carbon atoms;

X and Y are, independently, hydrogen, straight chain alkyl of 1 to 6 carbon atoms, branched chain alkyl of 3 to 7 carbon atoms, cycloalkyl of 3 to 7 carbon atoms, alkoxyalkyl of 2 to 7 carbon atoms, halogen, straight or branched chain alkoxy of 1 to 6 carbon atoms, hydroxy, CF₃, or perfluoroalkyl of 2 to 6 carbons;

Z is hydrogen or a straight chain alkyl group of 1 to 6 carbon atoms, branched chain alkyl of 3 to 7 carbon atoms, cycloalkyl of 3 to 7 carbon atoms, halogen, alkoxyalkyl of 2 to 7 carbons, or hydroxyalkyl of 1 to 6 carbons, or CH₂NR⁷R⁸;

R⁷ and R⁸ are, independently, hydrogen, straight chain alkyl of 1 to 6 carbon atoms, branched chain alkyl of 3 to 7 carbon atoms, aryl, or arylalkyl; or taken together with the nitrogen they form a five or six membered ring optionally containing one or more additional heteroatoms;

R⁹ is independently, hydrogen, a silyl containing group, or a lower alkyl of 1 to 6 carbons;

or a pharmaceutically acceptable salt or ester form thereof.

2. A compound of claim 1 wherein R⁷ and R⁸ taken together are a five or six membered ring selected from the group:

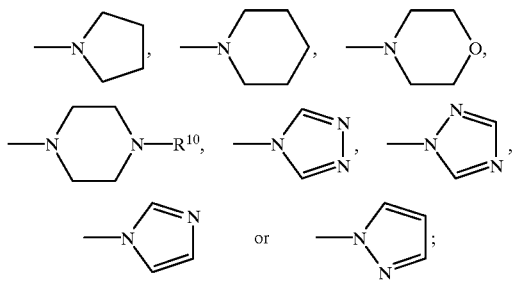

or a pharmaceutically acceptable salt or ester form thereof.

3. A compound selected from Formula (I):

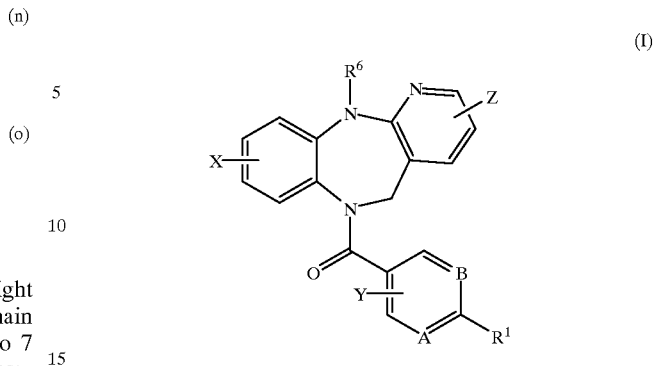

(I)

wherein:

R¹ is alkanoyl of 2 to 7 carbon atoms or a group selected from

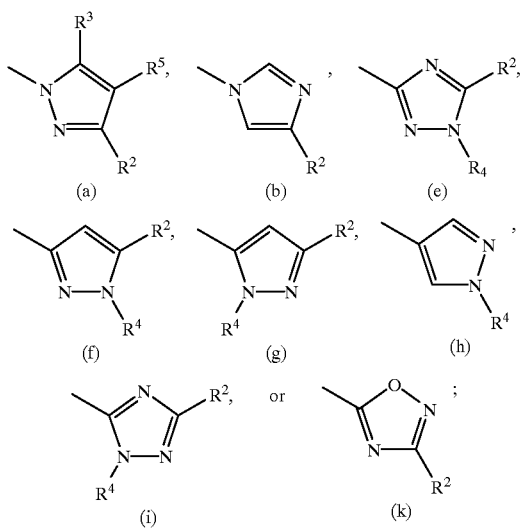

R², R³ and R⁵ are, independently, hydrogen, straight chain alkyl of 1 to 6 carbon atoms, branched chain alkyl of 3 to 7 carbon atoms, cycloalkyl of 3 to 7 carbon atoms, or perfluoroalkyl of 1 to 6 carbons;

R⁴ is hydrogen, straight chain alkyl of 1 to 6 carbon atoms, branched chain alkyl of 3 to 7 carbon atoms, cycloalkyl of 3 to 7 carbon atoms, alkoxyalkyl of 2 to 7 carbon atoms, optionally substituted aralkyl of 7 to 12 carbon atoms, or an acyl substituent selected from the group consisting of alkanoyl of 2 to 7 carbon atoms, alkenoyl of 3 to 7 carbon atoms, cycloalkanoyl of 3 to 7 carbon atoms, aroyl or heteroaroyl of 7 to 12 carbon atoms optionally substituted with one or two alkyl groups of 1 to 6 carbon atoms;

R⁶ is hydrogen, acyl of 2 to 6 carbon atoms, straight chain alkyl of 1 to 6 carbon atoms, or branched chain alkyl of 3 to 7 carbon atoms;

X and Y are, independently, hydrogen, straight chain alkyl of 1 to 6 carbon atoms, branched chain alkyl of 3 to 7 carbon atoms, cycloalkyl of 3 to 7 carbon atoms, alkoxyalkyl of 2 to 7 carbon atoms, halogen, straight or branched chain alkoxy of 1 to 6 carbons, hydroxy, CF₃, or perfluoroalkyl of 2 to 6 carbons;

R⁷ and R⁸ are, independently, hydrogen, straight chain alkyl of 1 to 6 carbon atoms, branched chain alkyl of 3 to 7 carbon atoms or taken together with the nitrogen they form a five or six membered ring optionally containing one or more additional heteroatoms;

or a pharmaceutically acceptable salt or ester form thereof.

4. A compound of claim 3 wherein $R^7$ and $R^8$ taken together are a five or six membered ring selected from the group:

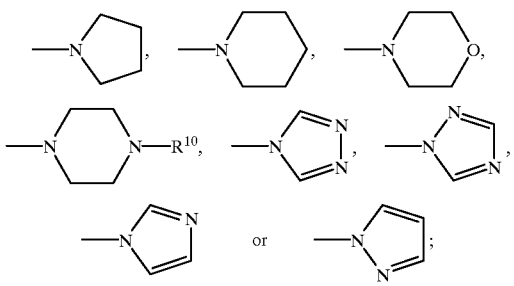

or a pharmaceutically acceptable salt or ester form thereof.

5. A compound of claim 1 which is [2-Chloro-4-(3-methyl-pyrazol-1-yl)-phenyl]-(5,11-dihydro-pyrido[2,3-b][1,5]benzodiazepin-6-yl)-methanone.

6. A compound of claim 1 which is [2-Chloro-4-(5-methyl-pyrazol-1-yl)-phenyl]-(5,11-dihydro-pyrido[2,3-b][1,5]benzodiazepin-6-yl)-methanone.

7. A compound of claim 1 which is [2-Bromo-4-(3-methyl-pyrazol-1-yl)-phenyl]-(5,11-dihydro-pyrido[2,3-b][1,5]benzodiazepin-10-yl)-methanone.

8. A compound of claim 1 which is (5,11-dihydro-pyrido[2,3-b][1,5]benzodiazepin-6-yl)-[4-(3-methyl-pyrazol-1-yl)-2-trifluoromethyl-phenyl]-methanone or a pharmaceutically acceptable salt or ester form thereof.

9. A compound of claim 1 which is (5,11-dihydro-pyrido[2,3-b][1,5]benzodiazepin-6-yl)-[4-(3-methyl-pyrazol-1-yl)-2-trifluoromethyl-phenyl]-methanone 1:1 salt with trifluoromethanesulfonic acid.

10. A compound of claim 1 which is (5,11-dihydro-pyrido[2,3-b][1,5]benzodiazepin-6-yl)-[4-(3-methyl-pyrazol-1-yl)-2-trifluoromethyl-phenyl]-methanone 1:1 salt with hydrochloric acid.

11. A compound of claim 1 which is (5,11-dihydro-pyrido[2,3-b][1,5]benzodiazepin-6-yl)-[4-(5-methyl-pyrazol-1-yl)-2-trifluoromethyl-phenyl]-methanone or a pharmaceutically acceptable salt or ester form thereof.

12. A compound of claim 1 which is (5,11-dihydro-pyrido[2,3-b][1,5]benzodiazepin-6-yl)-[2-trifluoromethyl-4-(3-trifluoromethyl-pyrazol-1-yl)-phenyl]-methanone or a pharmaceutically acceptable salt or ester form thereof.

13. A compound of claim 1 which is (11-methyl-5,11-dihydro-pyrido[2,3-b][1,5]benzodiazepin-6-yl)-[4-(3-methyl-pyrazol-1-yl)-2-trifluoromethyl-phenyl]-methanone or a pharmaceutically acceptable salt or ester form thereof.

14. A compound of claim 1 which is (5,11-dihydro-pyrido[2,3-b][1,5]benzodiazepin-6-yl)-[2-fluoro-4-(3-methyl-pyrazol-1-yl)-phenyl]-methanone or a pharmaceutically acceptable salt or ester form thereof.

15. A compound of claim 1 which is [2-Chloro4-(3-methyl-pyrazol-1-yl)-phenyl]-(5-methyl-5,11-dihydro-pyrido[2,3-b][1,5]benzodiazepin-10-yl)-methanone.

16. A compound of claim 1 which is [4-(3-tert-Butyl-pyrazol-1-yl)-2-trifluoromethyl-phenyl]-(5,11-dihydro-pyrido[2,3-b][1,5]benzodiazepin-10-yl)-methanone.

17. A compound of claim 1 which is [2-Chloro-4-(3-trifluoromethyl-pyrazol-1-yl)-phenyl]-(5,11-dihydro-pyrido[2,3-b][1,5]benzodiazepin-6-yl)-methanone.

18. A compound of claim 1 which is [2-Chloro-4-(1-methyl-1H-pyrazol-3-yl)-phenyl]-(5,11-dihydro-pyrido[2,3-b][1,5]benzodiazepin-10-yl)-methanone.

19. A compound of claim 1 which is [2-Chloro-4-(1-methyl-1H-pyrazol-3-yl)-phenyl]-(5-methyl-5,11-dihydro-pyrido[2,3-b][1,5]benzodiazepin-10-yl)-methanone.

20. A compound of claim 1 which is [2-Chloro-4-(5-methyl-1H-[1,2,4]triazol-3-yl)-phenyl]-(5,11-dihydro-pyrido[2,3-b][1,5]benzodiazepin-6-yl)-methanone.

21. A method of treating disorders in a mammal which are remedied or alleviated by vasopressin agonist activity, the method comprising administering to the mammal in need thereof a pharmaceutically effective amount of a compound of claim 1, or a pharmaceutically acceptable salt or ester form thereof, and a suitable pharmaceutical carrier.

22. The method of claim 21 wherein the disorder which is remedied or alleviated by vasopressin agonist activity is selected from the group of diabetes insipidus, nocturnal enuresis, nocturia, urinary incontinence, bleeding and coagulation disorders, or the inability to temporarily delay urination.

23. A pharmaceutical composition useful for treating disorders which are remedied or alleviated by vasopressin agonist activity in a mammal, the composition comprising a pharmaceutically effective amount of a compound of claim 1 in combination or association with a pharmaceutically acceptable carrier.

24. The pharmaceutical composition of claim 23 wherein the disorder remedied or alleviated by vasopressin agonist activity in a mammal is selected from the group of diabetes insipidus, nocturnal enuresis, nocturia, urinary incontinence, bleeding and coagulation disorders, or the inability to temporarily delay urination.

* * * * *